US009324954B2

(12) United States Patent
Parham et al.

(10) Patent No.: US 9,324,954 B2
(45) Date of Patent: Apr. 26, 2016

(54) MATERIALS FOR ORGANIC ELECTROLUMINESCENT DEVICES

(75) Inventors: Amir Hossain Parham, Frankfurt am Main (DE); Christof Pflumm, Darmstadt (DE); Rémi Manouk Anémian, Seoul (KR); Hubert Spreitzer, Viernheim (DE)

(73) Assignee: Merck Patent GmbH (DE)

( * ) Notice: Subject to any disclaimer, the term of this patent is extended or adjusted under 35 U.S.C. 154(b) by 298 days.

(21) Appl. No.: 13/988,351

(22) PCT Filed: Oct. 27, 2011

(86) PCT No.: PCT/EP2011/005423
§ 371 (c)(1),
(2), (4) Date: May 20, 2013

(87) PCT Pub. No.: WO2012/069121
PCT Pub. Date: May 31, 2012

(65) Prior Publication Data
US 2013/0240796 A1    Sep. 19, 2013

(30) Foreign Application Priority Data

Nov. 24, 2010  (EP) .................................... 10014930

(51) Int. Cl.
| H01L 51/50 | (2006.01) |
| H01L 51/00 | (2006.01) |
| C07D 403/10 | (2006.01) |
| C07D 403/14 | (2006.01) |
| C07D 487/02 | (2006.01) |
| C07D 491/02 | (2006.01) |
| C07D 495/02 | (2006.01) |
| C09K 11/06 | (2006.01) |
| H05B 33/14 | (2006.01) |
| C09B 57/00 | (2006.01) |

(52) U.S. Cl.
CPC .......... *H01L 51/0072* (2013.01); *C07D 403/10* (2013.01); *C07D 403/14* (2013.01); *C07D 487/02* (2013.01); *C07D 491/02* (2013.01); *C07D 495/02* (2013.01); *C09B 57/00* (2013.01); *C09K 11/06* (2013.01); *H05B 33/14* (2013.01); *C09K 2211/1007* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/1092* (2013.01); *H01L 51/5016* (2013.01); *Y02E 10/549* (2013.01)

(58) Field of Classification Search
None
See application file for complete search history.

(56) References Cited

U.S. PATENT DOCUMENTS

| 8,859,132 | B2 | 10/2014 | West et al. |
| 2010/0187977 | A1 | 7/2010 | Kai et al. |
| 2011/0121274 | A1 | 5/2011 | Parham et al. |
| 2012/0080670 | A1* | 4/2012 | Park et al. ........................ 257/40 |
| 2013/0056720 | A1 | 3/2013 | Kim et al. |

FOREIGN PATENT DOCUMENTS

| CN | 101511834 A | 8/2009 |
| EP | 2080762 A1 | 7/2009 |
| JP | 2012-056880 A | 3/2012 |
| JP | 2012-516542 A | 7/2012 |
| JP | 2013-533604 A | 8/2013 |
| WO | WO-2010/015306 A1 | 2/2010 |
| WO | WO 2010/114243 A2 * | 10/2010 .............. C09K 11/06 |
| WO | WO-2010/114243 A2 | 10/2010 |

OTHER PUBLICATIONS

International Search Report for PCT/EP2011/005423 mailed Dec. 30, 2011.
English Translation of Japanese Office Action mailed on Jul. 28, 2015 for Japanese Application No. 2013-540251.

* cited by examiner

*Primary Examiner* — Gregory Clark
(74) *Attorney, Agent, or Firm* — Drinker Biddle & Reath LLP

(57) ABSTRACT

The present invention relates to compounds of the formula (1) and formula (2) which are suitable for use in electronic devices, in particular in organic electroluminescent devices.

19 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. §371) of PCT/EP2011/005423, filed Oct. 27, 2011, which claims benefit of European application 10014930.1, filed Nov. 24, 2010.

The present invention relates to materials for use in electronic devices, in particular in organic electroluminescent devices. The materials are particularly suitable as matrix materials for phosphorescent emitters.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed here are increasingly organo-metallic complexes which exhibit phosphorescence instead of fluorescence (M. A. Baldo et al., *Appl. Phys. Lett.* 1999, 75, 4-6). For quantum-mechanical reasons, an up to four-fold energy and power efficiency is possible using organometallic compounds as phosphorescent emitters. In general, however, there is still a need for improvement, for example with respect to operating voltage, efficiency and lifetime, in the case of OLEDs, in particular also in the case of OLEDs which exhibit triplet emission (phosphorescence). This applies, in particular, to OLEDs which emit in the relatively short-wave region.

The properties of phosphorescent OLEDs are determined not only by the triplet emitters employed. In particular, the other materials used, such as matrix materials, hole-blocking materials and electron-transport materials, are also of importance here. Improvements in these materials may thus also result in significant improvements in the OLED properties. There is also still a need for improvement in the case of these materials for fluorescent OLEDs.

In accordance with the prior art, triazine derivatives (for example in accordance with WO 2010/015306 or WO 2008/056746), inter alia, are used as matrix materials for phosphorescent emitters. However, there is still a need for improvement, in particular with respect to the operating voltage, but also with respect to the efficiency and the lifetime of the device, on use of these matrix materials, as in the case of other matrix materials.

The object of the present invention is the provision of compounds which are suitable for use in a fluorescent or phosphorescent OLED, in particular a phosphorescent OLED, for example as matrix material or as electron-transport or hole-blocking material. In particular, the object of the present invention is to provide matrix materials which are also suitable for green- and blue-phosphorescent OLEDs and to provide novel electron-transport materials.

Surprisingly, it has been found that certain pyrimidine compounds, described in greater detail below, in which a pyrimidine group is bonded to a certain carbazole group via an ortho- or meta-linked phenyl group achieve this object and result in improvements in the organic electroluminescent device, in particular with respect to the operating voltage, the lifetime and/or the efficiency. This applies, in particular, to green- and, depending on the precise structure, also to blue-phosphorescent electroluminescent devices, especially on use of the compounds according to the invention as matrix material, but also to the use of the compounds as electron-transport material or hole-blocking material. The present invention therefore relates to these materials and to organic electroluminescent devices which comprise compounds of this type.

JP 4474493 B1 discloses carbazole derivatives which contain, as substituents, a phenyl group which are substituted by a pyrimidine group in the meta-position. There is still a further need for improvement in the case of these compounds, in particular with respect to the operating voltage.

Surprisingly, it has been found that, in particular, the use of the compounds according to the invention in organic electroluminescent devices results in very good electronic properties, in particular in an improvement in the operating voltage.

The present invention therefore relates to a compound of the following formula (1) or formula (2),

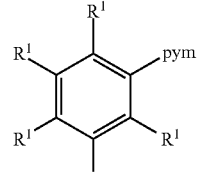

formula (1)

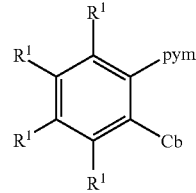

formula (2)

where the following applies to the symbols used:

pym is a pyrimidine, which may be substituted by one or more radicals R;

Cb is a carbazole derivative which contains at least 2 bridges, in which, in addition, one or more C atoms may be replaced by N and which may be substituted by one or more radicals $R^2$;

R, $R^1$, $R^2$ is selected on each occurrence, identically or differently, from the group consisting of H, D, F, Cl, Br, I, CN, $NO_2$, $N(Ar)_2$, $N(R^3)_2$, $C(=O)Ar$, $C(=O)R^3$, $P(=O)(Ar)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^3$, where one or more non-adjacent $CH_2$ groups may be replaced by $R^3C=CR^3$, $C=C$, $Si(R^3)_2$, $C=O$, $C=S$, $C=NR^3$, $P(=O)(R^3)$, SO, $SO_2$, $NR^3$, O, S or $CONR^3$ and where one or more H atoms may be replaced by D, F, Cl, Br, I, CN or $NO_2$, an aromatic or heteroaromatic ring system having 5 to 80, preferably 5 to 60, aromatic ring atoms, which may in each case be substituted by one or more radicals $R^3$, an aryloxy or heteroaryloxy group having 5 to 60 aromatic ring atoms, which may be substituted by one or more radicals $R^3$, or an aralkyl or heteroaralkyl group having 5 to 60 aromatic ring atoms, which may be substituted by one or more radicals $R^3$, where two or more adjacent substituents $R^2$ may optionally form a monocyclic or polycyclic, aliphatic, aromatic or heteroaromatic ring system, which may be substituted by one or more radicals $R^3$;

$R^3$ is selected on each occurrence, identically or differently, from the group consisting of H, D, F, Cl, Br, I, CN, $NO_2$, N(Ar)$_2$, N(R$^4$)$_2$, C(=O)Ar, C(=O)R$^4$, P(=O)(Ar)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R$^3$, where one or more non-adjacent CH$_2$ groups may be replaced by R$^4$C=CR$^4$, C≡C, Si(R$^4$)$_2$, C=O, C=S, C=Se, C=NR$^4$, P(=O)(R$^4$), SO, SO$_2$, NR$^4$, O, S or CONR$^4$ and where one or more H atoms may be replaced by D, F, Cl, Br, I, CN or NO$_2$, an aromatic or heteroaromatic ring system having 5 to 60 aromatic ring atoms, which may in each case be substituted by one or more radicals R$^4$, an aryloxy or heteroaryloxy group having 5 to 60 aromatic ring atoms, which may be substituted by one or more radicals R$^4$, or an aralkyl or heteroaralkyl group having 5 to 60 aromatic ring atoms, where two or more adjacent substituents R$^3$ may optionally form a monocyclic or polycyclic, aliphatic, aromatic or heteroaromatic ring system, which may be substituted by one or more radicals R$^4$;

Ar is on each occurrence, identically or differently, an aromatic or heteroaromatic ring system having 5-30 aromatic ring atoms, which may be substituted by one or more non-aromatic radicals R$^4$; two radicals Ar here which are bonded to the same N atom or P atom may also be bridged to one another by a single bond or a bridge selected from N(R$^4$), C(R$^4$)$_2$, O or S;

R$^4$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents R$^4$ may form a mono- or polycyclic, aliphatic, aromatic or heteroaromatic ring system with one another;

the following compounds are excluded from the invention:

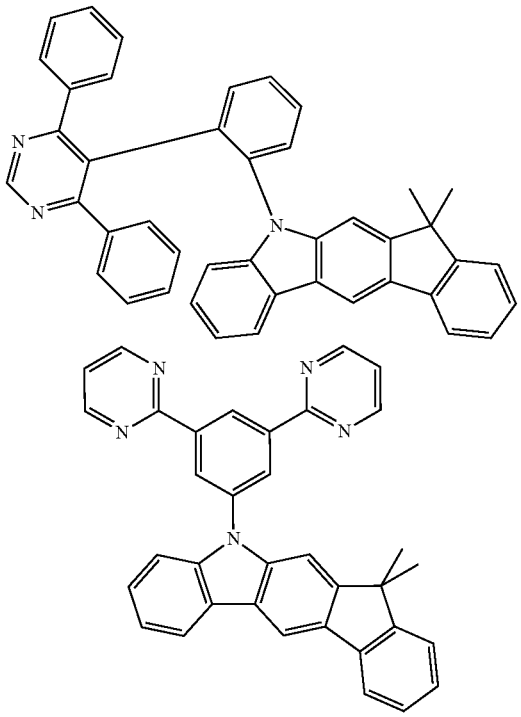

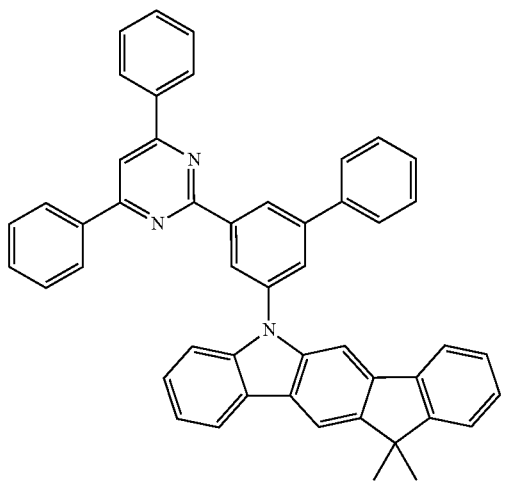

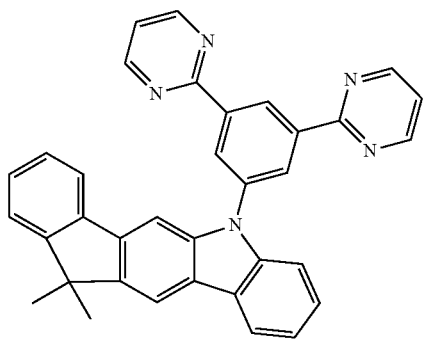

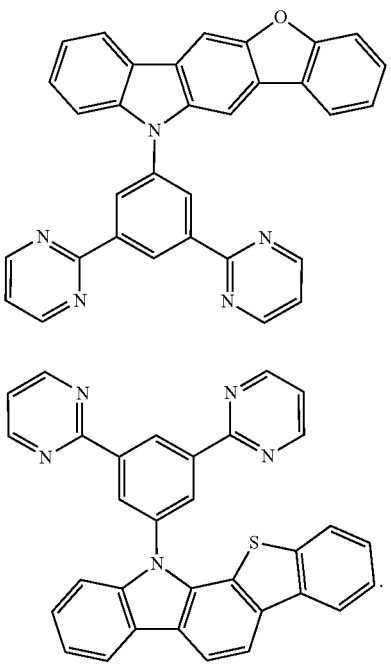

A carbazole derivative which contains at least two bridges and in which one or more C atoms may be replaced by N is taken to mean the following for the purposes of the present invention: carbazole has the following structure:

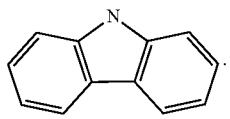

The nitrogen here is regarded as a bridge of the carbazole, since it bridges the two phenyl groups in addition to the single bond between the phenyl groups. The carbazole derivative in the sense of the present invention contains at least two bridges. This can take place in different ways. Thus, for example, it is possible for two or more carbazole groups of the above-mentioned formula to be bonded directly to one another. However, if two or more carbazole groups are bonded to one another via a further group which is not carbazole or another carbazole derivative, they are not regarded as carbazole derivative having two bridges in the sense of the present invention. Furthermore, a further aromatic group which contains a bridge to the phenyl group of the carbazole may be bonded to one or both phenyl groups of the carbazole. Again furthermore, an aromatic group which contains a bridge to one or both of the phenyl groups of the carbazole may be bonded to the nitrogen of the carbazole. It is also possible here for this aromatic group on the nitrogen of the carbazole to be bonded to the phenyl group depicted in formula (1) or formula (2). The bridges are selected from oxygen, sulfur or from in each case substituted or unsubstituted carbon or nitrogen, but are preferably not sulfur. Furthermore, nitrogen atoms may be present instead of one or more of the carbon atoms of the carbazole. In a preferred embodiment of the invention, a further aromatic group which contains a bridge to the phenyl group of the carbazole is bonded to one or both phenyl groups of the carbazole, or a further aromatic group which contains a bridge to one or both of the phenyl groups of the carbazole is bonded to the nitrogen of the carbazole.

The carbazole derivative can be bonded to the phenyl group in formula (1) or formula (2) either directly via the nitrogen or via a carbon atom of the phenyl rings or via an aromatic group which is bonded to the nitrogen of the carbazole.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, etc. Aromatic rings linked to one another by a single bond, such as, for example, biphenyl, are, by contrast, not referred to as an aryl or heteroaryl group, but instead as an aromatic ring system.

An aromatic ring system in the sense of this invention contains 6 to 80 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are connected, for example, by a short alkyl group. Furthermore, aromatic rings linked to one another by a single bond, such as, for example, biphenyl, terphenyl or quaterphenyl are referred to as an aromatic ring system in the sense of this application.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, cyclo-pentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy or 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoro-ethylthio, ethenylthio, propenylthio, butenylthio, pentenylthio, cyclo-pentenylthio, hexenylthio, cyclohexenylthio, heptenylthio, cycloheptenyl-thio, octenylthio, cyclooctenylthio, ethynylthio, propynylthio, butynylthio, pentynylthio, hexynylthio, heptynylthio or octynylthio. In general, alkyl, alkenyl, alkynyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, furthermore preferably F or CN, particularly preferably CN.

An aromatic or heteroaromatic ring system having 5-80 aromatic ring atoms, which may also in each case be substituted by the above-mentioned radicals $R^2$ or a hydrocarbon radical and which may be linked via any desired positions on the aromatic or heteroaromatic group, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, triphenylene, quaterphenyl, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phen-oxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatri-phenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, aza-carbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combinations of these systems.

In a preferred embodiment of the invention, the compounds of the formula (1) are selected from the compounds of the following formulae (1a) and (1b), and the compounds of the formula (2) are selected from the compounds of the following formula (2a),

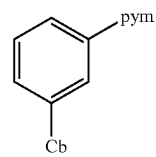

formula (1a)

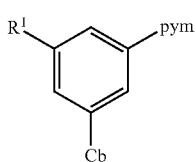

formula (1b)

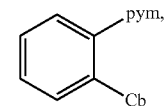

formula (2a)

where the symbols used have the meanings given above.

$R^1$ here in compounds of the formula (1b) is preferably an aromatic or heteroaromatic ring system having 5 to 24 aromatic ring atoms, which may also be substituted by one or more radicals $R^3$. In a particularly preferred embodiment, $R^1$ stands, identically or differently on each occurrence, for an aromatic or heteroaromatic ring system having 6 to 24 aromatic ring atoms, which contains no condensed aryl groups and which contains no condensed heteroaryl groups in which two or more aromatic or heteroaromatic 6-membered ring groups are condensed directly onto one another and which may in each case also be substituted by one or more radicals $R^3$. Thus, it is preferred for $R^1$ to contain, for example, no naphthyl groups or higher condensed aryl groups and likewise no quinoline groups, acridine groups, etc. By contrast, it is possible for R to contain, for example, carbazole groups, dibenzofuran groups, indolo- or indenocarbazole groups, etc., since no 6-membered aromatic or heteroaromatic rings are condensed directly onto one another in these structures.

In a particularly preferred embodiment of the invention, the compounds of the formula (1b) are selected from the compounds of the following formula (1c),

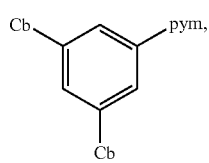

formula (1c)

where the symbols used have the meanings given above.

In a preferred embodiment of the formula (1) and (2) or (1a) to (1c) or (2a), the group pym is selected from the groups of the following formulae (3), (4) or (5),

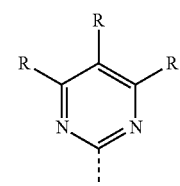

formula (3)

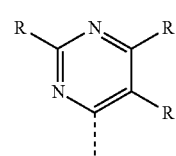

formula (4)

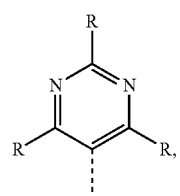

formula (5)

where the symbols used have the meanings given above and the dashed bond indicates the bond to the phenyl group in formula (1) and (2) or in formula (1a) to (1c) and (2a).

Particularly preferred embodiments of the formula (3), (4) and (5) are the pyrimidine structures of the following formulae (3a), (4a) and (5a),

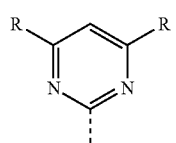

formula (3a)

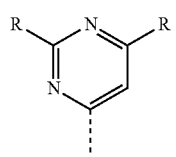

formula (4a)

-continued formula (5a)

where the symbols used have the meanings given above and the dashed bond represents the bond from the pyrimidine to the phenyl group of the formula (1) and (2) or (1a) to (1c) or (2a).

Very particular preference is given to the formulae (3a) and (4a).

In a preferred embodiment of the formulae (3), (4), (5), (3a), (4a) and (5a), R stands, identically or differently on each occurrence, for H, an alkyl group having 1 to 10 C atoms or for an aromatic or heteroaromatic ring system having 5 to 24 aromatic ring atoms, which may also be substituted by one or more radicals $R^3$. In a particularly preferred embodiment, R stands, identically or differently on each occurrence, for H or an aromatic or heteroaromatic ring system having 6 to 24 aromatic ring atoms, which contains no condensed aryl groups and which contains no condensed heteroaryl groups in which two or more aromatic or heteroaromatic 6-membered ring groups are condensed directly onto one another and which may in each case also be substituted by one or more radicals $R^3$. Thus, it is preferred for R to contain, for example, no naphthyl groups or higher condensed aryl groups and likewise no quinoline groups, acridine groups, etc. By contrast, it is possible for R to contain, for example, carbazole groups, dibenzofuran groups, etc., since no 6-membered aromatic or heteroaromatic rings are condensed directly onto one another in these structures. R in formula (3a) and (4a) is preferably not equal to hydrogen. In a very particularly preferred embodiment of the invention, R is equal to phenyl, biphenyl, terphenyl or quaterphenyl, each of which may be substituted by one or more radicals $R^3$, but is preferably unsubstituted.

As stated above, Cb is a carbazole derivative which contains at least 2 bridges, in which, in addition, one or more C atoms may be replaced by N and which may be substituted by one or more radicals $R^2$.

Preferred groups Cb are the groups of the following formulae (6) to (22), formula (6)

formula (7)

formula (8)

formula (9)

formula (10)

formula (11)

formula (12)

formula (13)

formula (14)

formula (15)

formula (16)

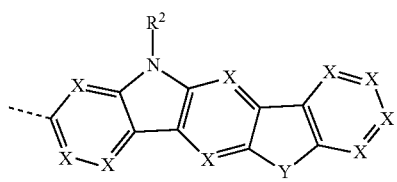

formula (17)

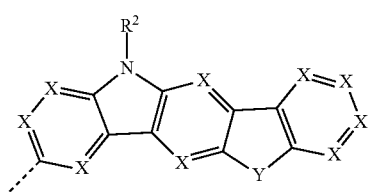

formula (18)

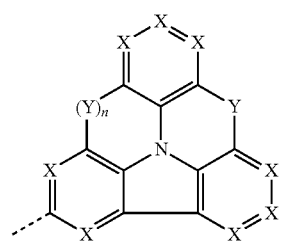

formula (19)

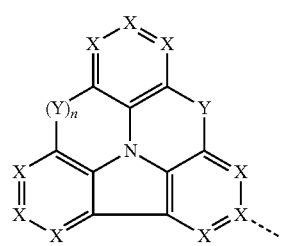

formula (20)

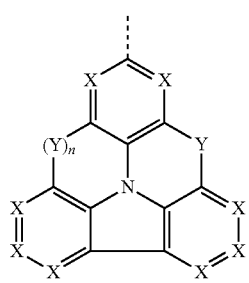

formula (21)

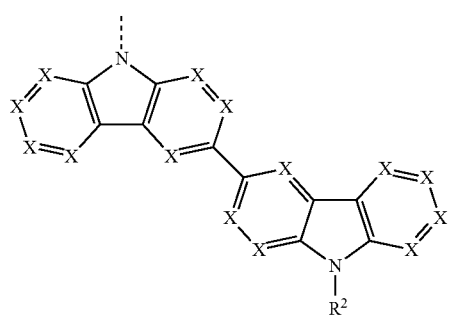

formula (22)

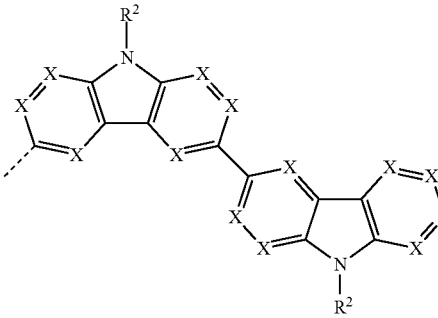

where the symbols used have the meanings given above, the dashed bond represents the bond from the carbazole derivative to the phenyl group of the formula (1) or (2) or (1a) to (1c) or (2a) and furthermore:

X is on each occurrence, identically or differently, $CR^2$ or N, where a maximum of 2 symbols X per ring stand for N;

Y is on each occurrence, identically or differently, $C(R^2)_2$, $NR^2$, O or S; Y is preferably not S;

n is 0 or 1, where n equals 0 means that no group Y is bonded at this position and instead radicals $R^2$ are bonded to the corresponding car-bon atoms.

Preference is furthermore given to carbazole groups in which two or more of the above-mentioned formulae (6) to (22) are bonded directly to one another by a single bond.

It should be emphasised here that the presence of radicals which form a ring system with one another means that structures containing further condensed-on indeno or indolo groups or other condensed-on groups are also accessible. This is shown by way of example starting from structures (6) and (18) depicted above:

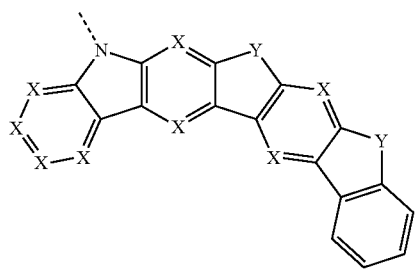

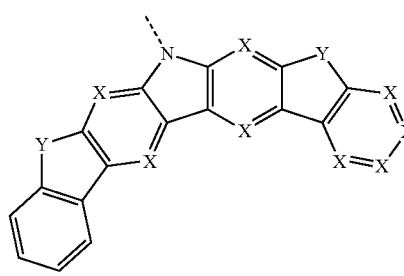

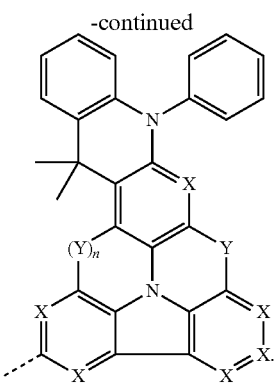

This is only an illustrative representation of which structures may be accessible by ring formation of the substituents on formula (6) to (22). It is therefore possible for the person skilled in the art, without further inventive step, to use further structures having condensed-on rings starting from the carbazole structures of the formula (6) to (22).

In preferred groups Cb of the above-mentioned formulae (6) to (22), the symbol X stands, identically or differently on each occurrence, for $CR^2$, in particular for CH.

The substituent $R^2$ in these groups, which is bonded directly to a nitrogen atom in the bridge of a carbazole derivative, furthermore preferably stands for an aromatic or heteroaromatic ring system having 5 to 24 aromatic ring atoms, which may also be substituted by one or more radicals $R^3$. In a particularly preferred embodiment, this substituent $R^2$ stands, identically or differently on each occurrence, for an aromatic or heteroaromatic ring system having 6 to 24 aromatic ring atoms, which contains no condensed aryl groups and which contains no condensed heteroaryl groups in which two or more aromatic or heteroaromatic 6-membered ring groups are condensed directly onto one another and which may in each case also be substituted by one or more radicals $R^3$.

In a further preferred embodiment of the invention, Y in the formulae (6) to (22) stands, identically or differently on each occurrence, for $C(R^2)_2$ or for $NR^2$. If Y stands for $NR^2$, $R^2$ preferably has the same meanings as preferably indicated above for the substituents which are bonded directly to N. If Y stands for $C(R^2)_2$, $R^2$ preferably stands, identically or differently on each occurrence, for a linear alkyl group having 1 to 10 C atoms or for a branched or cyclic alkyl group having 3 to 10 C atoms or for an aromatic or heteroaromatic ring system having 5 to 24 aromatic ring atoms, which may also be substituted by one or more radicals $R^3$. In this case, $R^2$ very particularly preferably stands for a methyl group or for a phenyl group.

In a further preferred embodiment of the invention, the radical $R^3$, which may be in the form of a radical on R, $R^1$ or $R^2$, is equal to H.

The above-mentioned embodiments can be combined with one another as desired. In particular, it is preferred to combine the above-mentioned preferred embodiments with one another, i.e. the compounds of the formula (1a) to (1c) or (2a) with the pyrimidine groups of the formulae (3), (4) or (5) or (3a), (4a) or (5a) and with the carbazole derivatives of the formulae (6) to (22); the compounds furthermore also preferably contain the substituents mentioned as preferred above and the groups Y mentioned as preferred above.

Examples of preferred compounds in accordance with the above-mentioned embodiments or compounds, as can preferably be employed in organic electronic devices, are the following compounds.

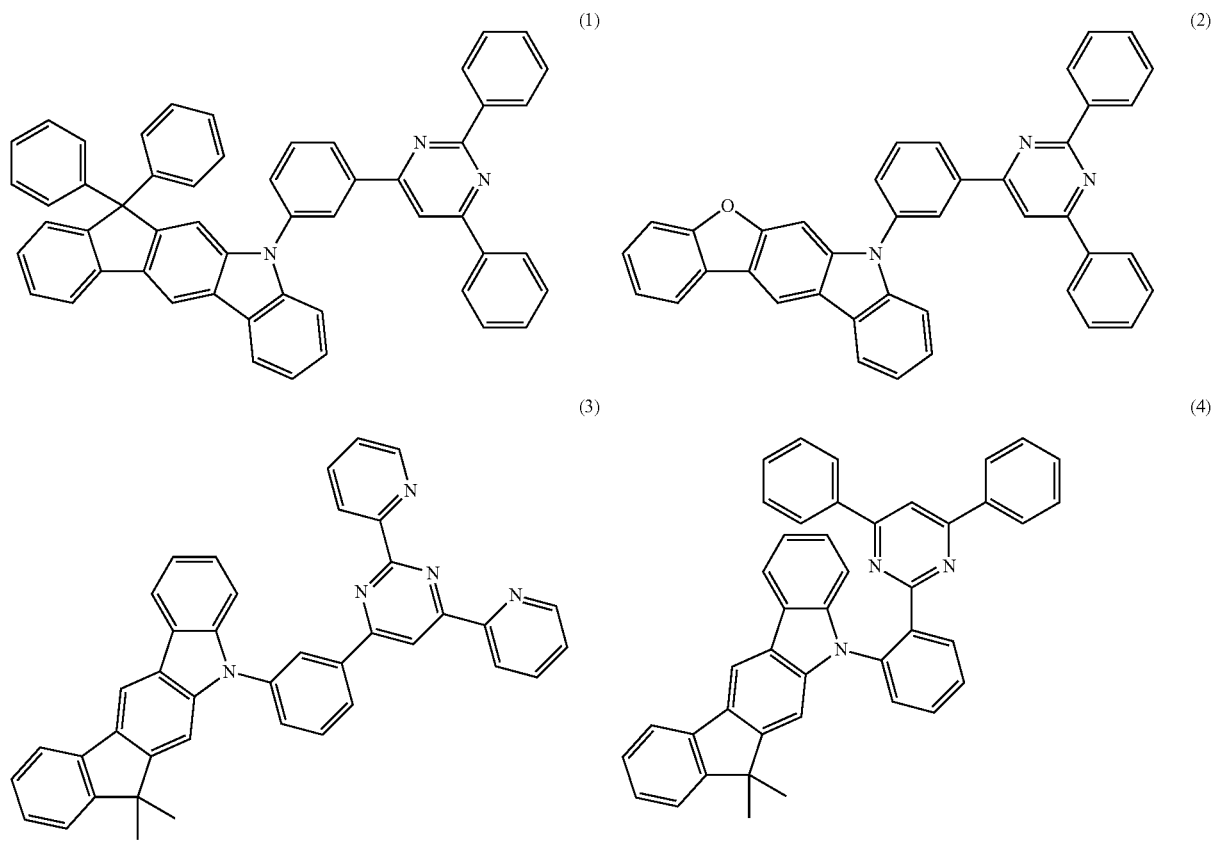

-continued
(5)
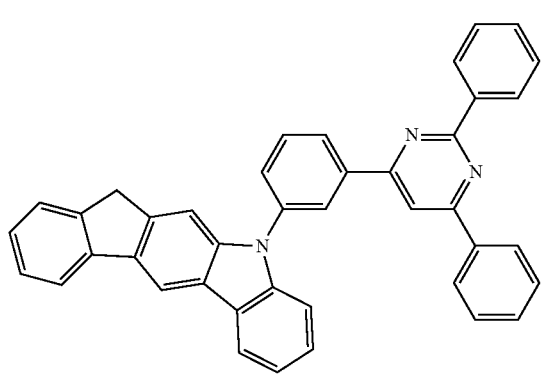
(6)
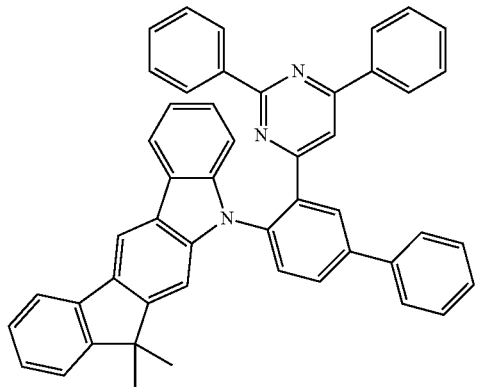
(7)
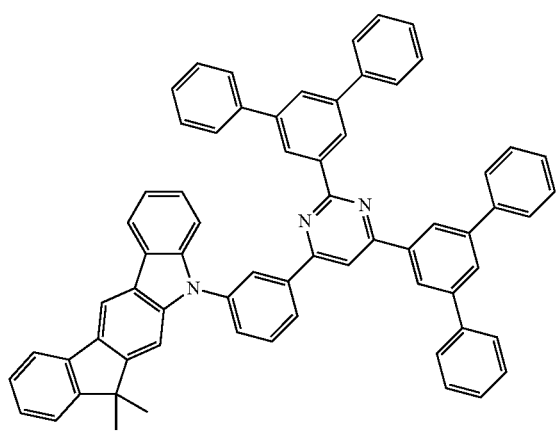
(8)
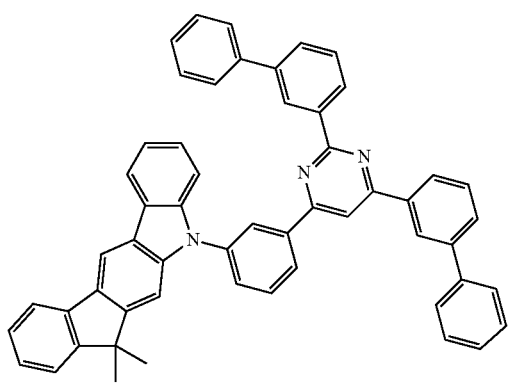
(9)
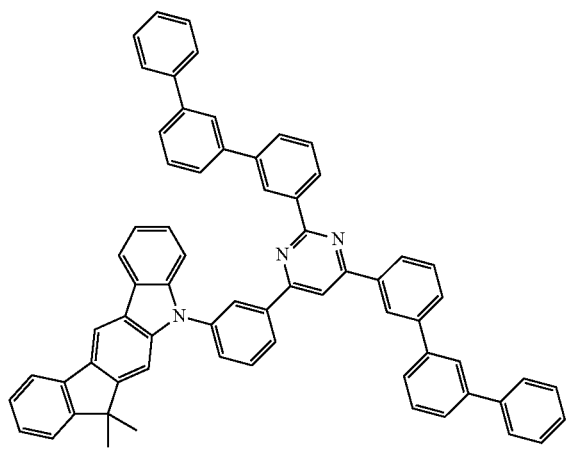
(10)
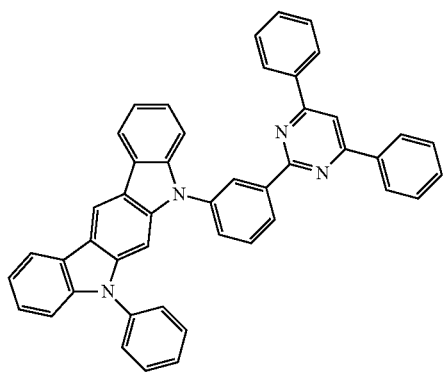

-continued
(11)
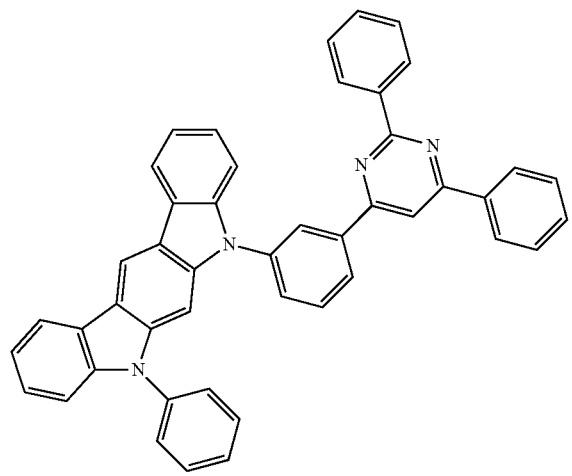
(12)
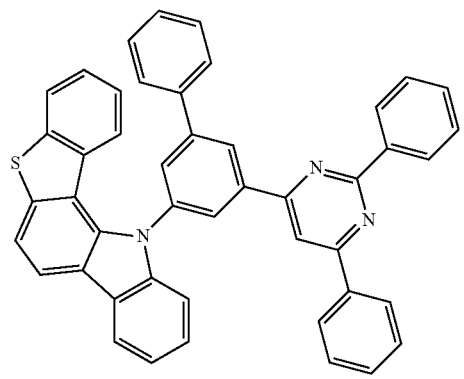
(13)
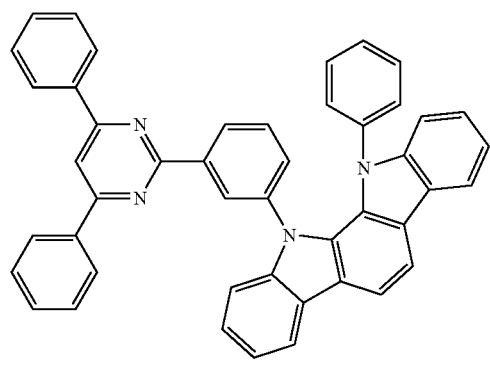
(14)
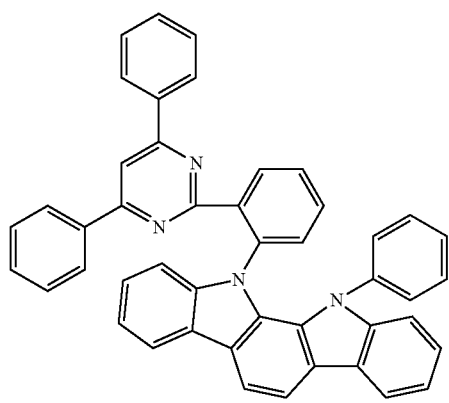
(15)
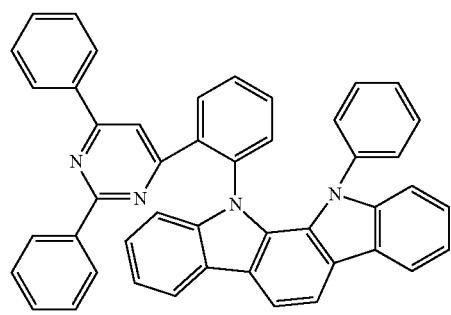
(16)
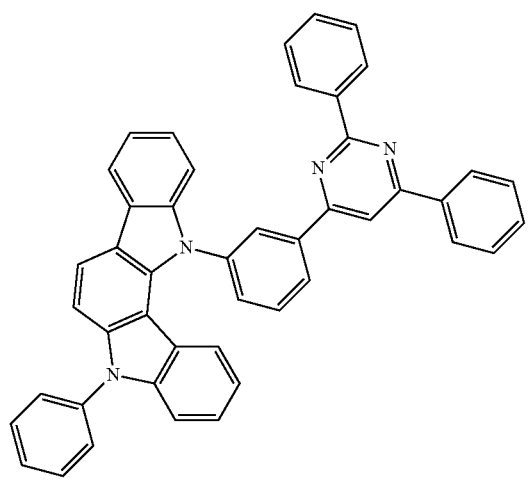

-continued
(17)
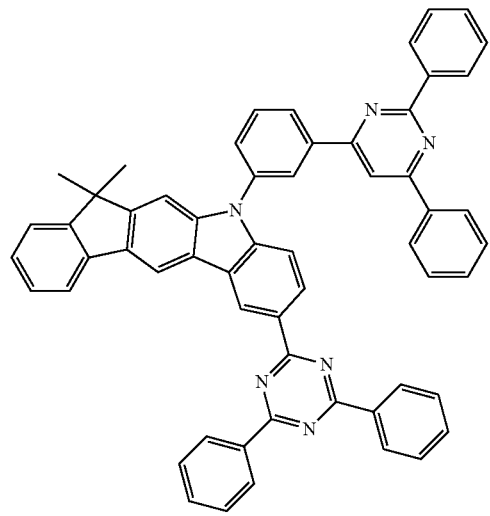
(18)
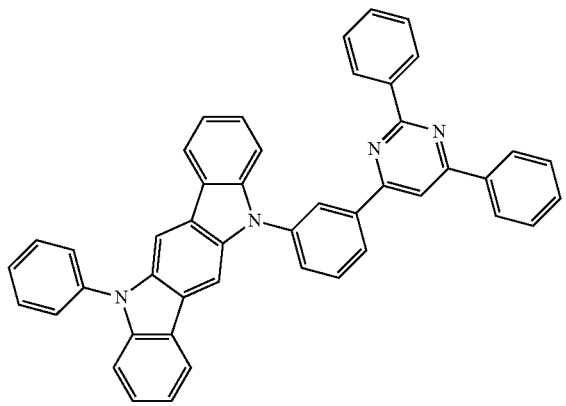
(19)
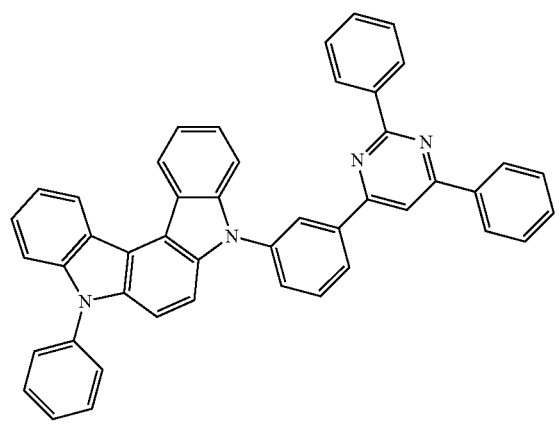
(20)
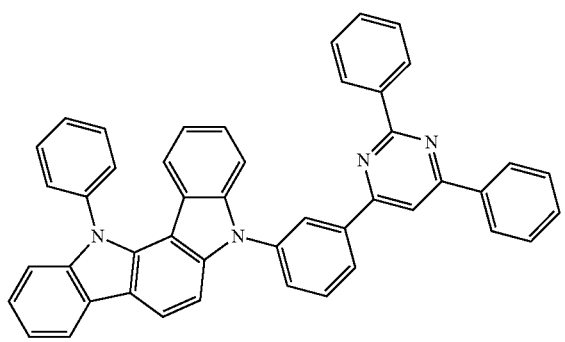
(21)
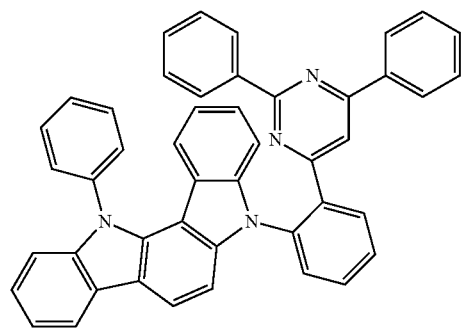
(22)
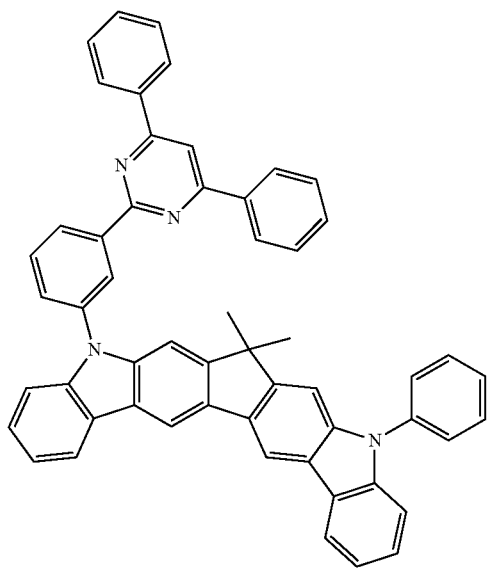

-continued
(23)
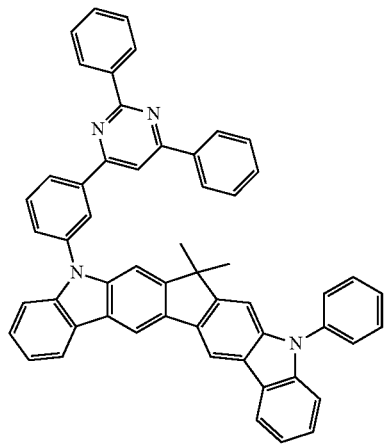
(24)
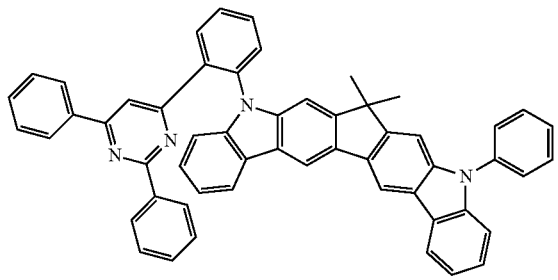
(25)
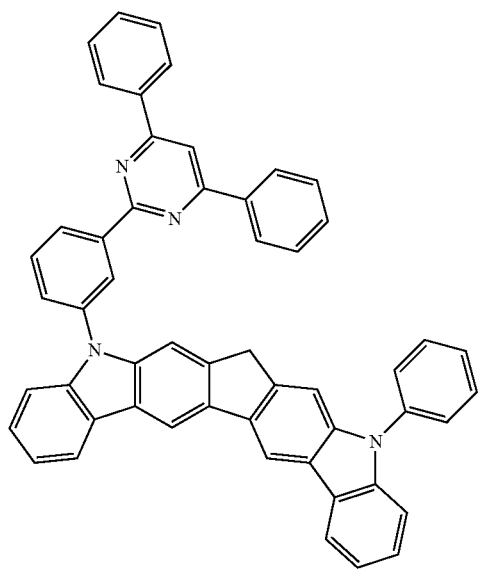
(26)
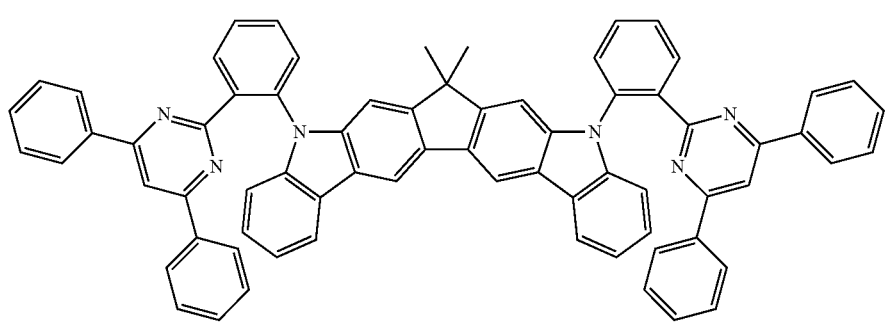

-continued
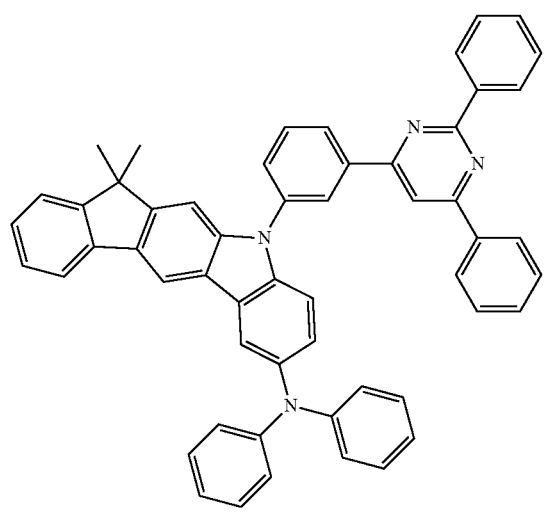
(27)
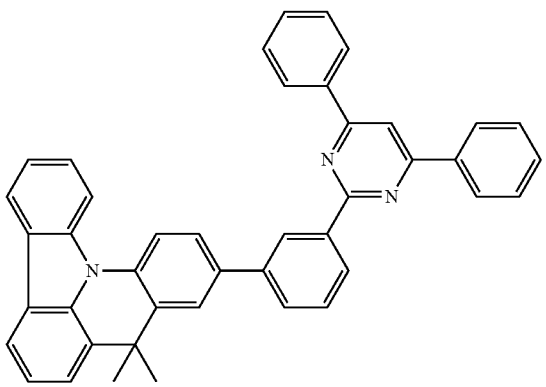
(28)
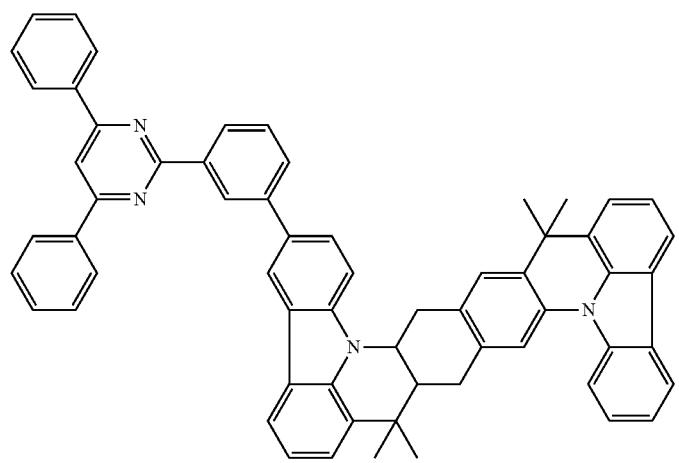
(29)
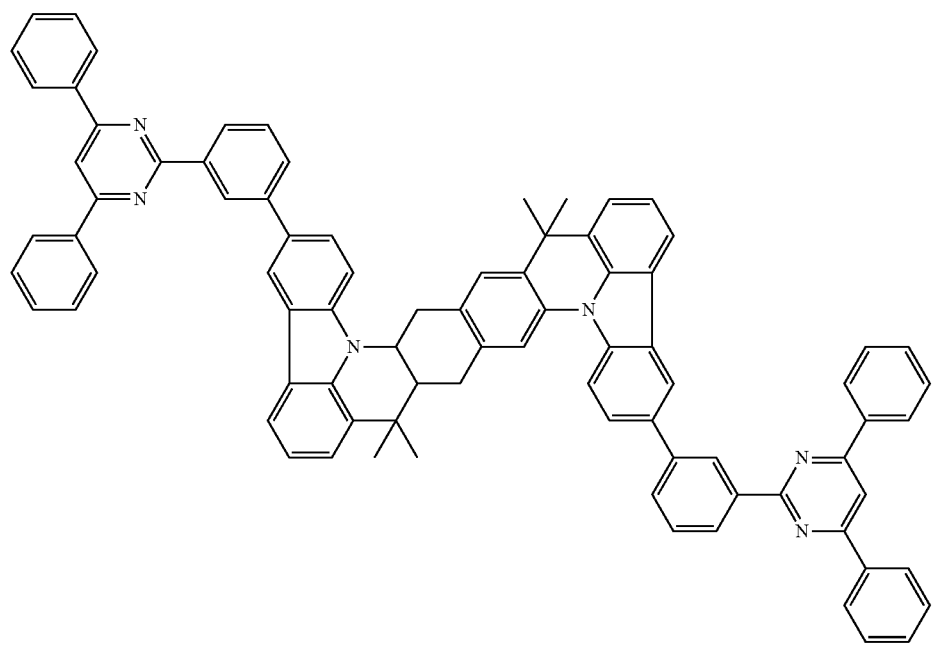
(30)

(31)
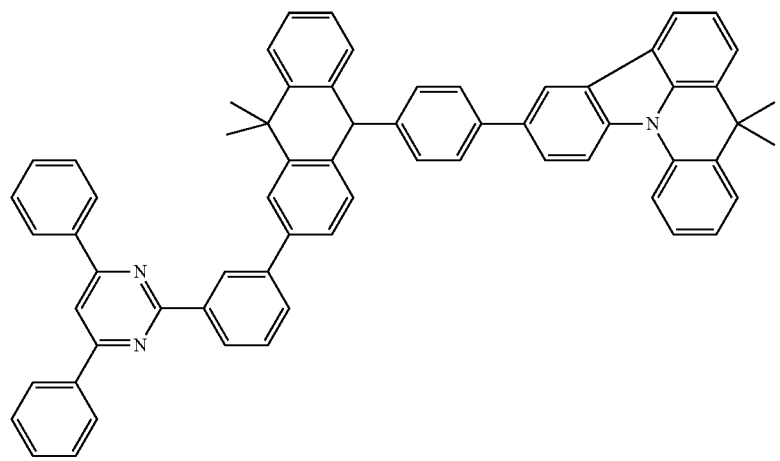
(32)
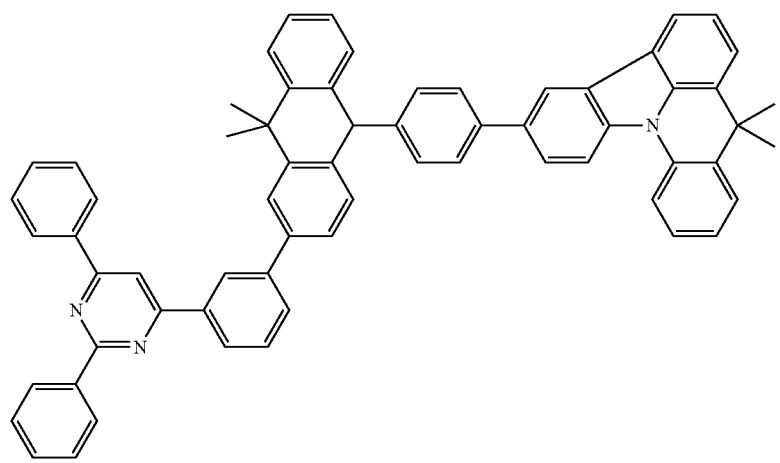
(33) (34)
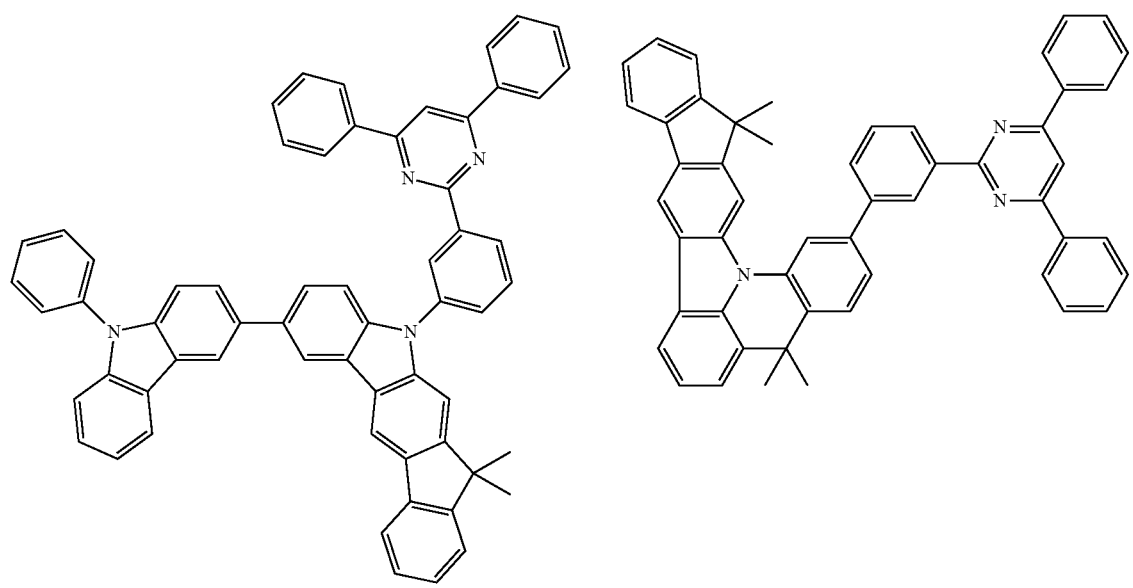

-continued
(35)
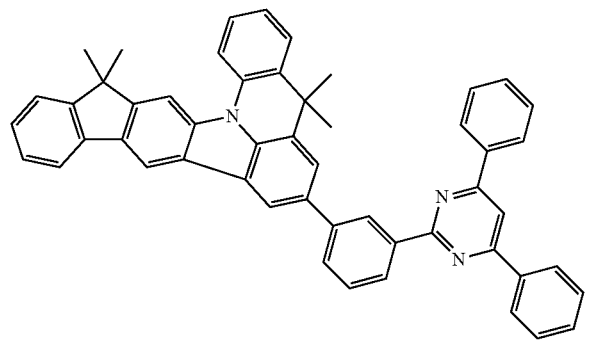
(36)
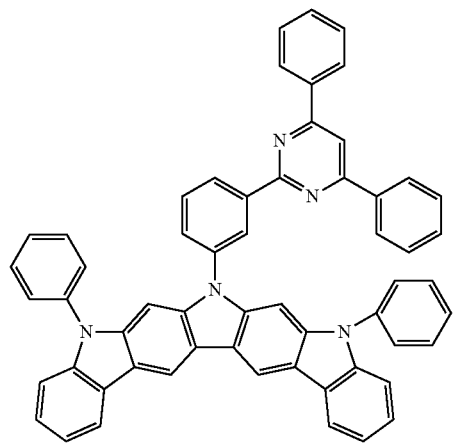
(37)
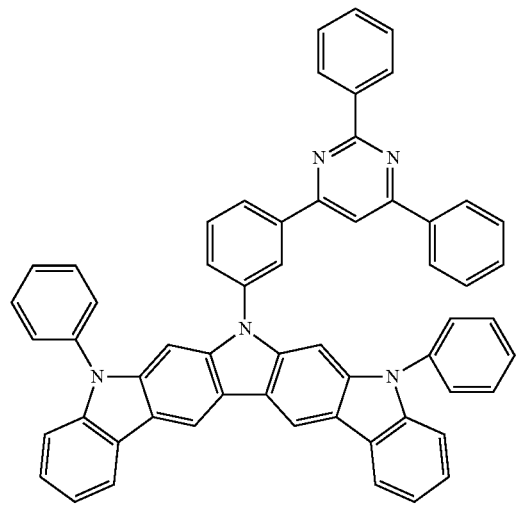
(38)
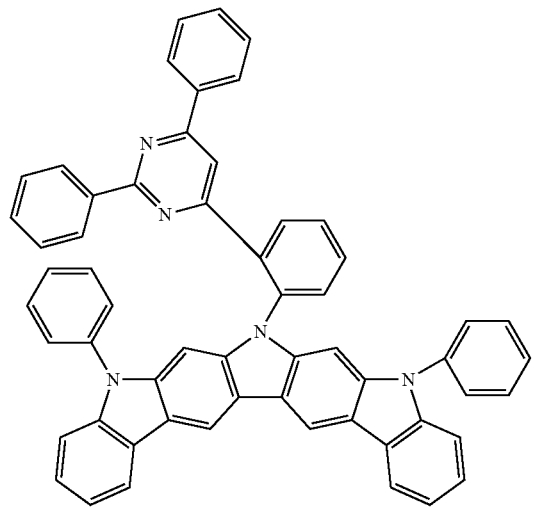
(39)
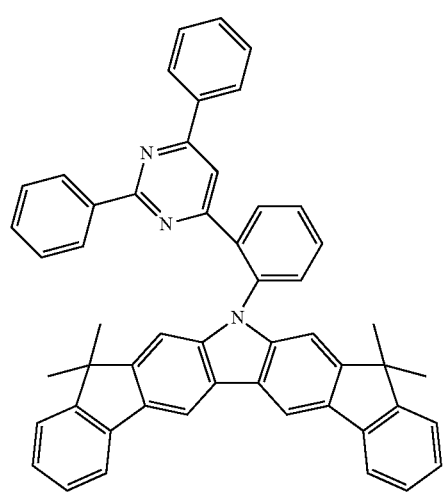
(40)
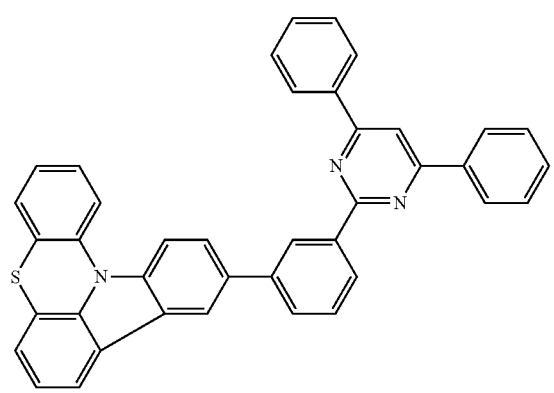

-continued
(41)
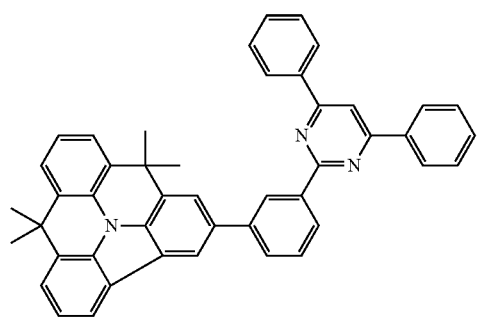
(42)
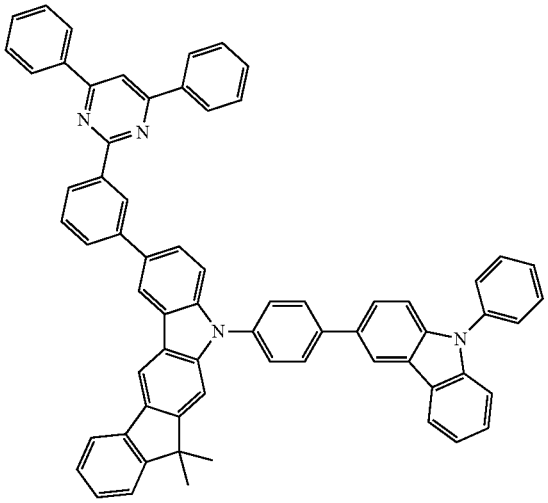
(43)
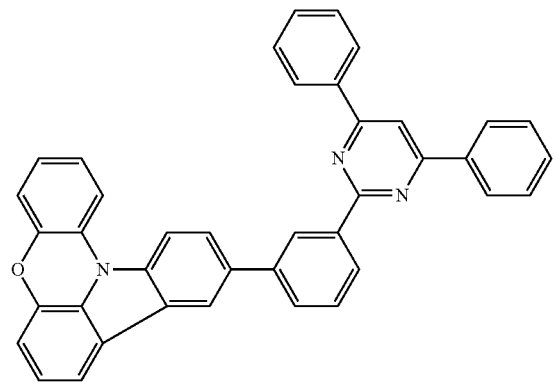
(44)
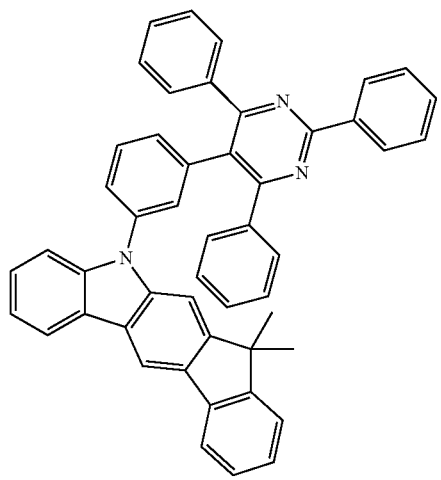
(45)
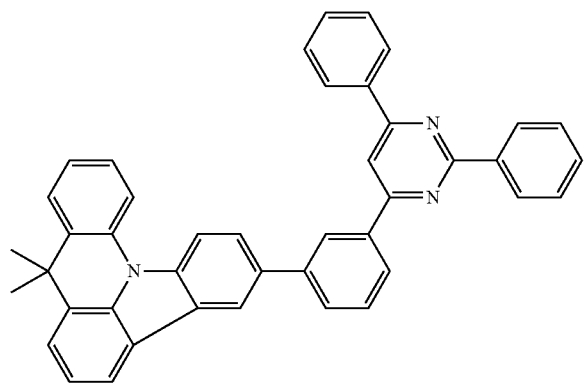
(46)
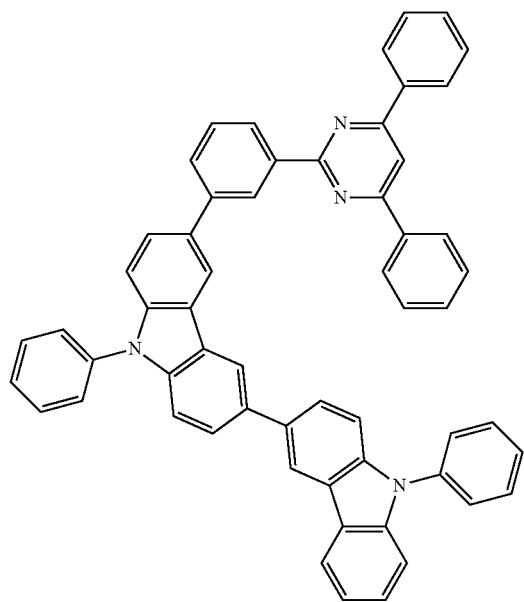

-continued
(47)
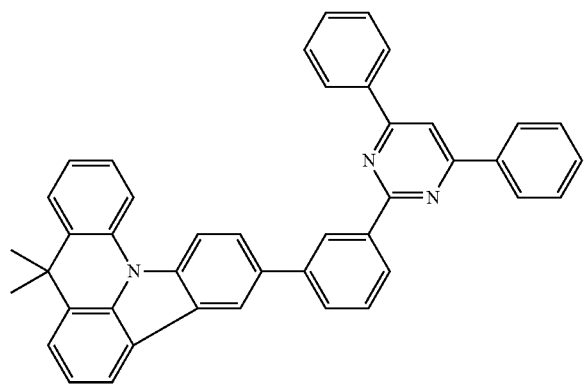
(48)
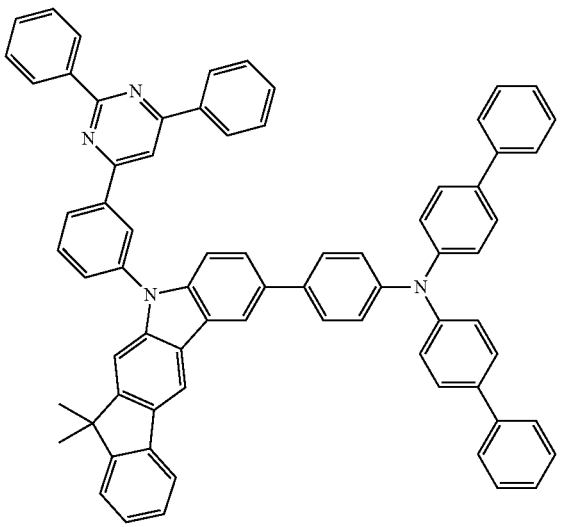
(49)
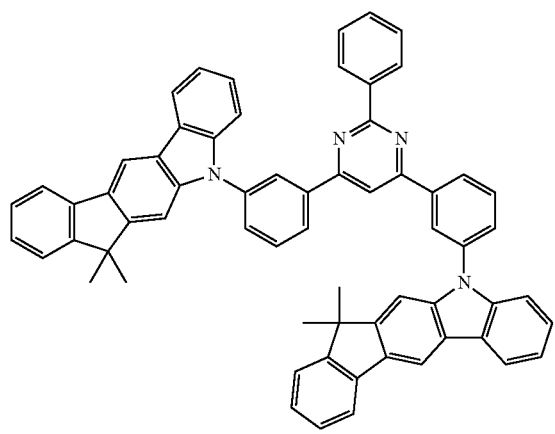
(50)
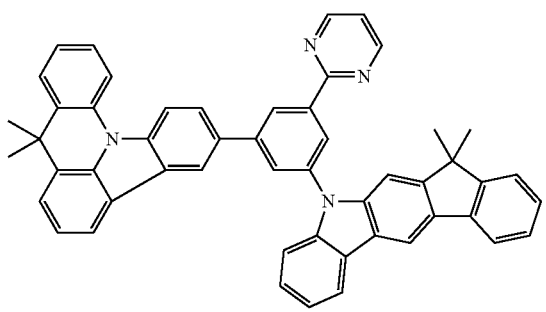
(51)
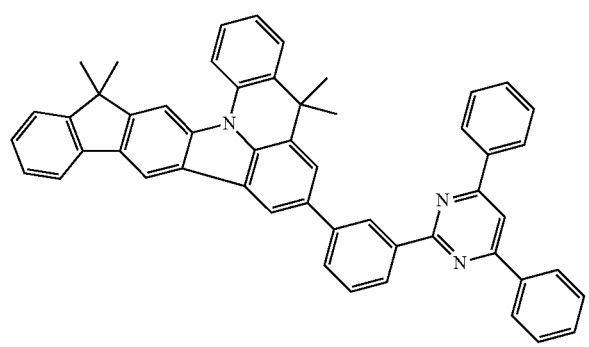
(52)
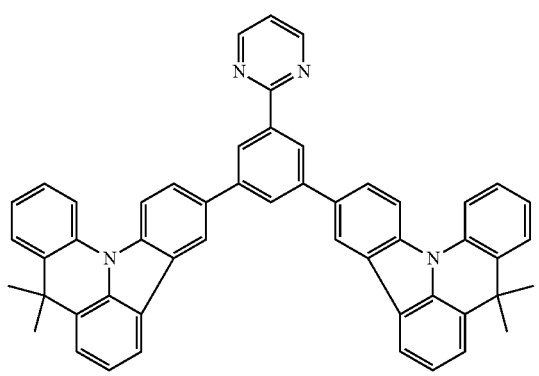

-continued
(53)
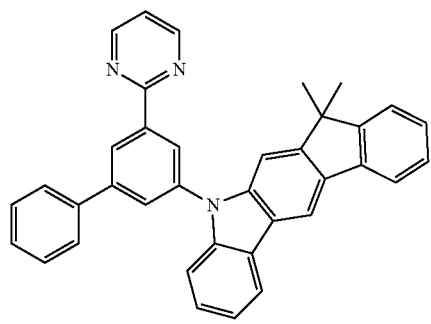
(54)
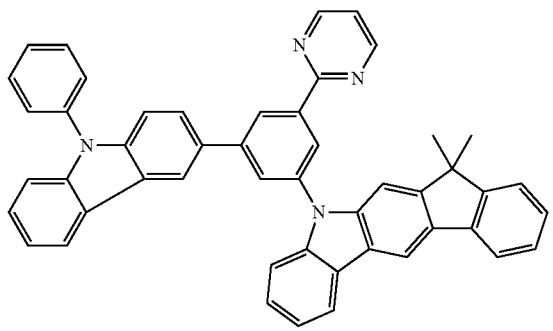
(55)
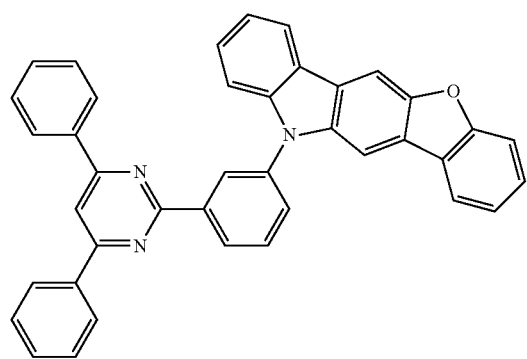
(56)
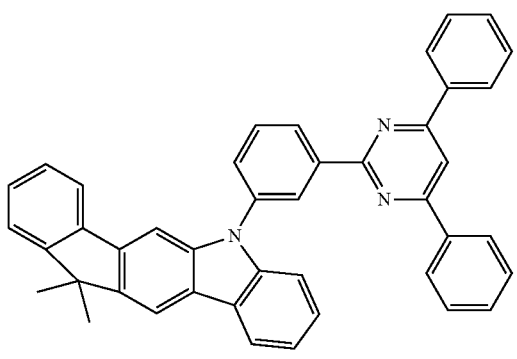
(57)
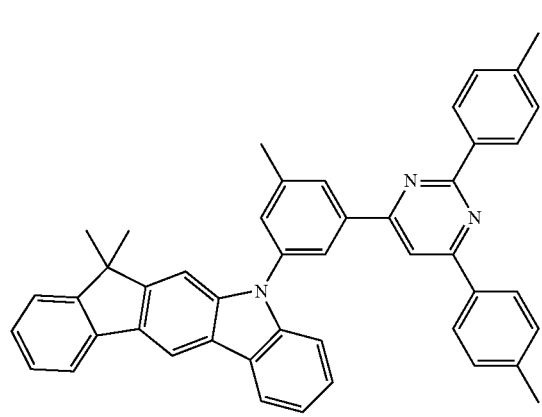
(58)
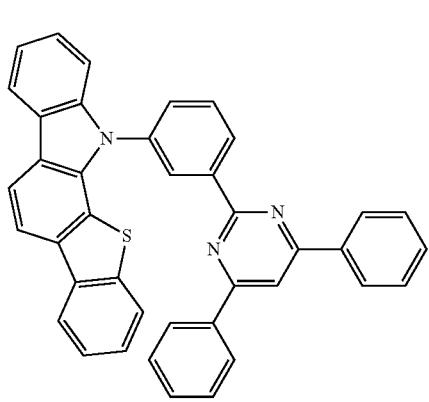

-continued
(59)
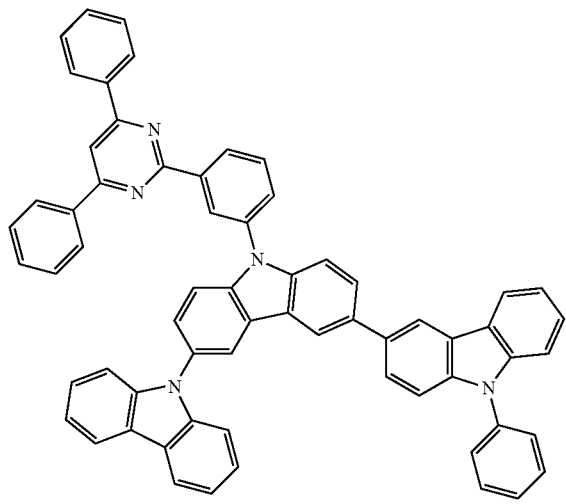
(60)
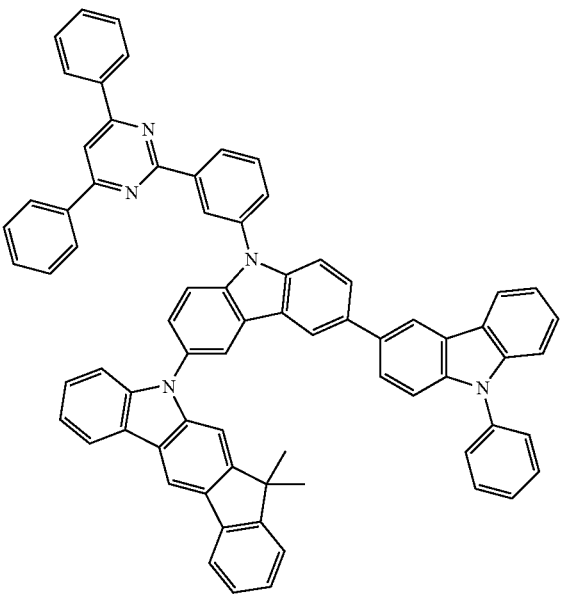
(61)
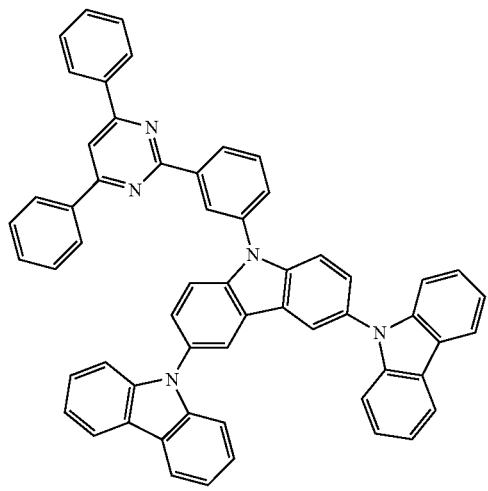
(62)
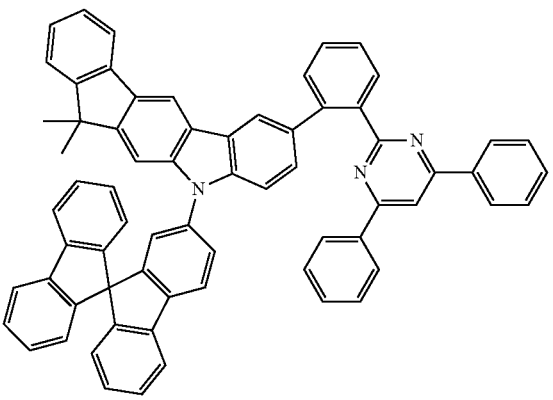
(63)
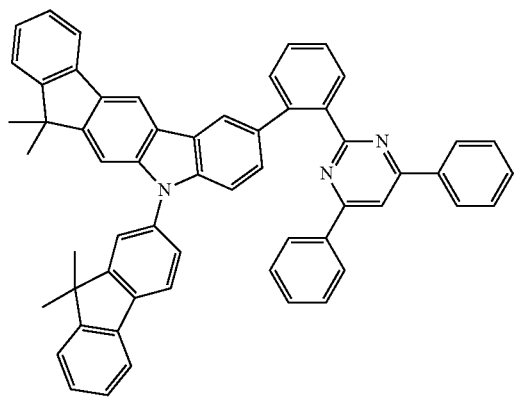
(64)
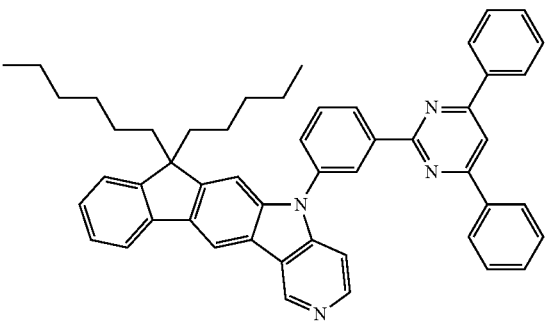

-continued
(65)
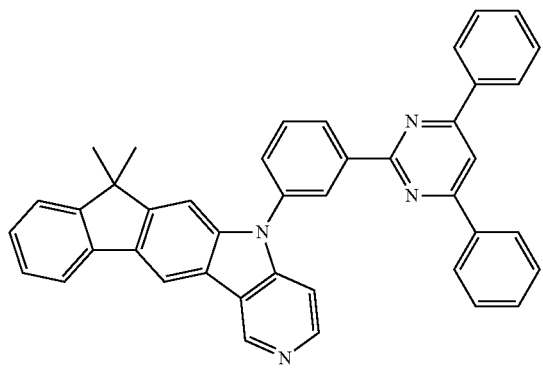
(66)
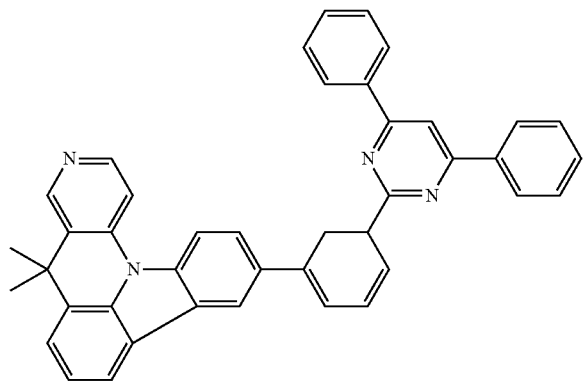
(67)
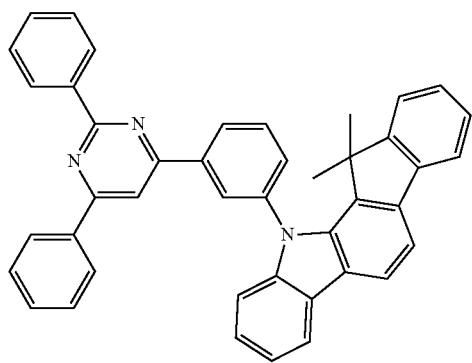
(68)
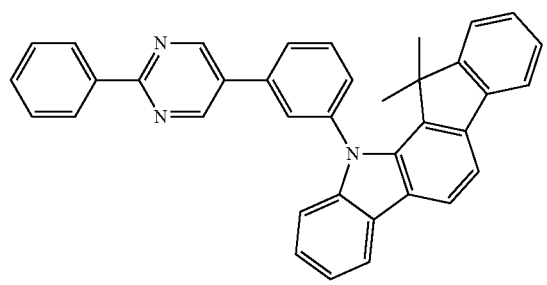
(69)
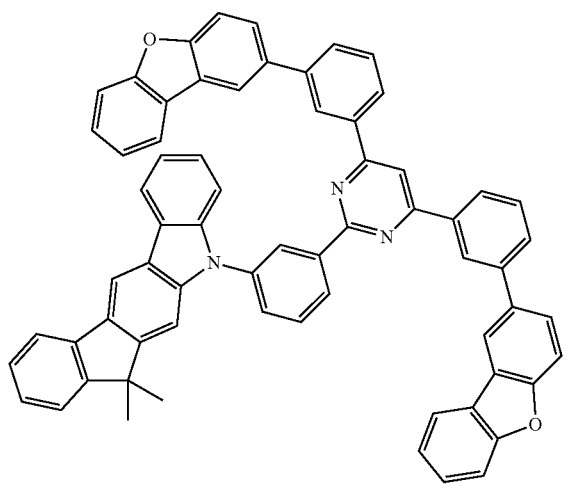
(70)
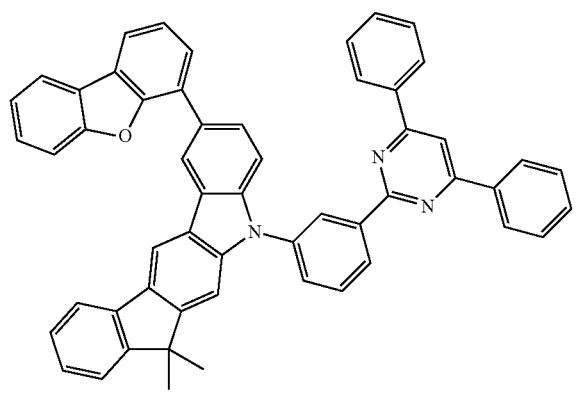

-continued
(71)
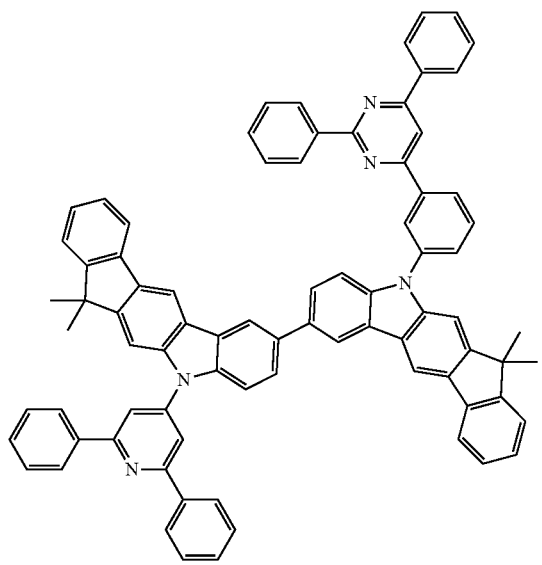
(72)
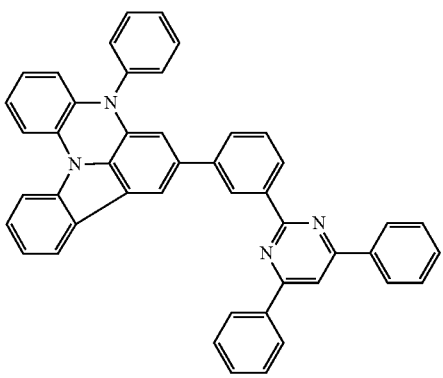
(73)
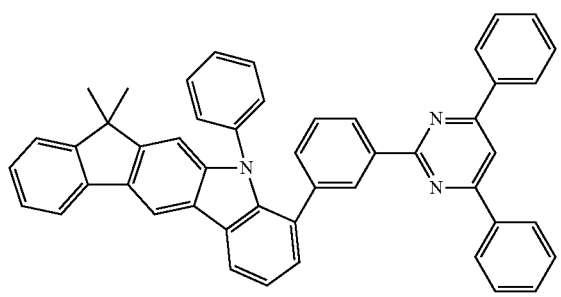
(74)
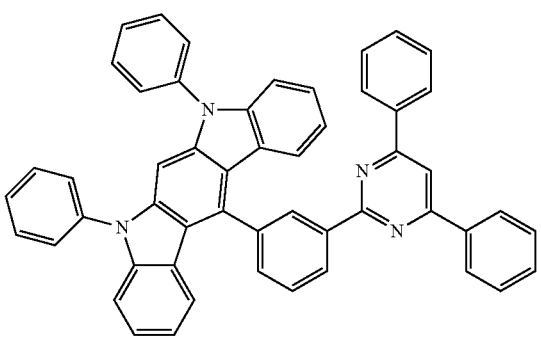
(75)
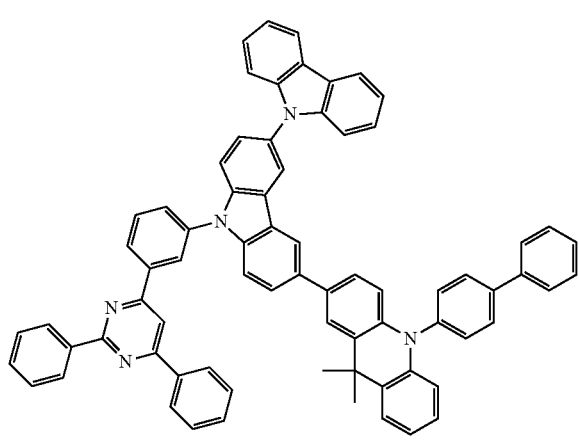
(76)
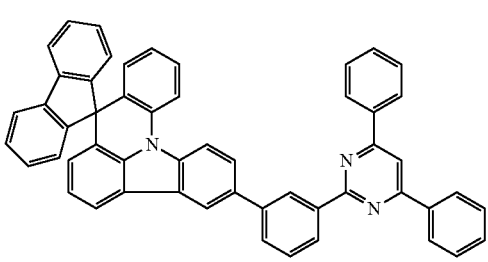

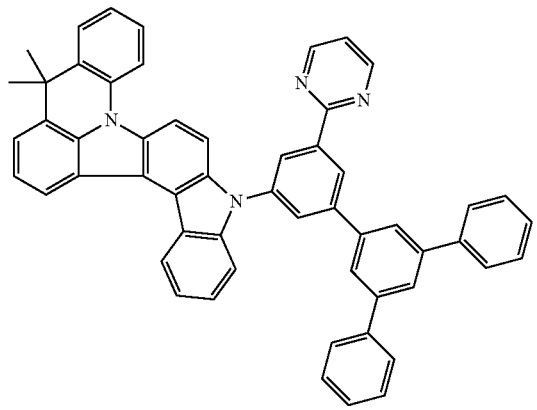
(77)

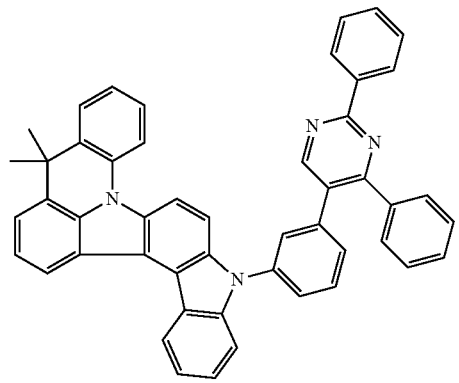
(78)

The synthesis of the compounds according to the invention starts, for example, from an optionally further-substituted bromophenylpyrimidine derivative, where, for compounds of the formula (1), the bromine is bonded in the meta-position to the pyrimidine and, for compounds of the formula (2), the bromine is bonded in the ortho-position to the pyrimidine. Instead of bromine, other reactive leaving groups, such as, for example, iodine, chlorine or triflate, can also be employed. This compound is then coupled to a corresponding carbazole derivative. Suitable for this purpose are, in particular, transition-metal-catalysed coupling reactions. If the phenyl-pyrimidine group is to be bonded directly to the nitrogen of the carbazole derivative, a palladium-catalysed Hartwig-Buchwald C—N coupling is particularly suitable for this purpose. If the phenylpyrimidine group is to be bonded to a carbon atom of the carbazole, palladium-catalysed C—C couplings, for example in accordance with Suzuki or in accordance with Stille, are particularly suitable for this purpose. For this purpose, the carbazole derivative must also contain a corresponding suitable leaving group, in particular chlorine, bromine, iodine, triflate or a boronic acid derivative, in particular boronic acid or a boronic acid ester. Furthermore, a corresponding boronic acid derivative, in particular a boronic acid or a boronic acid ester, is, for example, also suitable as starting material for this purpose instead of the bromophenylpyrimidine derivative.

The present invention therefore furthermore relates to a process for the preparation of a compound of the formula (1) or (2), comprising the reaction steps:
a) synthesis of an optionally substituted phenylpyrimidine derivative which contains a reactive leaving groups, in particular chlorine, bromine, iodine, triflate or a boronic acid derivative, in particular boronic acid or a boronic acid ester, on the phenyl group in the meta-position or in the ortho-position to the pyrimidine; and
b) coupling of this phenylpyrimidine derivative to a carbazole derivative.

The present invention furthermore relates to mixtures comprising at least one compound according to the invention and at least one further compound. The further compound can be, for example, a fluorescent or phosphorescent dopant if the compound according to the invention is used as matrix material. Suitable fluorescent and phosphorescent dopants are shown below in connection with the organic electroluminescent devices and are also preferred for the mixtures according to the invention.

For processing from solution or from the liquid phase, for example by spin coating or by printing processes, solutions or formulations of the compounds or mixtures according to the invention are necessary. It may be preferred to use mixtures of two or more solvents. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents.

The present invention therefore furthermore relates to a formulation, in particular a solution, a suspension or a miniemulsion, comprising at least one compound or mixture according to the invention and one or more solvents, in particular organic solvents. The way in which solutions of this type can be prepared is known to the person skilled in the art and described, for example, in WO 2002/072714, WO 2003/019694 and the literature cited therein.

The compounds and mixtures according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the above-mentioned compounds or mixtures according to the invention in an electronic device, in particular in an organic electroluminescent device.

The present invention again furthermore relates to an electronic device comprising at least one of the compounds or mixtures according to the invention mentioned above. The preferences stated above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells, organic optical detectors, organic photoreceptors, organic field-quench devices (O-FQDs), light-emitting electrochemical cells (LECs), organic laser diodes (O-lasers) and "organic plasmon emitting devices" (D. M. Koller et al., Nature Photonics 2008, 1-4), preferably organic electroluminescent devices (OLEDs, PLEDs), in particular phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport lay-ers, electron-injection layers, exciton-blocking layers, electron-blocking layers and/or charge-generation layers. It is likewise possible for inter-layers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emit-ting layers. Particular preference is given to systems having three emitting layers, where the three layers exhibit blue, green and orange or red emission (for the basic structure see, for example, WO 2005/011013). These can be fluorescent or phosphorescent emission layers or hybrid systems, in which fluorescent and phosphorescent emission layers are combined with one another.

The compound according to the invention in accordance with the embodiments indicated above can be employed in various layers, depending on the precise structure. Preference is given to an organic electroluminescent device comprising a compound of the formula (1) or (2) or the preferred embodiments indicated above as matrix material for fluorescent or phosphorescent emitters, in particular for phosphorescent emitters, and/or in a hole-blocking layer and/or in an electron-transport layer. The preferred embodiments indicated above also apply to the use of the materials in organic electronic devices.

In a preferred embodiment of the invention, the compound of the formula (1) or (2) or the preferred embodiments indicated above is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) or (2) or the preferred embodiments indicated above is employed as matrix material for an emitting compound in an emitting layer, it is preferably employed in combination with one or more phosphorescent materials (triplet emitters). Phosphorescence in the sense of this invention is taken to mean the luminescence from an excited state having relatively high spin multiplicity, i.e. a spin state >1, in particular from an excited triplet state. For the purposes of this application, all luminescent transition-metal complexes and luminescent lanthanide complexes, in particular all iridium, platinum and copper complexes, are to be regarded as phosphorescent compounds.

The mixture comprising the compound of the formula (1) or (2) or the preferred embodiments indicated above and the emitting compound comprises between 99 and 1% by vol., preferably between 98 and 10% by vol., particularly preferably between 97 and 60% by vol., in particular between 95 and 80% by vol., of the compound of the formula (1) or (2) or the preferred embodiments indicated above, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound of the formula (1) or (2) or the preferred embodiments indicated above as matrix material for a phosphorescent emitter in combination with a further matrix material. Particularly suitable matrix materials which can be employed in combination with the compounds of the formula (1) or (2) or the preferred embodiments indicated above are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 or WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, or bridged carbazole derivatives, for example in accordance with US 2009/0136779, WO 2010/050778, WO 2011/042107, WO 2011/060867 or WO 2011/088877. A further phosphorescent emitter which emits at shorter wavelength than the actual emitter may likewise be present in the mixture as co-host. Since the compounds according to the invention rathermore electron-transporting compounds, it is preferred for the further matrix component to rathermore have hole-transporting properties.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum. For the purposes of the present invention, all luminescent compounds which contain the above-mentioned metals are regarded as phosphorescent compounds.

Examples of the emitters described above are revealed by the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898. Furthermore suitable are the complexes in accordance with the unpublished applications EP 10006208.2 and DE 102010027317.1. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

In a further preferred embodiment of the invention, the compound of the formula (1) or (2) or the preferred embodiments indicated above is employed as electron-transport material in an electron-transport or electron-injection layer. The emitting layer here may be fluorescent or phosphorescent. If the compound is employed as electron-transport material, it may be preferred for it to be doped, for example with alkali-metal complexes, such as, for example, LiQ (lithium hydroxyquinolinate).

In still a further preferred embodiment of the invention, the compound of the formula (1) or (2) or the preferred embodiments indicated above is employed in a hole-blocking layer. A hole-blocking layer is taken to mean a layer which is directly adjacent to an emitting layer on the cathode side, in particular in a phosphorescent electroluminescent device.

It is furthermore possible to use the compound of the formula (1) or (2) or the preferred embodiments indicated above both in a hole-blocking layer or electron-transport layer and also as matrix in an emitting layer.

In the further layers of the organic electroluminescent device according to the invention, it is possible to use all materials as usually employed in accordance with the prior art. The person skilled in the art will therefore be able, without inventive step, to employ all materials known for organic electroluminescent devices in combination with the compounds of the formula (1) or (2) or the preferred embodiments indicated above.

Preference is furthermore given to an organic electroluminescent device, characterised in that one or more layers are coated by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower or higher, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, ink-jet printing, LITI (light induced thermal imaging, thermal transfer printing), screen printing, flexographic printing, offset printing or nozzle printing. Soluble compounds, which are obtained, for example, by suitable substitution, are necessary for this purpose. These processes are also particularly suitable for oligomers, dendrimers and polymers.

Also possible are hybrid processes, in which, for example, one or more layers are applied from solution and one or more further layers are applied by vapour deposition. Thus, it is possible, for example, to apply the emitting layer from solution and to apply the electron-transport layer by vapour deposition.

These processes are generally known to the person skilled in the art and can be applied by him without inventive step to organic electroluminescent devices comprising the compounds according to the invention.

The compounds according to the invention and the electroluminescent devices according to the invention are distinguished over the prior art by one or more of the following surprising advantages:

1. The compounds according to the invention, employed as matrix material for fluorescent or phosphorescent emitters, result in improved operating voltages at the same time as high efficiency and a long life-time. This applies, in particular, if the compounds are employed as matrix material for a phosphorescent emitter.
2. The compounds according to the invention are suitable, depending on the precise structure, not only as matrix for red- and green-phosphorescent compounds, but, in particular, also for blue-phosphorescent compounds.
3. Also on use as electron-transport material or as hole-blocking material, the compounds according to the invention result in very good proper-ties with respect to the operating voltage, the efficiency and the lifetime of organic electroluminescent devices.
4. The compounds according to the invention have a high glass-transition temperature and are therefore also suitable for applications in which relatively high thermal stresses are to be expected.

These above-mentioned advantages are not accompanied by an impairment in the other electronic properties.

The invention is explained in greater detail by the following examples, without wishing to restrict it thereby. The person skilled in the art will be able to carry out the invention throughout the range disclosed on the basis of the descriptions and will be able to prepare further compounds according to the invention without inventive step and use them in electronic devices or use the process according to the invention.

EXAMPLES

The following syntheses are carried out, unless indicated otherwise, under a protective-gas atmosphere in dried solvents. The compounds of the formula (1) or (2) according to the invention can be prepared by synthesis steps which are generally known to the person skilled in the art. The starting materials used can be, for example, 3-(bromophenyl)-1-phenyl-2-propen-1-one (*Chemistery & Biodiversity*, 2005, 2(12), 1656-1664), and 2,12-dimethyl-10-phenyl-10,12-dihydro-10-azaindeno[2,1-b]fluorene (in accordance with WO 2010/136109), 2-(3-bromophenyl)-4,6-diphenyl-pyrimidine, 4-(3-bromophenyl)-4,6-diphenylpyrimidine and 4-(3,5-dibromophenyl)-4,6-diphenylpyrimidine (WO 2005/085387) and 2-(3,5-dibromo-phenyl)-4,6-diphenylpyrimidine (US 2007/0141387). The terms in square brackets in the case of the compounds known from the literature are the CAS numbers.

Example 1

4-(2-Bromophenyl)-2,6-diphenylpyrimidine 3

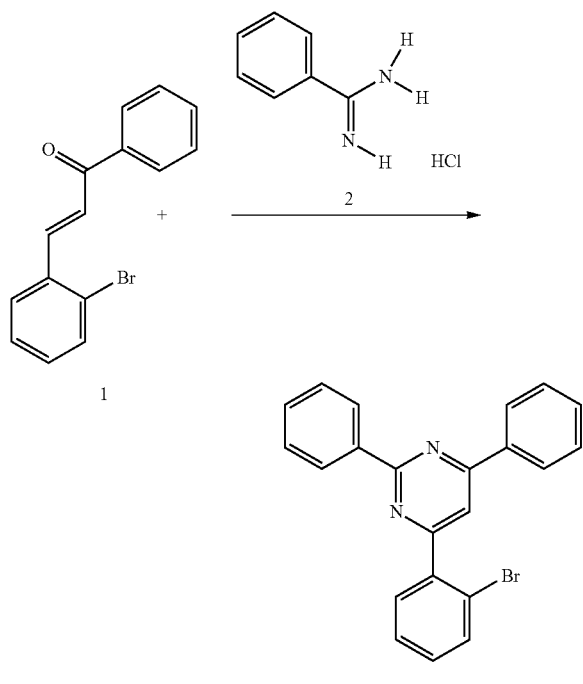

23 g (409 mmol) of potassium hydroxide are dissolved in 500 ml of ethanol, 40 g (255 mmol) of benzamide hydrochloride 2 and 129 g (452 mmol) of (3-(bromophenyl)-1-phenyl-2-propen-1-one 1, dissolved in 500 ml of ethanol, are added at room temperature, and the mixture is stirred under reflux for 3 h. After cooling to room temperature, the precipitated solid is filtered off with suction, washed with a little ethanol and dried, leaving 55 g (129 mmol), 50%, of the product in the form of colourless crystals.

Example 2

Compound 7

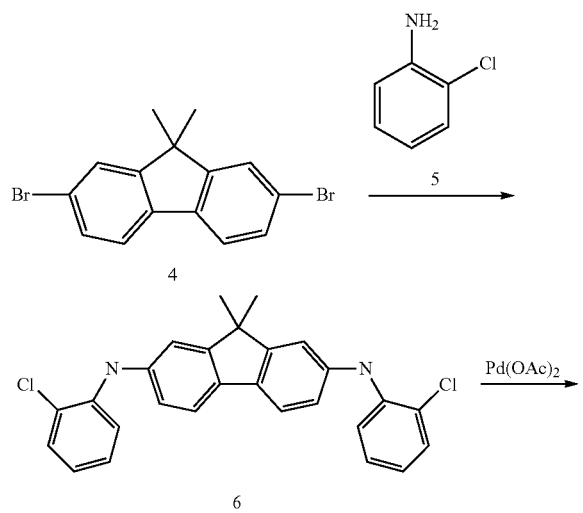

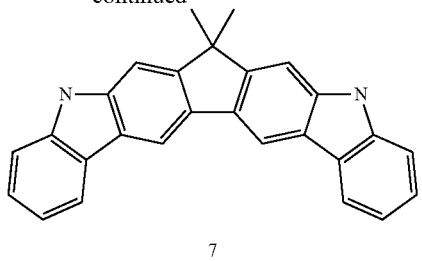

Step a: N,N'-Bis-(2-chlorophenyl)-9,9-dimethyl-9H-fluorene-2,7-diamine 6

40.48 g of 2,7-dibromo-9,9-dimethyl-9H-fluorene 4 (115 mmol), 21.4 g (21.5 ml) of aniline 5 (230 mmol), 1.91 g (3.5 mmol) of 1,1-bis(diphenyl-phosphino)ferrocene, 0.64 g of palladium(II) acetate (2.8 mmol) and 57.2 g of sodium tert-butoxide (598 mmol) are heated at the boil for 20 h in 1.3 l of toluene under a protective-gas atmosphere. The mixture is subsequently partitioned between toluene and water, the organic phase is washed three times with water, dried over $Na_2SO_4$ and evaporated in a rotary evaporator. The residue remaining, N,N'-bis-(2-chlorophenyl)-9,9-dimethyl-9H-fluorene-2,7-diamine 6, is recrystallised from toluene/ethyl acetate. The yield is 32.5 g (73 mmol, 63.5%).

Step b: Compound 7

300 ml of dioxane are added to 28.9 g of N,N'-bis-(2-chlorophenyl)-9,9-dimethyl-9H-fluorene-2,7-diamine 6 (65 mmol), 0.73 g of palladium(II) acetate (3.25 mmol) and 37.5 g of sodium tert-butoxide (390 mmol), 3.9 ml of 1 M solution of P(t-Bu)₃ in toluene (3.9 mmol), and the mixture is stirred at 105° C. under nitrogen for 48 h. 100 ml of dichloromethane and 0.1M $Na_2CO_3$ solution are then added. The mixture is partitioned between water and dichloromethane, the aqueous phase is extracted three times with dichloromethane, the combined organic phases are dried over $Na_2SO_4$ and evaporated in a rotary evaporator. The residue is recrystallised from toluene/heptane. The yield is 7.9 g (21.32 mmol, 57.3%).

Example 3

10,12-Dihydro-10-azaindeno[2,1-b]-12,12-spirofluorene 10

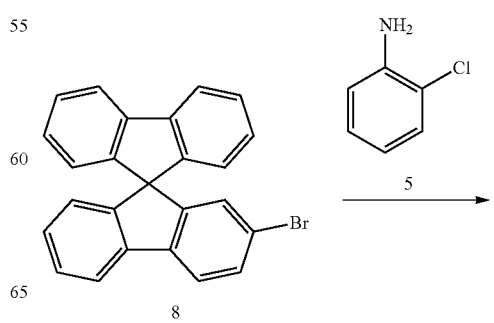

49
-continued

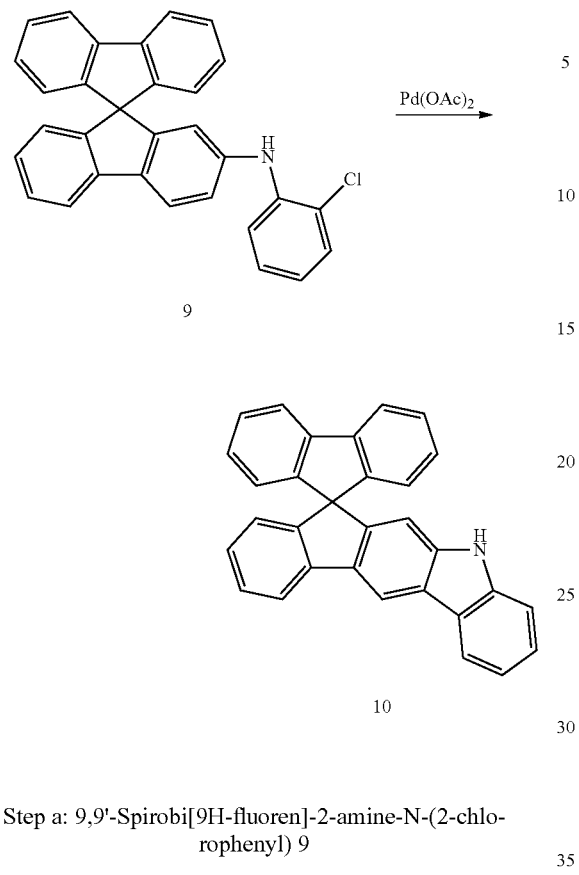

Step a: 9,9'-Spirobi[9H-fluoren]-2-amine-N-(2-chlorophenyl) 9

50 g of 2-bromo-9,9'-spirobifluorene 8 (126 mmol), 14 ml of aniline 5 (154 mmol), 1.1 g (2 mmol) of 1,1-bis(diphenylphosphino)ferrocenepalladium(II) dichloride complex with dichloromethane, 0.4 g of palladium(II) acetate (1.78 mmol) and 31 g of sodium tert-butoxide (323 mmol) are heated at the boil for 18 h in 1 l of toluene under a protective-gas atmosphere. The mixture is subsequently partitioned between toluene and water, the organic phase is washed three times with water, dried over $Na_2SO_4$ and evaporated in a rotary evaporator. The residue remaining is recrystallised from heptane/ethyl acetate. The yield is 50 g (114 mmol, 93%).

Step b: 10,12-Dihydro-10-azaindeno[2,1-b]-12,12-spirofluorene 10

300 ml of pivalic acid are added to 30 g of compound 9 (73.6 mmol), 1.6 g of palladium(II) acetate (7.4 mmol) and 1.6 g of potassium carbonate (11.4 mmol), and the mixture is stirred for 9 h at 120° C. under air. After this time, 1.6 g of palladium(II) acetate (7.4 mmol) are added, and the mixture is stirred at 120° C. for a further 9 h. 200 ml of dichloromethane and 0.1M $Na_2CO_3$ solution are then added. The mixture is partitioned between water and dichloromethane, the aqueous phase is extracted three times with dichloromethane, the combined organic phases are dried over $Na_2SO_4$ and evaporated in a rotary evaporator. The residue is recrystallised from toluene/heptane. The yield is 11.9 g (29.4 mmol, 40%).

50
Example 4

7-[3-(4,6-Diphenylpyrimidin-2-yl)phenyl]-12,12-dimethyl-10-phenyl-10,12-dihydro-10-azaindeno[2,1-b]fluorene 15

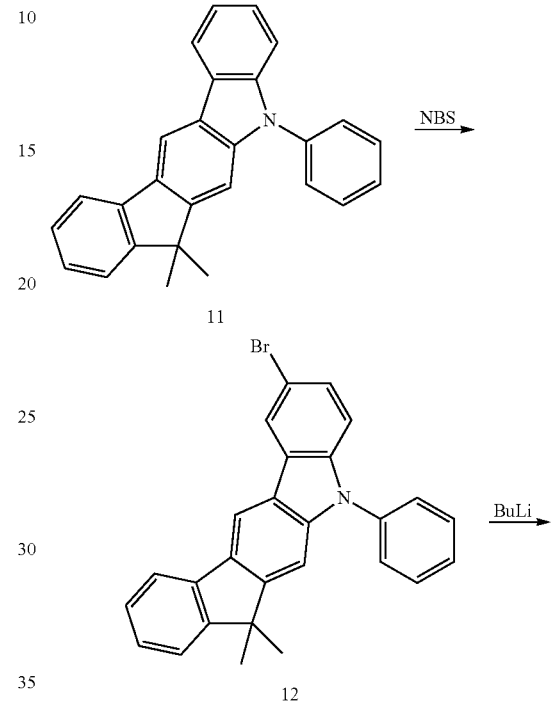

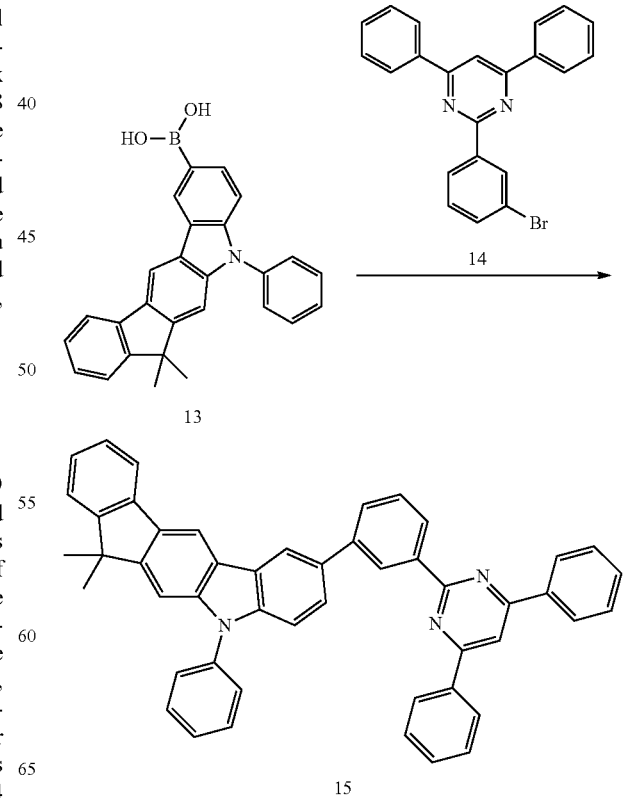

Step a: 7-Bromo-12,12-dimethyl-10-phenyl-10,12-dihydro-10-aza-indeno[2,1-b]fluorene 12

14.4 g (40.18 mmol) of 10-phenyl-4-yl-12,12-dimethyl-10,12-dihydro-10-azaindeno[2,1-b]fluorene 11 are suspended in 450 ml of acetonitrile, and 7.15 g (40.18 mmol) of N-bromosuccinimide are added in portions at −20° C. at such a rate that the reaction temperature does not exceed −20° C. The mixture is stirred for a further 18 h, during which the temperature is allowed to come to room temperature. The reaction mixture is subsequently evaporated in a rotary evaporator, dissolved in dichloromethane and washed with water. It is dried, evaporated and subsequently recrystallised from toluene to a purity of 99.3%, giving 9.6 g (55%) of the product as white solid.

Step b: 7-Borono12,12-dimethyl-10-phenyl-10,12-dihydro-10-aza-indeno[2,1-b]fluorene 13

22.3 g (51 mmol) of 7-bromo-12,12-dimethyl-10-phenyl-10,12-dihydro-10-azaindeno[2,1-b]fluorene 12 are dissolved in 600 ml of dry THF and cooled to −78° C. At this temperature, 26.2 ml (65.7 mmol/2.5 M in hexane) of n-BuLi are added over the course of about 5 min., and the mixture is subsequently stirred at −78° C. for a further 2.5 h. At this temperature, 7.3 ml (65.7 mmol) of trimethyl borate are added as rapidly as possible, and the reaction is allowed to come slowly to RT (about 18 h). The reaction solution is washed with water, and the precipitated solid and the organic phase are dried azeotropically with toluene. The crude product is washed by stir-ring with toluene/methylene chloride at about 40° C. and filtered off with suction, giving 16 g (82%) of the product as white solid.

Step c): 7-[3-(4,6-Diphenylpyrimidin-2-yl)phenyl]-12,12-dimethyl-10-phenyl-10,12-dihydro-10-azaindeno[2,1-b]fluorene 15

16 g (43.3 mmol) of 2-(3-bromophenyl)-4,6-diphenylpyrimidine 14 and 19.3 g (48 mmol) of 7-borono12,12-dimethyl-10-phenyl-10,12-dihydro-10-azaindeno[2,1-b]fluorene 13 are dissolved in 80 ml of toluene and degassed. 281 ml of a degassed 2M $K_2CO_3$ and 2.5 g (2.2 mmol) of $Pd(OAc)_2$ are added. The reaction mixture is subsequently stirred for 48 h at 80° C. under a protective-gas atmosphere. Additional toluene is added to the cooled solution, which is washed a number of times with water, dried and evaporated. The product is purified by column chromatography on silica gel with toluene/heptane (1:2). The purity is 99.9%. Yield: 22 g (31 mmol), 77% of theory.

The following compounds are obtained analogously:

| Ex. | Starting material 1 | Starting material 2 |
|---|---|---|
| 4a | | |
| 4b | | [864377-28-6] |

-continued

| Ex. | Product | Yield |
|---|---|---|
| 4a | | 68% |
| 4b | | 72% |

Example 5

10-[2-(2,6-Diphenylpyrimidin-4-yl)phenyl]-12,12-dimethyl-10,12-dihydro-10-azaindeno[2,1-b]fluorene 17

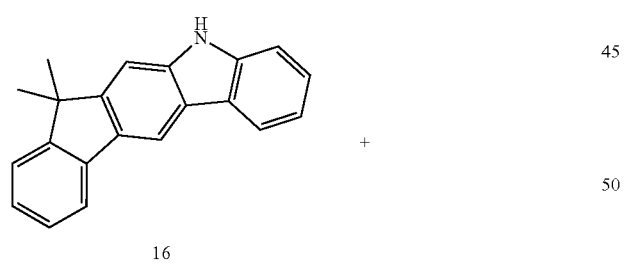

16

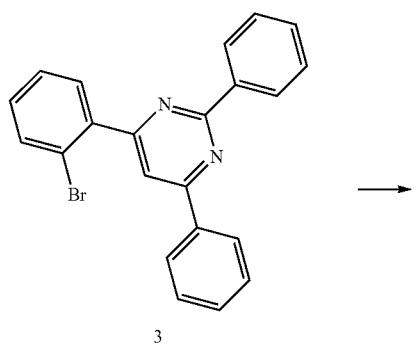

3

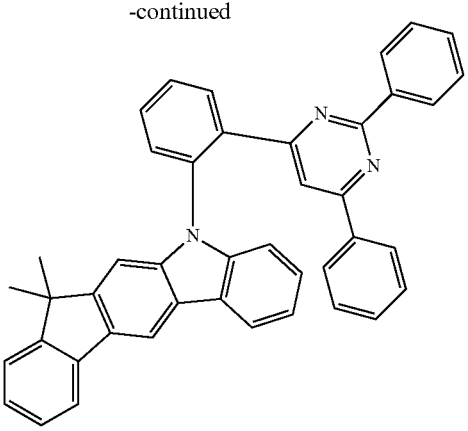

17

22 g (79.8 mmol) of 2,12-dimethyl-10-phenyl-10,12-dihydro-10-azaindeno-[2,1-b]fluorene 16, 34 g (87 mmol) of 4-(2-bromophenyl)-2,6-diphenyl-pyrimidine 3 and 15.9 ml (15.9 mmol) of 1 mol/l tri-tert-butylphosphine, 1.79 g (7.9 mmol) of palladium acetate are suspended in 120 ml of p-xylene under a protective gas. The reaction mixture is heated under reflux for 16 h. After cooling, the organic phase is separated off, washed three times with 200 ml of water and subsequently evaporated to dryness. The residue is extracted with hot toluene, recrystallised from toluene and finally sublimed in a high vacuum, the purity is 99.9%. Yield: 38 g (64 mmol), 80% of theory.

The following compounds are obtained analogously:

| Ex. | Starting material 1 | Starting material 2 |
|---|---|---|
| 5a | | [864377-22-0] |
| 5b | | [864377-28-6] |
| 5c | | [607740-08-9] |
| 5d | | [942132-67-4] |

-continued
| | | |
|---|---|---|
| 5e | 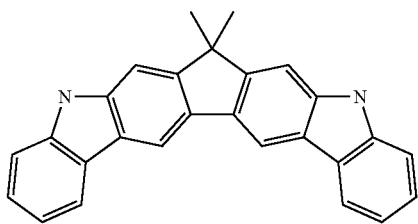 [SMILES: CC1(C)c2cc3[nH]c4ccccc4c3cc2-c2cc3c(cc21)[nH]c1ccccc13] | 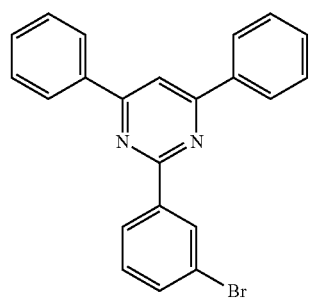 [SMILES: Brc1cccc(-c2nc(-c3ccccc3)cc(-c3ccccc3)n2)c1] |
| 5f | 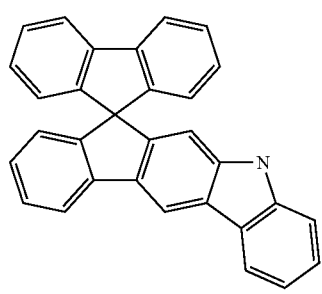 [SMILES: c1ccc2c(c1)-c1ccccc1C21c2ccccc2-c2cc3c(cc21)[nH]c1ccccc13] | 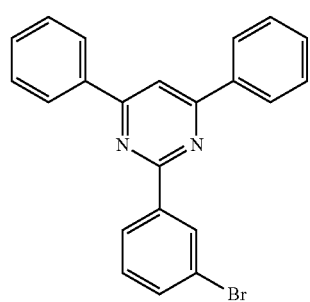 [SMILES: Brc1cccc(-c2nc(-c3ccccc3)cc(-c3ccccc3)n2)c1] |
| 5g | 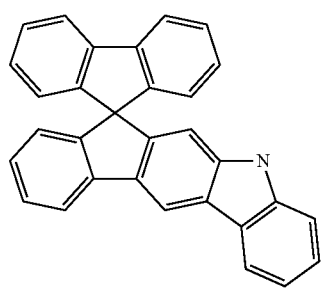 [SMILES: c1ccc2c(c1)-c1ccccc1C21c2ccccc2-c2cc3c(cc21)[nH]c1ccccc13] | 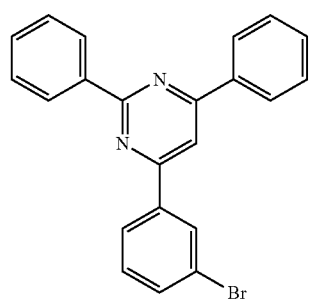 [SMILES: Brc1cccc(-c2cc(-c3ccccc3)nc(-c3ccccc3)n2)c1] |
| 5h | 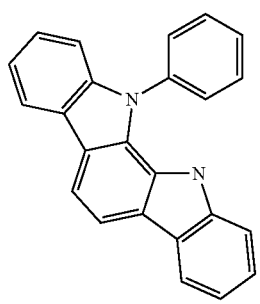 | 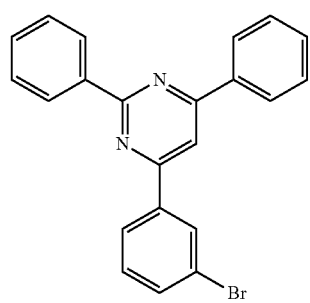 [SMILES: Brc1cccc(-c2cc(-c3ccccc3)nc(-c3ccccc3)n2)c1] |
| [1024598-06-8] | | |

-continued
| Ex. | Product | Yield |
|---|---|---|
| 5a | 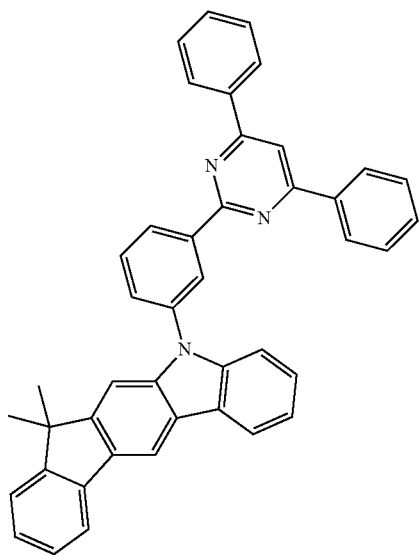 [SMILES: CC1(C)c2ccccc2-c2cc3c4ccccc4n(-c4cccc(-c5nc(-c6ccccc6)cc(-c6ccccc6)n5)c4)c3cc21] | 87% |
| 5b | 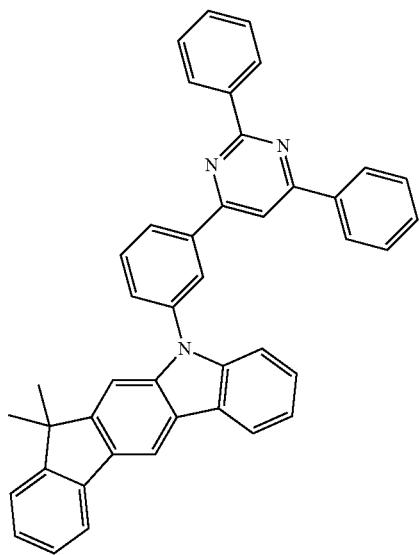 [SMILES: CC1(C)c2ccccc2-c2cc3c4ccccc4n(-c4cccc(-c5cc(-c6ccccc6)nc(-c6ccccc6)n5)c4)c3cc21] | 82% |

| | | |
|---|---|---|
| 5c | 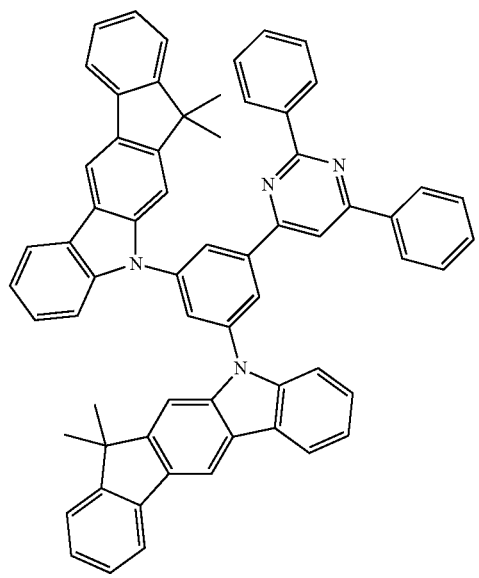 [SMILES: CC1(C)c2ccccc2-c2cc3c4ccccc4n(-c4cc(-c5cc(-c6ccccc6)nc(-c6ccccc6)n5)cc(-n5c6ccccc6c6cc7c(cc65)C(C)(C)c5ccccc5-7)c4)c3cc21] | 73% |
| 5d | 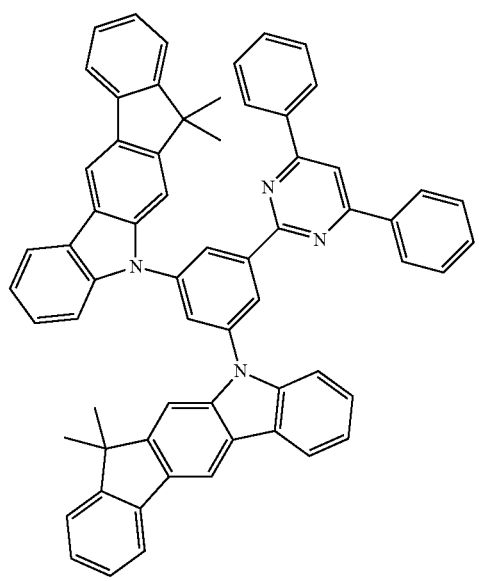 [SMILES: CC1(C)c2ccccc2-c2cc3c4ccccc4n(-c4cc(-c5nc(-c6ccccc6)cc(-c6ccccc6)n5)cc(-n5c6ccccc6c6cc7c(cc65)C(C)(C)c5ccccc5-7)c4)c3cc21] | 71% |
| 5e | 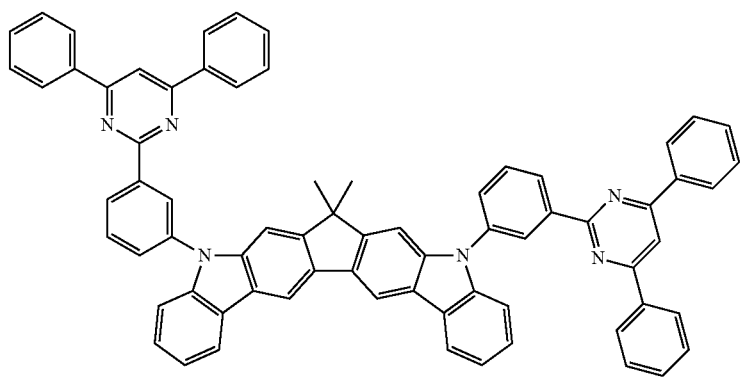 [SMILES: CC1(C)c2cc3c(cc2-c2cc4c5ccccc5n(-c5cccc(-c6nc(-c7ccccc7)cc(-c7ccccc7)n6)c5)c4cc21)c1ccccc1n3-c1cccc(-c2nc(-c3ccccc3)cc(-c3ccccc3)n2)c1] | 56% |

| | | |
|---|---|---|
| 5f | 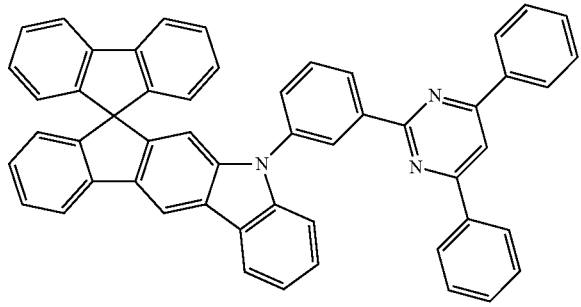 [SMILES: c1ccc(-c2cc(-c3ccccc3)nc(-c3cccc(-n4c5ccccc5c5cc6c(cc54)C4(c5ccccc5-c5ccccc54)c4ccccc4-6)c3)n2)cc1] | 79% |
| 5g | 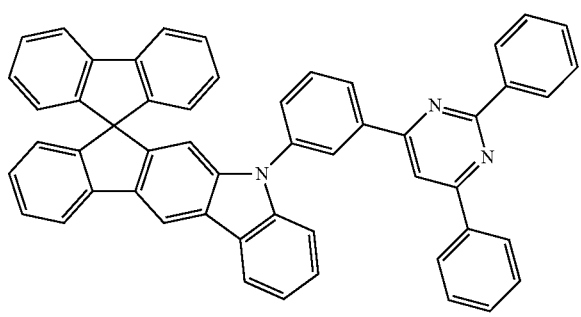 [SMILES: c1ccc(-c2cc(-c3cccc(-n4c5ccccc5c5cc6c(cc54)C4(c5ccccc5-c5ccccc54)c4ccccc4-6)c3)nc(-c3ccccc3)n2)cc1] | 83% |
| 5h | 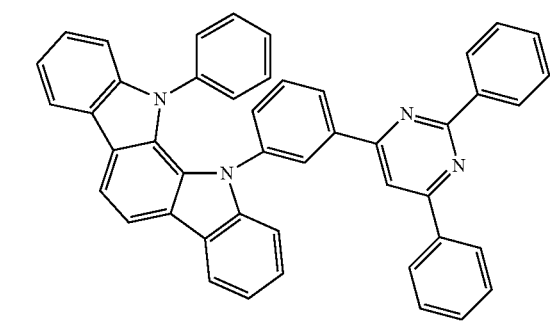 [SMILES: c1ccc(-c2cc(-c3cccc(-n4c5ccccc5c5ccc6c7ccccc7n(-c7ccccc7)c6c54)c3)nc(-c3ccccc3)n2)cc1] | 55% |
Example 6
Compound 21
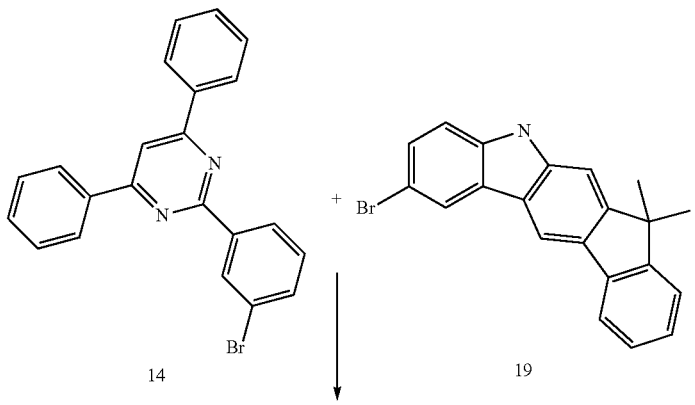

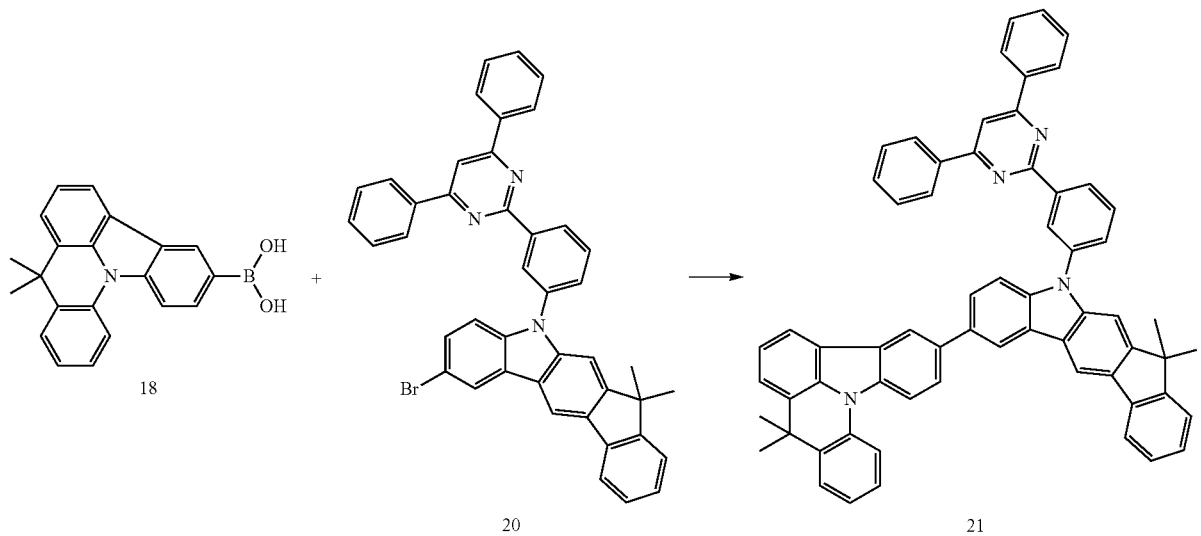

Step a: 7-Bromo-10-[3-(4,6-diphenylpyrimidin-2-yl)phenyl]-12,12-dimethyl-10,12-dihydro-10-azaindeno[2,1-b]fluorene 20

19.55 g (53.97 mmol) of 7-bromo-12,12-dimethyl-10,12-dihydro-10-aza-indeno[2,1-b]fluorene 19, 22.99 g (59.37 mmol) of 2-(3-bromophenyl)-4,6-diphenylpyrimidine 14 and 15.84 g (164.81 mmol) of NaOtBu are suspended in 820 ml of p-xylene. 245.0 mg (1.09 mmol) of Pd(OAc)$_2$ and 3.3 ml of a 1M tri-tert-butylphosphine solution are added to this suspension. The reaction mixture is heated under reflux for 19 h. After cooling, the organic phase is separated off, washed three times with 100 ml of water and subsequently evaporated to dryness. The residue is extracted with hot tolu-ene, recrystallised from toluene. The yield is 21.65 g (65%).

Step b: Compound 21

21.65 g (32.38 mmol) of 7-bromo-10-[3-(4,6-diphenylpyrimidin-2-yl)phenyl]-12,12-dimethyl-10,12-dihydro-10-azaindeno[2,1-b]fluorene 20, 11.65 g (36.62 mmol) of compound 18 and 3.82 g of sodium carbonate are suspended in 1200 ml of dioxane, 1200 ml of toluene and 500 ml of water. 1.92 g (1.66 mmol) of Pd(PPh$_3$)$_4$ are added to this suspension. The reaction mixture is heated under reflux for 5 h. After cooling, the precipitated solid is filtered off with suction, washed with water and ethanol and dried. The residue is extracted with hot toluene and recrystallised from toluene. The yield is 14.1 g (50%)

Example 7

Compound 24

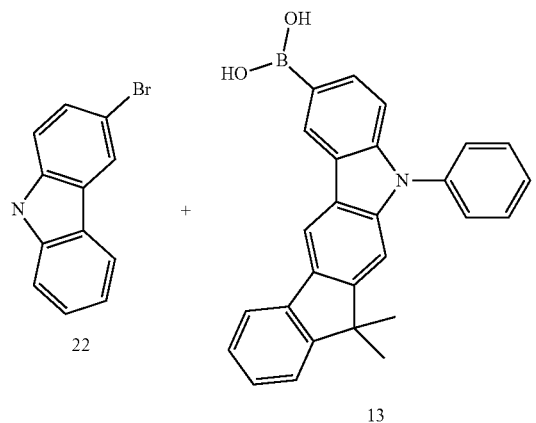

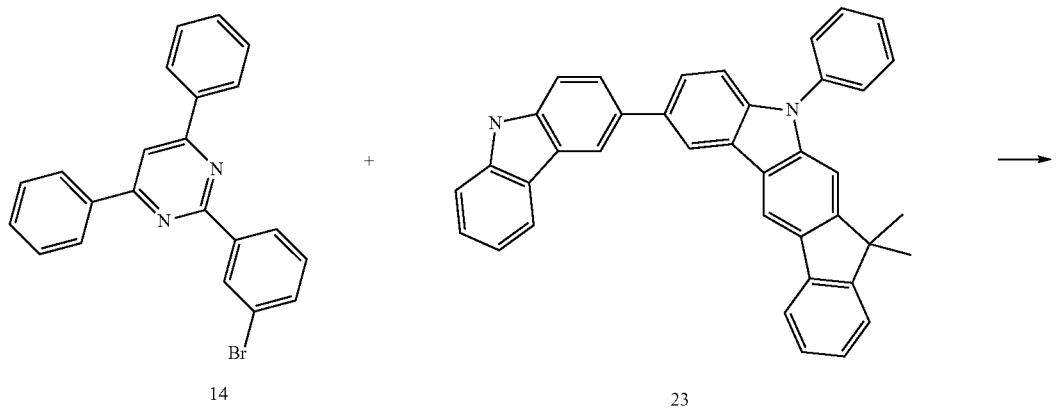

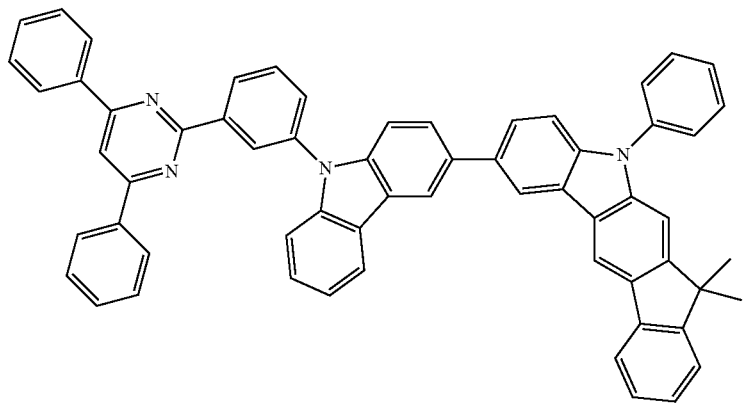

Step a: 7-(9H-Carbazol-3-yl)-12,12-dimethyl-10-phenyl-10,12-dihydro-10-azaindeno[2,1-b]fluorene 23

14.07 g (57.18 mmol) of 3-bromo-9H-carbazole 22, 25.37 g (62.90 mmol) of compound 13 and 6.75 g of sodium carbonate are suspended in 1800 ml of dioxane, 1800 ml of toluene and 750 ml of water. 3.38 g (2.93 mmol) of Pd(PPh$_3$)$_4$ are added to this suspension. The reaction mixture is heated under reflux for 5 h. After cooling, the precipitated solid is filtered off with suction, washed with water and ethanol and dried. The residue is extracted with hot toluene and recrystallised from toluene. The yield is 19.5 g (65%).

Step b: 7-{9-[3-(4,6-Diphenylpyrimidin-2-yl)phenyl]-9H-carbazol-3-yl}-12,12-dimethyl-10-phenyl-10,12-dihydro-10-azaindeno[2,1-b]fluorene 24

19.50 g (37.17 mmol) of 7-(9H-carbazol-3-yl)-12,12-dimethyl-10-phenyl-10,12-dihydro-10-azaindeno[2,1-b]fluorene 23, 15.83 g (40.88 mmol) of 2-(3-bromophenyl)-4,6-diphenylpyrimidine 14 and 10.91 g (113.50 mmol) of NaOtBu are suspended in 600 ml of p-xylene. 168.73 mg (0.75 mmol) of Pd(OAc)$_2$ and 2.3 ml of a 1M tri-tert-butylphosphine solution are added to this suspension. The reaction mixture is heated under reflux for 19 h. After cooling, the organic phase is separated off, washed three times with 100 ml of water and subsequently evaporated to dryness. The residue is extracted with hot toluene, recrystallised from toluene and finally sublimed in a high vacuum. The yield is 15.44 g (50%).

Example 8

Compound 27

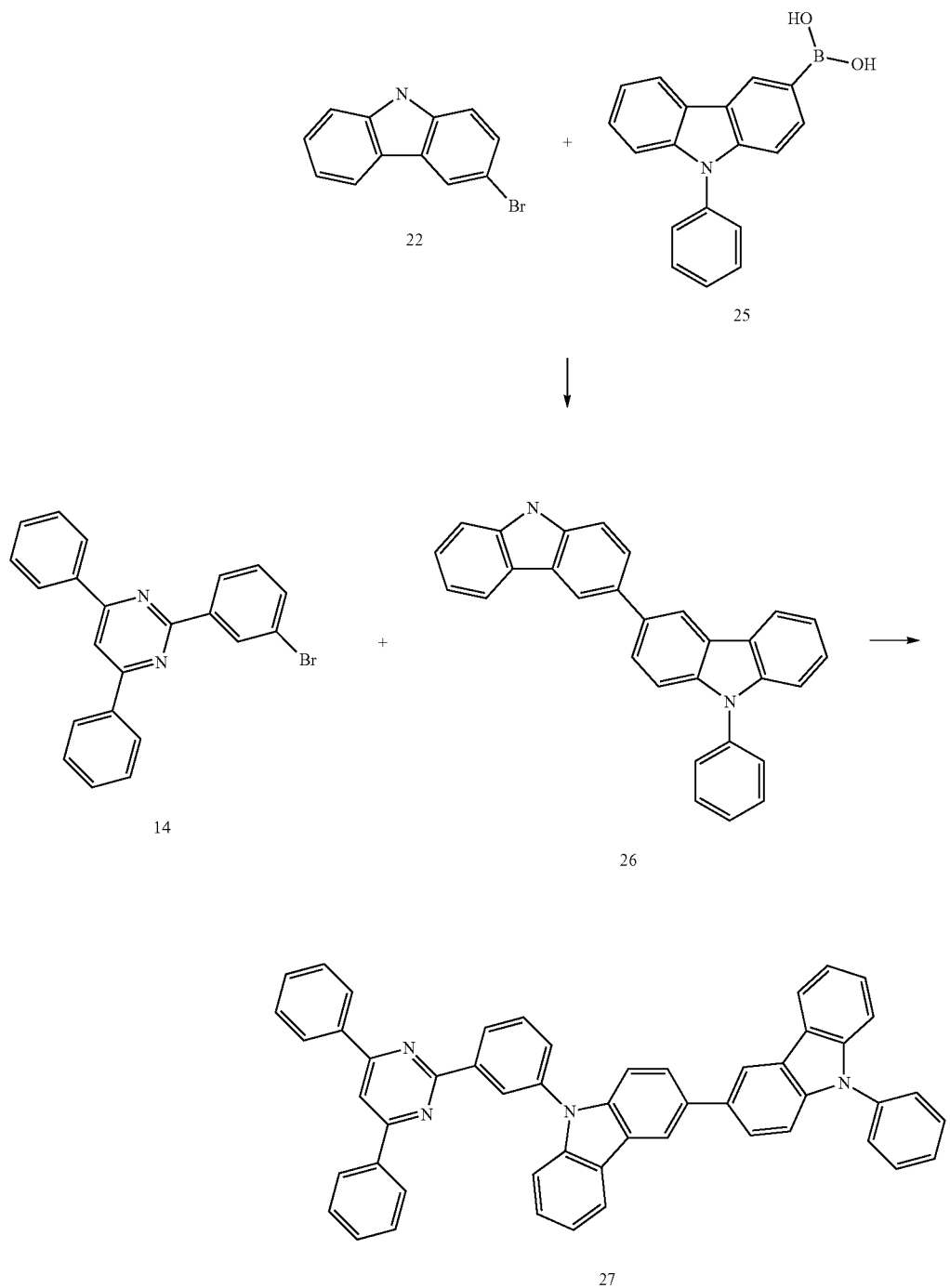

Step a: 9-Phenyl-9H,9'H-[3,3']bicarbazolyl 26

24.10 g (97.92 mmol) of 3-bromo-9H-carbazole 22, 30.93 g (107.71 mmol) of compound 25 and 11.56 g of sodium carbonate are suspended in 2500 ml of dioxane, 2500 ml of toluene and 1000 ml of water. 5.79 g (5.01 mmol) of Pd(PPh$_3$)$_4$ are added to this suspension. The reaction mixture is heated under reflux for 5 h. After cooling, the precipitated solid is filtered off with suction, washed with water and ethanol and dried. The residue is extracted with hot toluene and recrystallised from toluene. The yield is 22.0 g (55%).

Step b: 9-[3-(4,6-Diphenylpyrimidin-2-yl)phenyl]-9'-phenyl-9H,9'H-[3,3]bicarbazolyl 27

22.00 g (53.86 mmol) of 9-phenyl-9H,9'H-[3,3']bicarbazolyl 26, 22.93 g (59.24 mmol) of 2-(3-bromophenyl)-4,6-diphenylpyrimidine 14 and 15.81 g (164.47 mmol) of NaOtBu are suspended in 820 ml of p-xylene. 244.79 mg (1.09 mmol) of Pd(OAc)$_2$ and 3.3 ml of a 1M tri-tert-butylphosphine solution are added to this suspension. The reaction mixture is heated under reflux for 19 h. After cooling, the organic phase is separated off, washed three times with 100 ml of water and subsequently evaporated to dryness. The residue is extracted with hot toluene, recrystallised from toluene and finally sublimed in a high vacuum. The yield is 23.10 g (60%).

Example 9

Compound 30

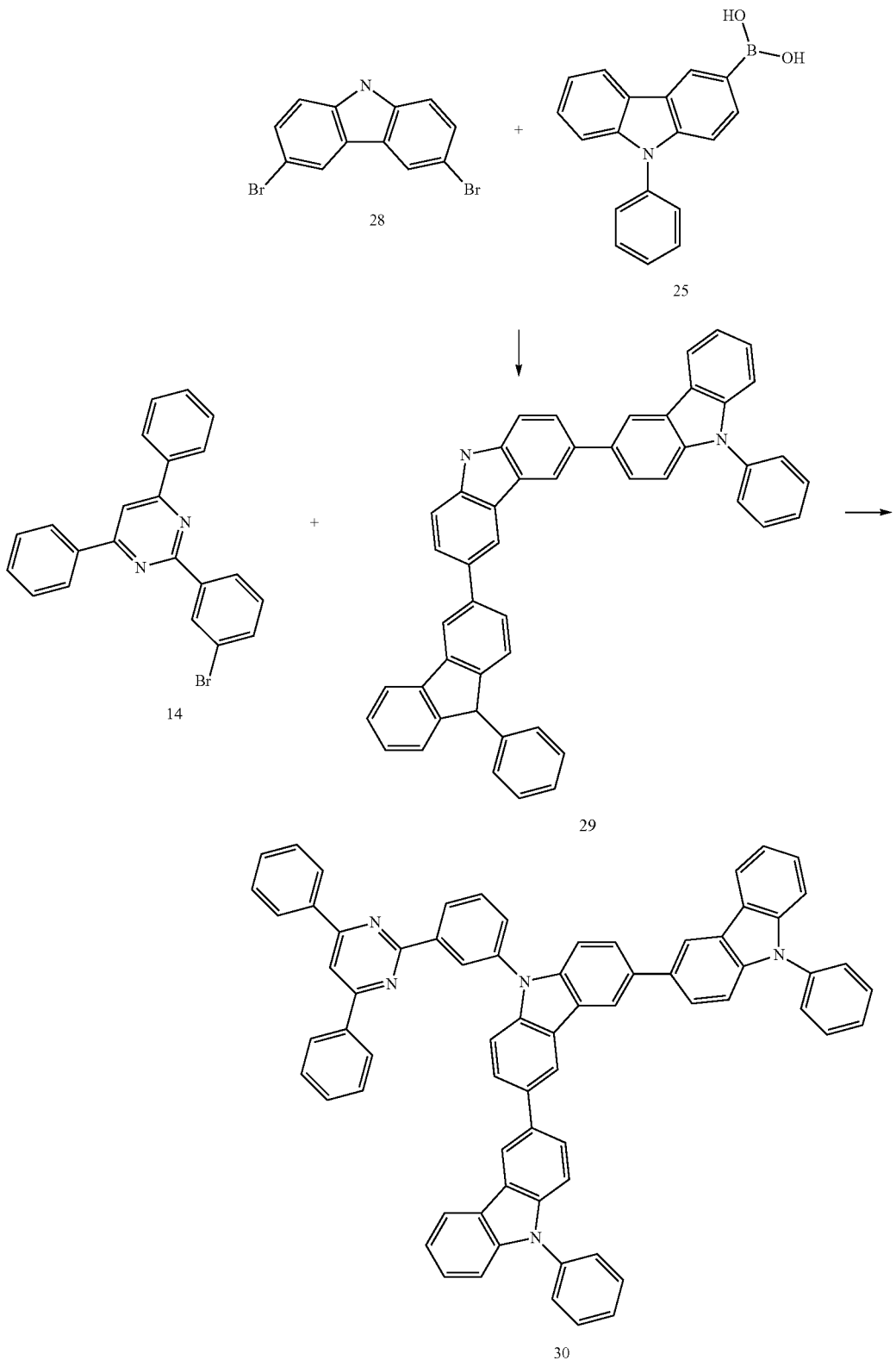

Step a: 9,9''-Diphenyl-9H,9'H,9''H-[3,3';6',3'']tercarbazole 29

22.51 g (69.25 mmol) of 3,6-dibromo-9H-carbazole 28, 43.75 g (152.36 mmol) of compound 25 and 8.17 g of sodium carbonate are suspended in 2000 ml of dioxane, 2000 ml of toluene and 900 ml of water. 4.10 g (3.55 mmol) of Pd(PPh$_3$)$_4$ are added to this suspension. The reaction mixture is heated under reflux for 5 h. After cooling, the precipitated solid is filtered off with suction, washed with water and ethanol and dried. The residue is extracted with hot toluene and recrystallised from toluene. The yield is 28.8 g (64%).

Step b: 9'-[3-(4,6-Diphenylpyrimidin-2-yl)phenyl]-9,9''-diphenyl-9H,9'H,9''H-[3,3';6',3'']tercarbazole 30

28.8 g (44.32 mmol) of 9,9''-diphenyl-9H,9'H,9''H-[3,3';6',3'']tercarbazole 29, 18.88 g (48.76 mmol) of 2-(3-bromophenyl)-4,6-diphenylpyrimidine 14 and 13.01 g (135.35 mmol) of NaOtBu are suspended in 820 ml of p-xylene. 201.21 mg (0.90 mmol) of Pd(OAc)$_2$ and 2.7 ml of a 1M tri-tert-butylphosphine solution are added to this suspension. The reaction mixture is heated under reflux for 19 h. After cooling, the organic phase is separated off, washed three times with 100 ml of water and subsequently evaporated to dryness. The residue is extracted with hot toluene, recrystallised from toluene and finally sublimed in a high vacuum. The yield is 23.3 g (55%).

Example 10

Production of OLEDs

OLEDs comprising comparative materials or materials according to the invention are produced by a general process in accordance with WO 2004/058911, which is adapted to the circumstances described here (layer-thickness variation, materials).

The data for various OLEDs are presented in Examples V1-E17 below (see Tables 1 and 2). Glass plates coated with structured ITO (indium tin oxide) in a thickness of 150 nm are coated with 20 nm of PEDOT (poly-(3,4-ethylenedioxythiophene), applied by spin coating from water; purchased from H. C. Starck, Goslar, Germany) for improved processing. These coated glass plates form the substrates to which the OLEDs are applied. The OLEDs have in principle the following layer structure: substrate/hole-transport layer (HTL)/interlayer (IL)/electron-blocking layer (EBL)/emission layer (EML)/optional hole-blocking layer (HBL)/electron-transport layer (ETL) and finally a cathode. The cathode is formed by an aluminium cathode with a thickness of 100 nm. The precise structure of the OLEDs is shown in Table 1. The materials used for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or materials in a certain proportion by volume by co-evaporation. An expression such as IC1:TEG1 (90%:10%) here means that material IC1 is present in the layer in a proportion by volume of 90% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines), assuming Lambert emission characteristics, and the life-time are determined. The electroluminescence spectra are determined at a luminous density of 1000 cd/m$^2$, and the CIE 1931 x and y colour coordinates are calculated therefrom. The expression U1000 in Table 2 denotes the voltage required for a luminous density of 1000 cd/m$^2$. CE1000 and PE1000 denote the current and power efficiencies achieved at 1000 cd/m$^2$. Finally, EQE1000 is the external quantum efficiency at an operating luminous density of 1000 cd/m$^2$. The lifetime LT defines the time after which the luminous density on operation at constant current drops from the initial luminous density L0 to a certain proportion L1. A specification of L0=4000 cd/m$^2$ and L1=80% in Table 2 means that the lifetime indicated in column LT corresponds to the time after which the initial luminous density of the corresponding OLED drops from 4000 cd/m$^2$ to 3200 cd/m$^2$. The values for the lifetime can be converted to a figure for other initial luminous densities with the aid of conversion formulae known to the person skilled in the art. The lifetime for an initial luminous density of 1000 cd/m$^2$ is the value usually quoted in this case.

The data for the various OLEDs are summarised in Table 2. Examples V1-112 are comparative examples, Examples E1-Fehler! Verweisquelle konnte nicht gefunden werden. show data for OLEDs comprising materials according to the invention.

Some of the examples are explained in greater detail below in order to illustrate the advantages of the compounds according to the invention. However, it should be pointed out that this only represents a selection of the data shown in Table 2. As can be seen from the table, significant improvements compared with the comparative compounds can also be achieved on use of the compounds according to the invention that are not described in greater detail, in some cases in all parameters, in some cases only an improvement in efficiency or voltage or lifetime is observed. How-ever, even the improvement of one of the said parameters represents a significant advance, since different applications require optimisation with respect to different parameters.

Use of Compounds According to the Invention as Matrix Materials in Phosphorescent OLEDs The advantages of the compounds according to the invention can be illustrated with reference to compounds H4-H6 compared with IC1-IC3 and IC5. The comparative materials are indenocarbazole derivatives which contain triazine bonded to the nitrogen via a meta-linked phenyl group (IC2) or directly (IC1) or which contain pyrimidine bonded to the nitrogen via a para-linked phenyl group (IC5) or directly (IC3). OLEDs comprising these comparative materials already have good values: a minimum voltage of 3.4 V, an external quantum efficiency of up to 15.9%, a maximum power efficiency of 50 lm/W and a maximum lifetime of 440 h are obtained (V4, V3). These values can be improved further with the comparable compounds H4-H6 according to the invention, voltages of 3.2 V, 16.3% EQE, 57 lm/W and a lifetime of 490 h (E2) are obtained. All of compounds H4-H6 according to the invention exhibit an improved voltage compared with the comparative materials.

A similar picture arises on comparison of comparative compounds IC6-IC9 with materials H12 (comparison with IC6 and IC7, Examples V5, V6, E4, E5), H1-H3 (comparison with IC8, Examples V7, E6-E8), and H10, H11 (comparison with IC9, Examples V8, E9, E10) according to the invention.

The examples mentioned show that significant advantages arise on linking of carbazole derivatives to a pyrimidine via an ortho- or meta-linked phenyl group compared with carbazole derivatives containing
- a pyrimidine or triazine bonded directly to the nitrogen,
- a triazine which is bonded via a meta-linked phenyl group,
- a pyrimidine which is bonded via a para-linked phenyl group.

Furthermore, a comparison of comparative compounds PyCbz1-PyCbz3 with materials H6 (comparison with PyCbz1, Examples V9, E3), H7, H8 (comparison with PyCbz2, Examples V10, E11, E12) and H15 (comparison with PyCbz3, Examples V11, E16) according to the invention shows that compounds according to the invention which contain a carbazole derivative having at least two bridges offer significant advantages compared with similar materials which comprise pure carbazoles.

Further materials according to the invention (H9, H13, H15, H16) likewise provide significant improvements compared with the comparative materials. In particular, a power efficiency of 58 lm/W is obtained with compound H13, which is more than 10% higher than in the case of the best comparative material in the same device structure (V1). With respect to the lifetime, an improvement of more than 30% is obtained with the same material (Examples V1, E14). An extraordinarily low voltage of 3.0 V is obtained with compound H9 (Example E13).

On use as matrix materials in phosphorescent OLEDs, the materials according to the invention thus give rise to significant improvements compared with the prior art in all parameters, especially with respect to power efficiency and lifetime. The considerable improvement in the power efficiency on use of materials according to the invention can be attributed, in particular, to the significant improvement in the operating voltage.

TABLE 1

Structure of the OLEDs

| Ex. | HTL Thickness | IL Thickness | EBL Thickness | EML Thickness | HBL Thickness | ETL Thickness |
|---|---|---|---|---|---|---|
| V1 | SpA1 70 nm | HATCN 5 nm | BPA1 90 nm | IC1:TEG1 (90%:10%) 30 nm | IC1 10 nm | ST1:LiQ (50%:50%) 30 nm |
| V2 | SpA1 70 nm | HATCN 5 nm | BPA1 90 nm | IC2:TEG1 (90%:10%) 30 nm | IC1 10 nm | ST1:LiQ (50%:50%) 30 nm |
| V3 | SpA1 70 nm | HATCN 5 nm | BPA1 90 nm | IC3:TEG1 (90%:10%) 30 nm | IC1 10 nm | ST1:LiQ (50%:50%) 30 nm |
| V4 | SpA1 70 nm | HATCN 5 nm | BPA1 90 nm | IC5:TEG1 (90%:10%) 30 nm | IC1 10 nm | ST1:LiQ (50%:50%) 30 nm |
| V5 | SpA1 70 nm | HATCN 5 nm | BPA1 90 nm | IC6:TEG1 (85%:15%) 30 nm | IC1 10 nm | ST2:LiQ (50%:50%) 30 nm |
| V6 | SpA1 70 nm | HATCN 5 nm | BPA1 90 nm | IC7:TEG1 (90%:10%) 30 nm | — | ST2:LiQ (50%:50%) 40 nm |
| V7 | SPA1 70 nm | HATCN 5 nm | BPA1 90 nm | IC8:TEG1 (90%:10%) 30 nm | — | ETM1:LiQ (50%:50%) 40 nm |
| V8 | SPA1 70 nm | HATCN 5 nm | BPA1 90 nm | IC9:TEG1 (90%:10%) 30 nm | — | ETM1:LiQ (50%:50%) 40 nm |
| V9 | SpA1 70 nm | HATCN 5 nm | BPA1 90 nm | PyCbz1:TEG1 (90%:10%) 30 nm | IC1 10 nm | ST1:LiQ (50%:50%) 30 nm |
| V10 | SpA1 70 nm | HATCN 5 nm | BPA1 90 nm | PyCbz2:TEG1 (90%:10%) 30 nm | IC1 10 nm | ST1:LiQ (50%:50%) 30 nm |
| V11 | SpA1 70 nm | HATCN 5 nm | BPA1 90 nm | PyCbz3:TEG1 (90%:10%)30 nm | IC1 10 nm | ST1:LiQ (50%:50%) 30 nm |
| E1 | SpA1 70 nm | HATCN 5 nm | BPA1 90 nm | H4:TEG1 (90%:10%) 30 nm | IC1 10 nm | ST1:LiQ (50%:50%) 30 nm |
| E2 | SpA1 70 nm | HATCN 5 nm | BPA1 90 nm | H5:TEG1 (90%:10%) 30 nm | IC1 10 nm | ST1:LiQ (50%:50%) 30 nm |
| E3 | SpA1 70 nm | HATCN 5 nm | BPA1 90 nm | H6:TEG1 (90%:10%) 30 nm | IC1 10 nm | ST1:LiQ (50%:50%) 30 nm |
| E4 | SpA1 70 nm | HATCN 5 nm | BPA1 90 nm | H12:TEG1 (85%:15%) 30 nm | IC1 10 nm | ST2:LiQ (50%:50%) 30 nm |
| E5 | SpA1 70 nm | HATCN 5 nm | BPA1 90 nm | H12:TEG1 (90%:10%) 30 nm | — | ST2:LiQ (50%:50%) 40 nm |
| E6 | SPA1 70 nm | HATCN 5 nm | BPA1 90 nm | H1:TEG1 (90%:10%) 30 nm | — | ETM1:LiQ (50%:50%) 40 nm |
| E7 | SPA1 70 nm | HATCN 5 nm | BPA1 90 nm | H2:TEG1 (90%:10%) 30 nm | — | ETM1:LiQ (50%:50%) 40 nm |
| E8 | SPA1 70 nm | HATCN 5 nm | BPA1 90 nm | H3:TEG1 (90%:10%) 30 nm | — | ETM1:LiQ (50%:50%) 40 nm |
| E9 | SPA1 70 nm | HATCN 5 nm | BPA1 90 nm | H10:TEG1 (90%:10%) 30 nm | — | ETM1:LiQ (50%:50%) 40 nm |
| E10 | SPA1 70 nm | HATCN 5 nm | BPA1 90 nm | H11:TEG1 (90%:10%) 30 nm | — | ETM1:LiQ (50%:50%) 40 nm |
| E11 | SpA1 70 nm | HATCN 5 nm | BPA1 90 nm | H7:TEG1 (90%:10%) 30 nm | IC1 10 nm | ST1:LiQ (50%:50%) 30 nm |
| E12 | SpA1 70 nm | HATCN 5 nm | BPA1 90 nm | H8:TEG1 (90%:10%) 30 nm | IC1 10 nm | ST1:LiQ (50%:50%) 30 nm |
| E13 | SpA1 70 nm | HATCN 5 nm | BPA1 90 nm | H9:TEG1 (90%:10%) 30 nm | IC1 10 nm | ST1:LiQ (50%:50%) 30 nm |
| E14 | SpA1 70 nm | HATCN 5 nm | BPA1 90 nm | H13:TEG1 (90%:10%) 30 nm | IC1 10 nm | ST1:LiQ (50%:50%) 30 nm |

TABLE 1-continued

Structure of the OLEDs

| Ex. | HTL Thickness | IL Thickness | EBL Thickness | EML Thickness | HBL Thickness | ETL Thickness |
|---|---|---|---|---|---|---|
| E15 | SpA1 70 nm | HATCN 5 nm | BPA1 90 nm | H14:TEG1 (90%:10%) 30 nm | IC1 10 nm | ST1:LiQ (50%:50%) 30 nm |
| E16 | SpA1 70 nm | HATCN 5 nm | BPA1 90 nm | H15:TEG1 (90%:10%) 30 nm | IC1 10 nm | ST1:LiQ (50%:50%) 30 nm |
| E17 | SpA1 70 nm | HATCN 5 nm | BPA1 90 nm | H16:TEG1 (90%:10%) 30 nm | IC1 10 nm | ST1:LiQ (50%:50%) 30 nm |

TABLE 2

Data of the OLEDs

| Ex. | U1000 (V) | CE1000 (cd/A) | PE1000 (lm/W) | EQE 1000 | CIE x/y at 1000 cd/m$^2$ | L0 (cd/m$^2$) | L1 % | LT (h) |
|---|---|---|---|---|---|---|---|---|
| V1  | 3.5 | 55 | 50 | 15.2% | 0.36/0.60 | 4000 | 80 | 440 |
| V2  | 3.6 | 54 | 48 | 14.9% | 0.37/0.60 | 4000 | 80 | 350 |
| V3  | 3.8 | 57 | 49 | 15.9% | 0.37/0.61 | 4000 | 80 | 430 |
| V4  | 3.4 | 52 | 48 | 14.3% | 0.36/0.60 | 4000 | 80 | 350 |
| V5  | 3.3 | 51 | 49 | 14.3% | 0.36/0.60 | 4000 | 80 | 380 |
| V6  | 3.3 | 50 | 49 | 14.1% | 0.36/0.60 | 4000 | 80 | 390 |
| V7  | 3.5 | 58 | 52 | 16.2% | 0.36/0.36 | 4000 | 80 | 330 |
| V8  | 3.8 | 47 | 39 | 13.0% | 0.36/0.60 | 4000 | 80 | 340 |
| V9  | 3.6 | 49 | 43 | 13.6% | 0.36/0.60 | 4000 | 80 | 290 |
| V10 | 3.7 | 56 | 47 | 15.4% | 0.37/0.60 | 4000 | 80 | 360 |
| V11 | 3.5 | 48 | 43 | 13.3% | 0.36/0.60 | 4000 | 80 | 340 |
| E1  | 3.3 | 54 | 52 | 14.9% | 0.37/0.60 | 4000 | 80 | 460 |
| E2  | 3.2 | 59 | 57 | 16.3% | 0.37/0.60 | 4000 | 80 | 490 |
| E3  | 3.3 | 56 | 53 | 15.4% | 0.36/0.60 | 4000 | 80 | 420 |
| E4  | 3.1 | 55 | 55 | 15.2% | 0.36/0.60 | 4000 | 80 | 440 |
| E5  | 3.1 | 52 | 53 | 14.5% | 0.36/0.60 | 4000 | 80 | 420 |
| E6  | 3.2 | 58 | 56 | 16.0% | 0.36/0.61 | 4000 | 80 | 460 |
| E7  | 3.2 | 54 | 53 | 14.9% | 0.37/0.60 | 4000 | 80 | 380 |
| E8  | 3.3 | 55 | 52 | 15.2% | 0.36/0.60 | 4000 | 80 | 410 |
| E9  | 3.4 | 53 | 47 | 14.8% | 0.36/0.60 | 4000 | 80 | 420 |
| E10 | 3.5 | 52 | 46 | 14.3% | 0.36/0.60 | 4000 | 80 | 390 |
| E11 | 3.3 | 53 | 50 | 14.8% | 0.36/0.60 | 4000 | 80 | 470 |
| E12 | 3.2 | 55 | 54 | 15.2% | 0.36/0.60 | 4000 | 80 | 490 |
| E13 | 3.0 | 46 | 49 | 12.8% | 0.36/0.61 | 4000 | 80 | 420 |
| E14 | 3.2 | 60 | 58 | 16.5% | 0.37/0.61 | 4000 | 80 | 580 |
| E15 | 3.4 | 56 | 52 | 15.5% | 0.36/0.61 | 4000 | 80 | 530 |
| E16 | 3.2 | 53 | 53 | 14.8% | 0.37/0.60 | 4000 | 80 | 490 |
| E17 | 3.3 | 50 | 49 | 13.9% | 0.36/0.61 | 4000 | 80 | 370 |

TABLE 3

Structural formulae of the materials for the OLEDs

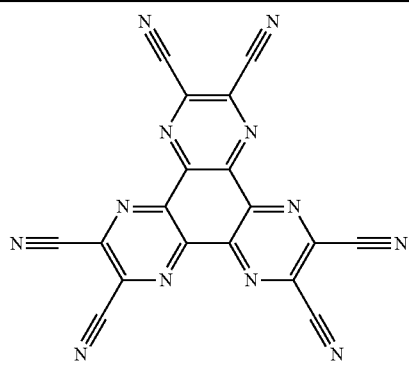

HATCN

TABLE 3-continued
Structural formulae of the materials for the OLEDs
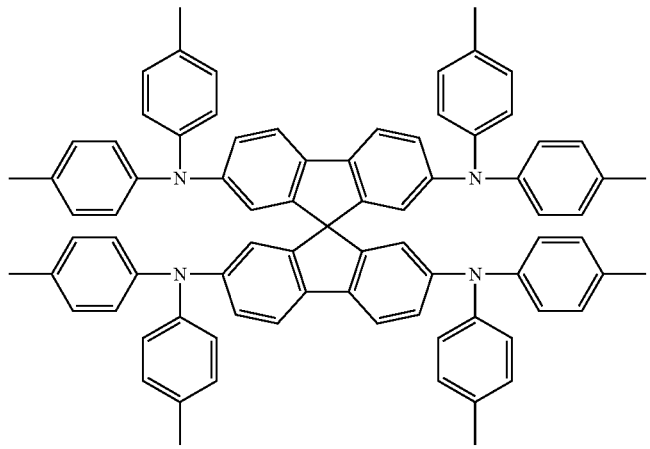
SpA1
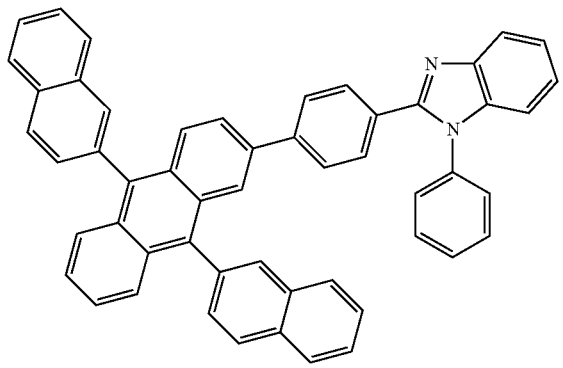 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]
ETM1
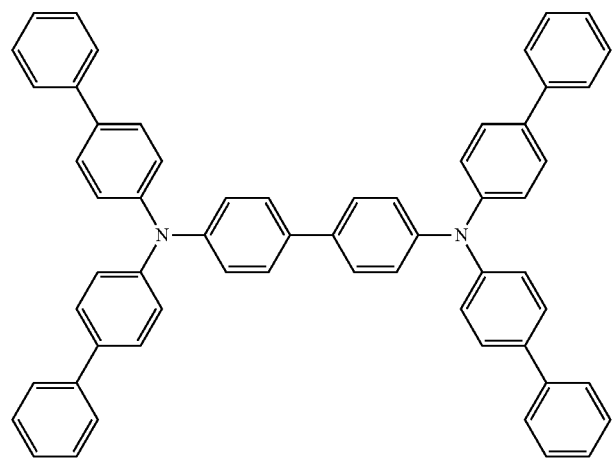 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
BPA1

TABLE 3-continued
Structural formulae of the materials for the OLEDs
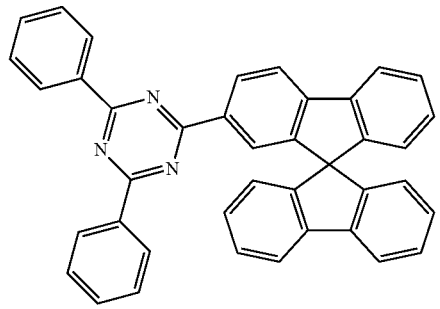 [SMILES: c1ccc(-c2nc(-c3ccccc3)nc(-c3ccc4c(c3)C3(c5ccccc5-c5ccccc53)c3ccccc3-4)n2)cc1]
ST1
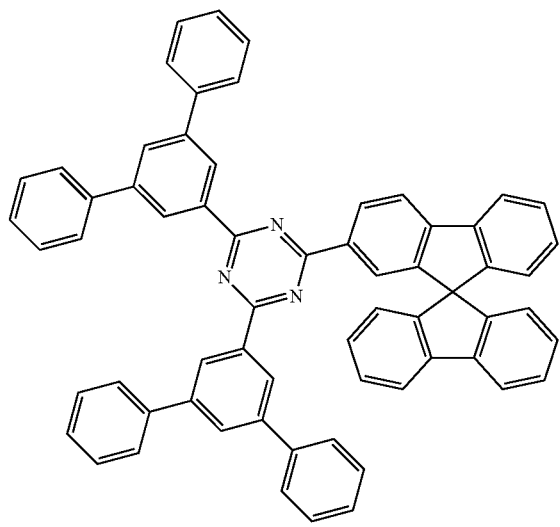 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
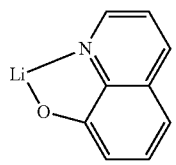
LiQ
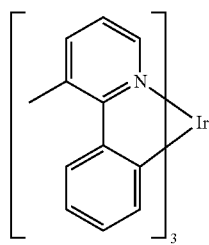
TEG1

TABLE 3-continued
Structural formulae of the materials for the OLEDs
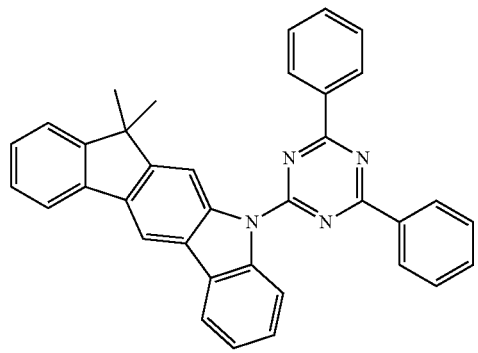 [SMILES: CC1(C)c2ccccc2-c2cc3c4ccccc4n(-c4nc(-c5ccccc5)nc(-c5ccccc5)n4)c3cc21]
IC1 (comparative material)
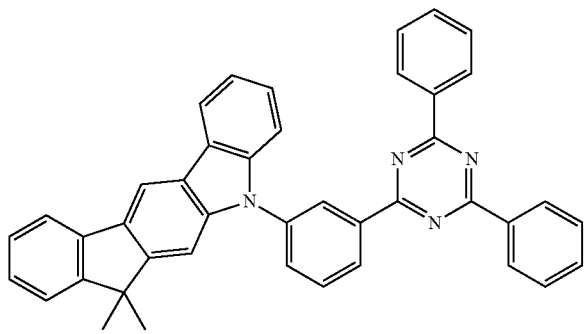 [SMILES: CC1(C)c2ccccc2-c2cc3c4ccccc4n(-c4cccc(-c5nc(-c6ccccc6)nc(-c6ccccc6)n5)c4)c3cc21]
IC2 (comparative material)
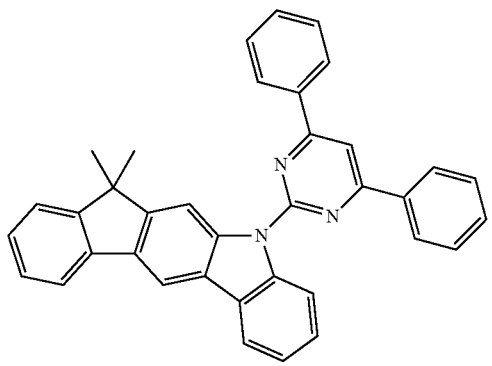 [SMILES: CC1(C)c2ccccc2-c2cc3c4ccccc4n(-c4nc(-c5ccccc5)cc(-c5ccccc5)n4)c3cc21]
IC3 (comparative material)
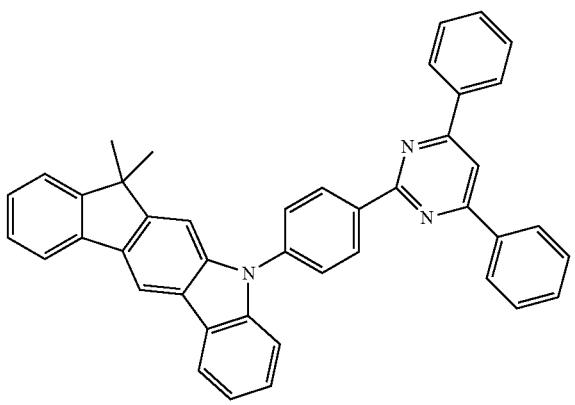 [SMILES: CC1(C)c2ccccc2-c2cc3c4ccccc4n(-c4ccc(-c5nc(-c6ccccc6)cc(-c6ccccc6)n5)cc4)c3cc21]
IC5 (comparative material)

TABLE 3-continued
Structural formulae of the materials for the OLEDs
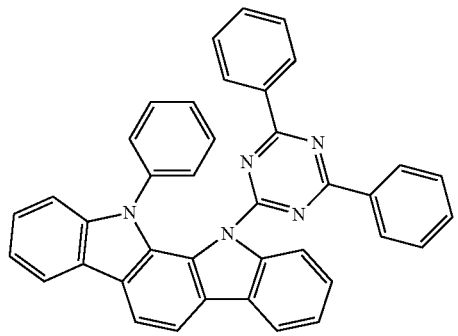 [SMILES: c1ccc(-c2nc(-c3ccccc3)nc(-n3c4ccccc4c4ccc5c6ccccc6n(-c6ccccc6)c5c43)n2)cc1]
IC6 (comparative material)
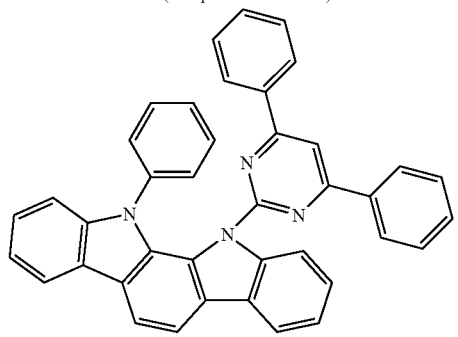
IC7 (comparative material)
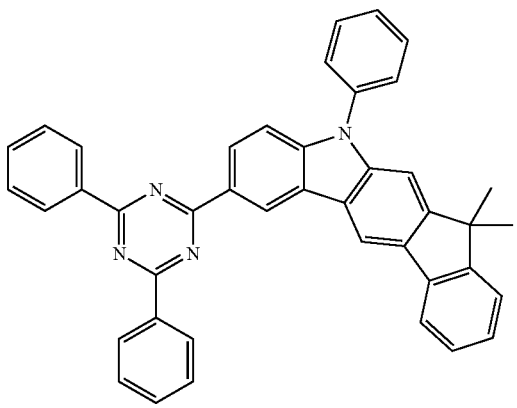 [SMILES: CC1(C)c2ccccc2-c2cc3c4cc(-c5nc(-c6ccccc6)nc(-c6ccccc6)n5)ccc4n(-c4ccccc4)c3cc21]
IC8 (comparative material)
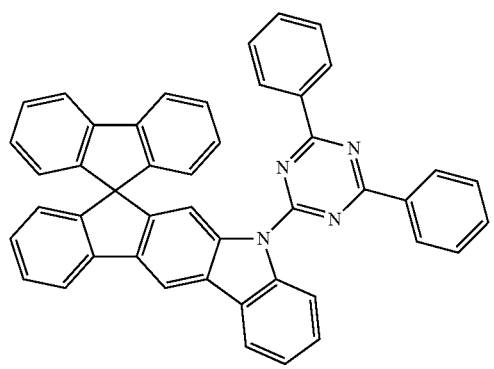 [SMILES: c1ccc(-c2nc(-c3ccccc3)nc(-n3c4ccccc4c4cc5c(cc43)C3(c4ccccc4-c4ccccc43)c3ccccc3-5)n2)cc1]
IC9 (comparative material)

TABLE 3-continued
Structural formulae of the materials for the OLEDs
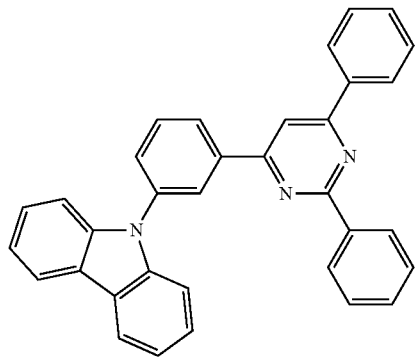 [SMILES: c1ccc(-c2cc(-c3cccc(-n4c5ccccc5c5ccccc54)c3)nc(-c3ccccc3)n2)cc1]
PyCbz1 (comparative material)
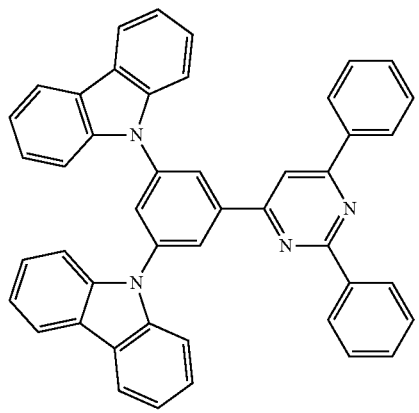 [SMILES: c1ccc(-c2cc(-c3cc(-n4c5ccccc5c5ccccc54)cc(-n4c5ccccc5c5ccccc54)c3)nc(-c3ccccc3)n2)cc1]
PyCbz2 (comparative material)
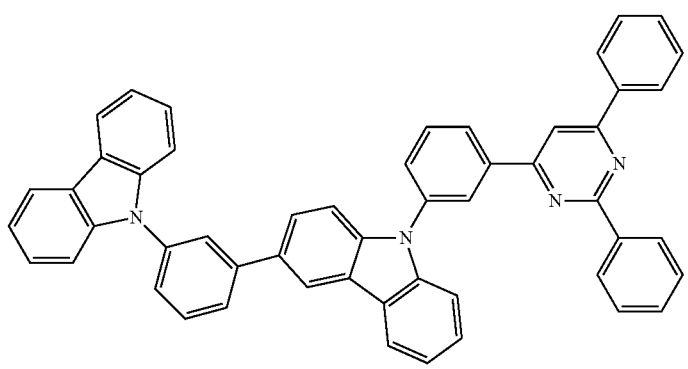 [SMILES: c1ccc(-c2cc(-c3cccc(-n4c5ccccc5c5cc(-c6cccc(-n7c8ccccc8c8ccccc87)c6)ccc54)c3)nc(-c3ccccc3)n2)cc1]
PyCbz3 (comparative material)

TABLE 3-continued
Structural formulae of the materials for the OLEDs
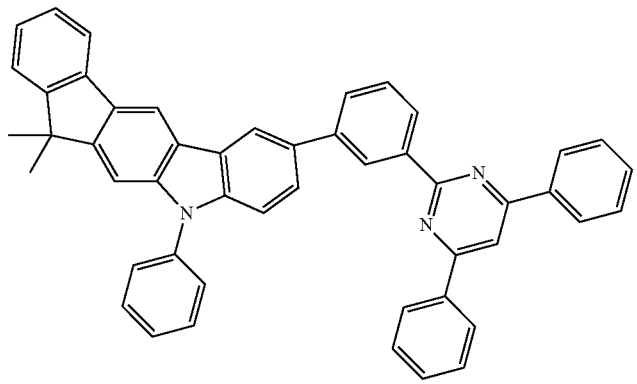 [SMILES: CC1(C)c2ccccc2-c2cc3c4cc(-c5cccc(-c6nc(-c7ccccc7)cc(-c7ccccc7)n6)c5)ccc4n(-c4ccccc4)c3cc21]
H1 (according to the invention)
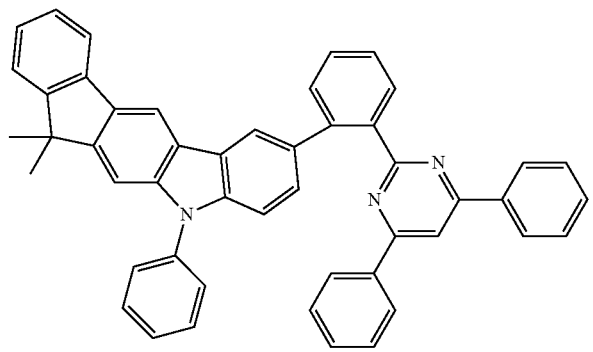 [SMILES: CC1(C)c2ccccc2-c2cc3c4cc(-c5ccccc5-c5nc(-c6ccccc6)cc(-c6ccccc6)n5)ccc4n(-c4ccccc4)c3cc21]
H2 (according to the invention)
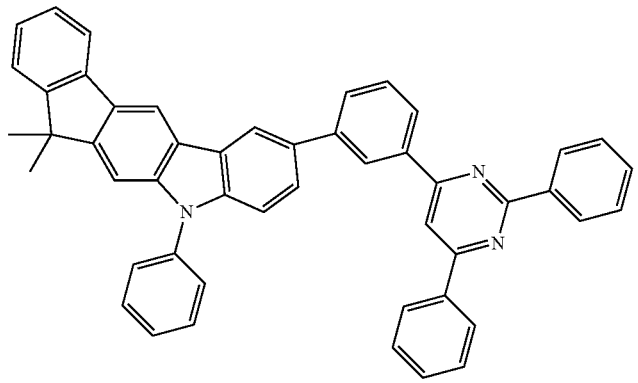 [SMILES: CC1(C)c2ccccc2-c2cc3c4cc(-c5cccc(-c6cc(-c7ccccc7)nc(-c7ccccc7)n6)c5)ccc4n(-c4ccccc4)c3cc21]
H3 (according to the invention)
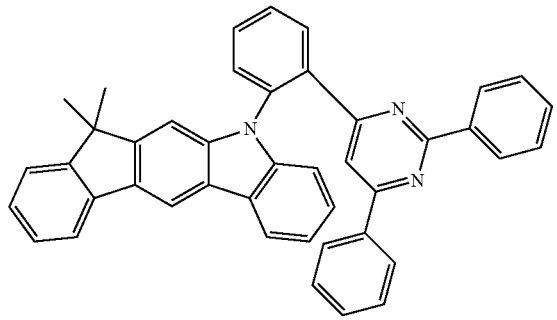 [SMILES: CC1(C)c2ccccc2-c2cc3c4ccccc4n(-c4ccccc4-c4cc(-c5ccccc5)nc(-c5ccccc5)n4)c3cc21]
H4 (according to the invention)

TABLE 3-continued
Structural formulae of the materials for the OLEDs
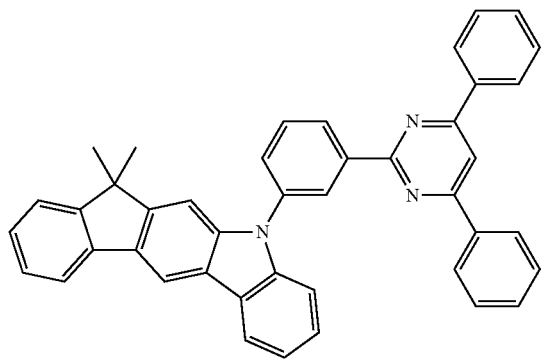 [SMILES: CC1(C)c2ccccc2-c2cc3c4ccccc4n(-c4cccc(-c5nc(-c6ccccc6)cc(-c6ccccc6)n5)c4)c3cc21]
H5 (according to the invention)
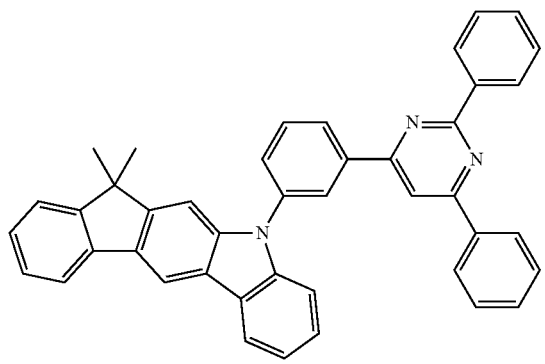 [SMILES: CC1(C)c2ccccc2-c2cc3c4ccccc4n(-c4cccc(-c5cc(-c6ccccc6)nc(-c6ccccc6)n5)c4)c3cc21]
H6 (according to the invention)
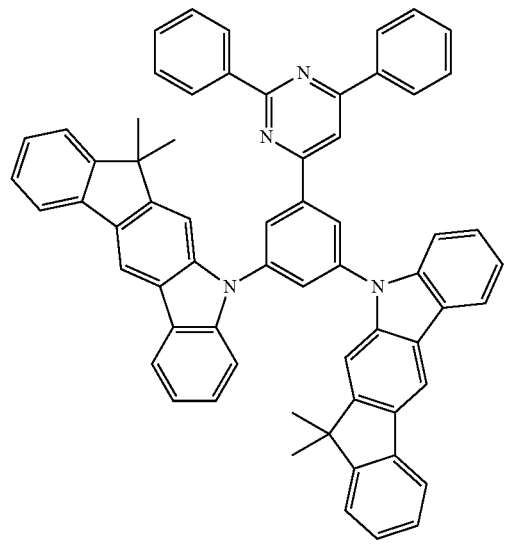 [SMILES: CC1(C)c2ccccc2-c2cc3c4ccccc4n(-c4cc(-c5cc(-c6ccccc6)nc(-c6ccccc6)n5)cc(-n5c6ccccc6c6cc7c(cc65)C(C)(C)c5ccccc5-7)c4)c3cc21]
H7 (according to the invention)

TABLE 3-continued
Structural formulae of the materials for the OLEDs
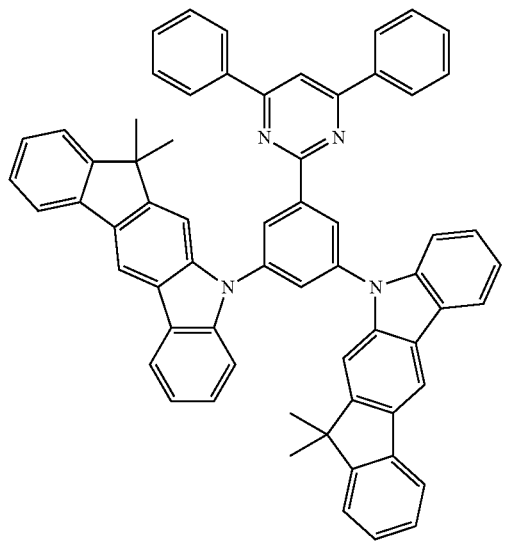 [SMILES: CC1(C)c2ccccc2-c2cc3c4ccccc4n(-c4cc(-c5nc(-c6ccccc6)cc(-c6ccccc6)n5)cc(-n5c6ccccc6c6cc7c(cc65)C(C)(C)c5ccccc5-7)c4)c3cc21]
H8 (according to the invention)
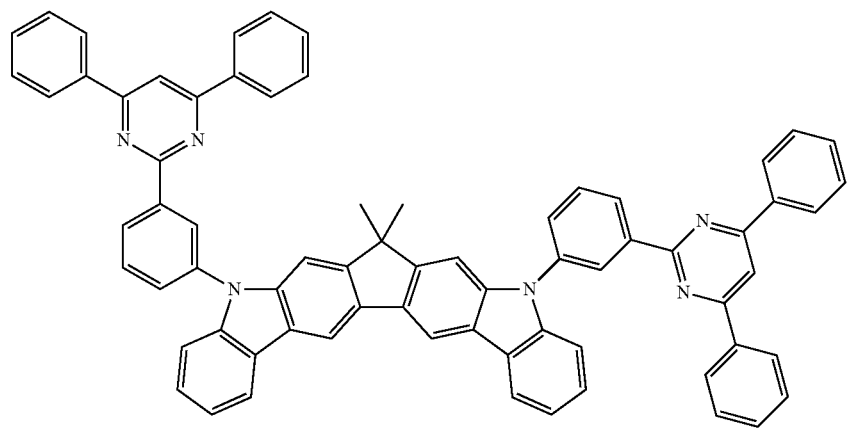 [SMILES: CC1(C)c2cc3c(cc2-c2cc4c5ccccc5n(-c5cccc(-c6nc(-c7ccccc7)cc(-c7ccccc7)n6)c5)c4cc21)c1ccccc1n3-c1cccc(-c2nc(-c3ccccc3)cc(-c3ccccc3)n2)c1]
H9 (according to the invention)
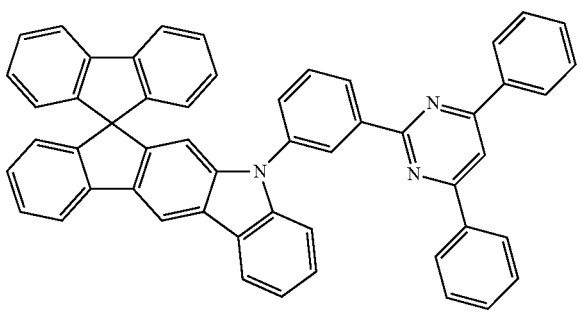 [SMILES: c1ccc(-c2cc(-c3ccccc3)nc(-c3cccc(-n4c5ccccc5c5cc6c(cc54)C4(c5ccccc5-c5ccccc54)c4ccccc4-6)c3)n2)cc1]
H10 (according to the invention)

TABLE 3-continued
Structural formulae of the materials for the OLEDs
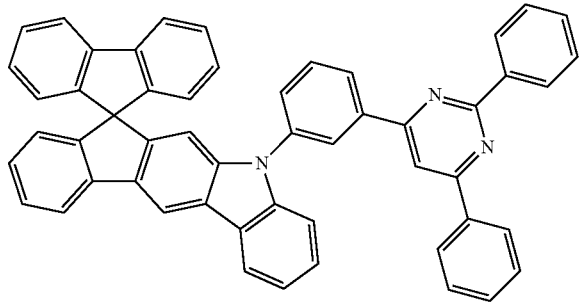 [SMILES: c1ccc(-c2cc(-c3cccc(-n4c5ccccc5c5cc6c(cc54)C4(c5ccccc5-c5ccccc54)c4ccccc4-6)c3)nc(-c3ccccc3)n2)cc1]
H11 (according to the invention)
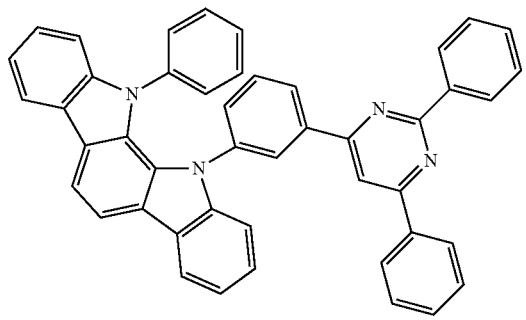 [SMILES: c1ccc(-c2cc(-c3cccc(-n4c5ccccc5c5ccc6c7ccccc7n(-c7ccccc7)c6c54)c3)nc(-c3ccccc3)n2)cc1]
H12 (according to the invention)
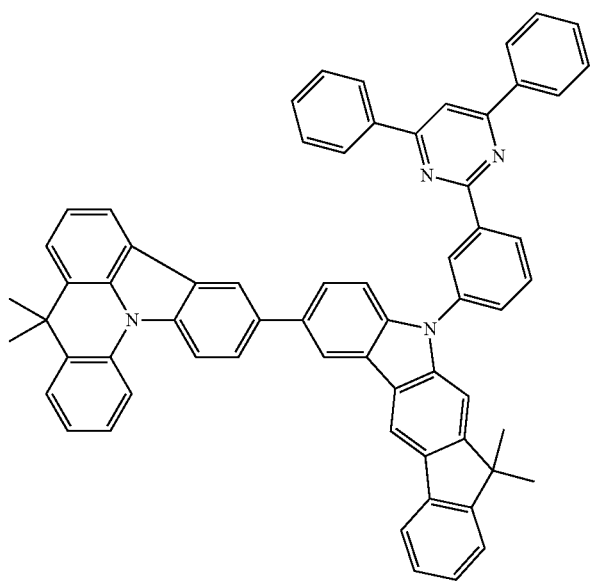 [SMILES: CC1(C)c2ccccc2-c2cc3c4cc(-c5ccc6c(c5)c5cccc7c5n6-c5ccccc5C7(C)C)ccc4n(-c4cccc(-c5nc(-c6ccccc6)cc(-c6ccccc6)n5)c4)c3cc21]
H13 (according to the invention)

TABLE 3-continued
Structural formulae of the materials for the OLEDs
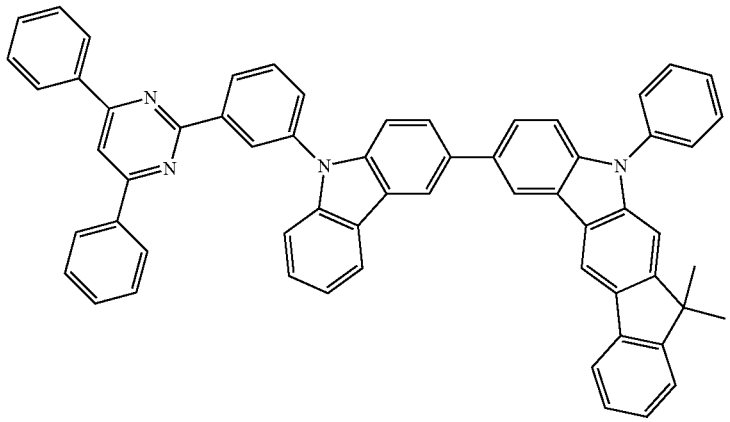 [SMILES: CC1(C)c2ccccc2-c2cc3c4cc(-c5ccc6c(c5)c5ccccc5n6-c5cccc(-c6nc(-c7ccccc7)cc(-c7ccccc7)n6)c5)ccc4n(-c4ccccc4)c3cc21]
H14 (according to the invention)
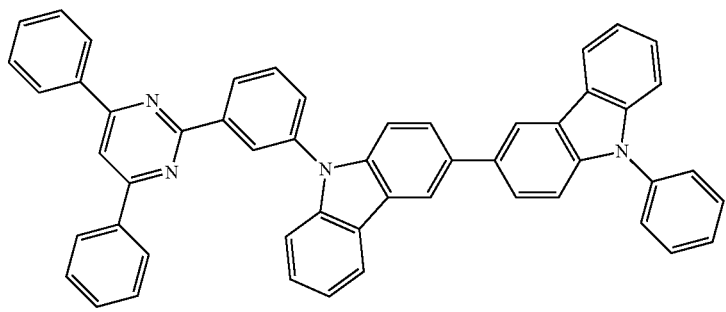 [SMILES: c1ccc(-c2cc(-c3ccccc3)nc(-c3cccc(-n4c5ccccc5c5cc(-c6ccc7c(c6)c6ccccc6n7-c6ccccc6)ccc54)c3)n2)cc1]
H15 (according to the invention)
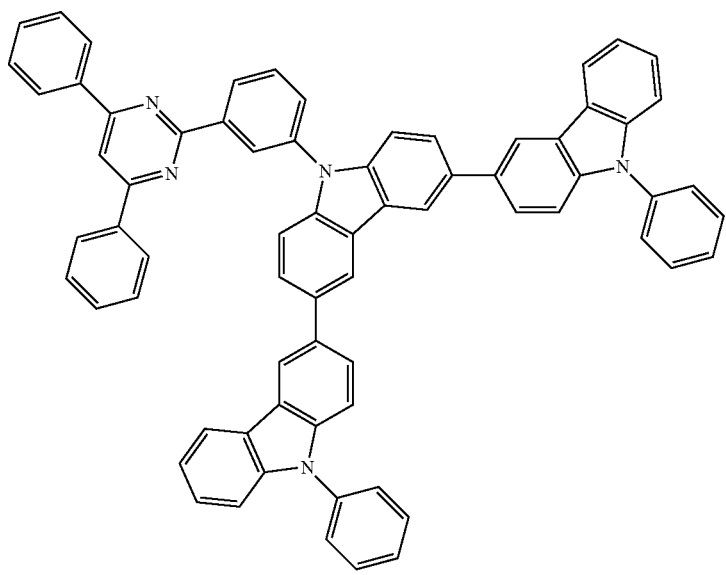 [SMILES: c1ccc(-c2cc(-c3ccccc3)nc(-c3cccc(-n4c5ccc(-c6ccc7c(c6)c6ccccc6n7-c6ccccc6)cc5c5cc(-c6ccc7c(c6)c6ccccc6n7-c6ccccc6)ccc54)c3)n2)cc1]
H16 (according to the invention)

The invention claimed is:

1. A compound of the formula (1) or formula (2),

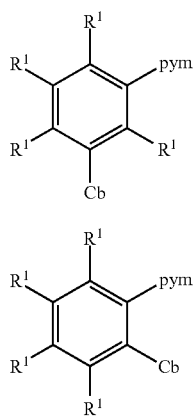

where the following applies to the symbols used:

pym is a pyrimidine, which is optionally substituted by one or more radicals R;

Cb is a carbazole derivative which contains at least 2 bridges, in which, in addition, one or more C atoms is optionally replaced by N and which is optionally substituted by one or more radicals $R^2$;

R, $R^1$ and $R^2$ are selected on each occurrence, identically or differently, and are H, D, F, Cl, Br, I, CN, $NO_2$, $N(Ar)_2$, $N(R^3)_2$, C(=O)Ar, C(=O)$R^3$, P(=O)$(Ar)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^3$, where one or more non-adjacent $CH_2$ groups is optionally replaced by $R^3C$=$CR^3$, C≡C Si$(R^3)_2$, C=O, C=S, C=$NR^3$, P(=O)$(R^3)$, SO, $SO_2$, $NR^3$, O, S or $CONR^3$ and where one or more H atoms is optionally replaced by D, F, Cl, Br, I, CN or $NO_2$, an aromatic or heteroaromatic ring system having 5 to 80 aromatic ring atoms, which may in each case be substituted by one or more radicals $R^3$, an aryloxy or heteroaryloxy group having 5 to 60 aromatic ring atoms, which is optionally substituted by one or more radicals $R^3$, or an aralkyl or heteroaralkyl group having 5 to 60 aromatic ring atoms, which is optionally substituted by one or more radicals $R^3$, where two or more adjacent substituents $R^2$ may optionally form a monocyclic or polycyclic, aliphatic, aromatic or heteroaromatic ring system, which is optionally substituted by one or more radicals $R^3$;

$R^3$ is on each occurrence, identically or differently, H, D, F, Cl, Br, I, CN, $NO_2$, $N(Ar)_2$, $N(R^4)_2$, C(=O)Ar, C(=O)$R^4$, P(=O)$(Ar)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^3$, where one or more non-adjacent $CH_2$ groups is optionally replaced by $R^4C$=$CR^4$, Si$(R^4)_2$, C=O, C=S, C=Se, C=$NR^4$, P(=O)$(R^4)$, SO, $SO_2$, $NR^4$, O, S or $CONR^4$ and where one or more H atoms is optionally replaced by D, F, Cl, Br, I, CN or $NO_2$, an aromatic or hetero-aromatic ring system having 5 to 60 aromatic ring atoms, which may in each case be substituted by one or more radicals $R^4$, an aryloxy or heteroaryloxy group having 5 to 60 aromatic ring atoms, which is optionally substituted by one or more radicals $R^4$, or an aralkyl or heteroaralkyl group having 5 to 60 aromatic ring atoms, where two or more adjacent substituents $R^3$ may optionally form a monocyclic or polycyclic, aliphatic, aromatic or heteroaromatic ring system, which is optionally substituted by one or more radicals $R^4$;

Ar is on each occurrence, identically or differently, an aromatic or heteroaromatic ring system having 5-30 aromatic ring atoms, which is optionally substituted by one or more non-aromatic radicals $R^4$; two radicals Ar here which are bonded to the same N atom or P atom may also be bridged to one another by a single bond or a bridge selected from N$(R^4)$, C$(R^4)_2$, O or S;

$R^4$ is H, D, F, CN, an aliphatic hydrocarbon radical having 1 to 20 C atoms, an aromatic or heteroaromatic ring system having 5 to 30 aromatic ring atoms, in which one or more H atoms is optionally replaced by D, F, Cl, Br, I or CN, where two or more adjacent substituents $R^4$ may form a mono- or polycyclic, aliphatic, aromatic or heteroaromatic ring system with one another;

the following compounds are excluded from the invention:

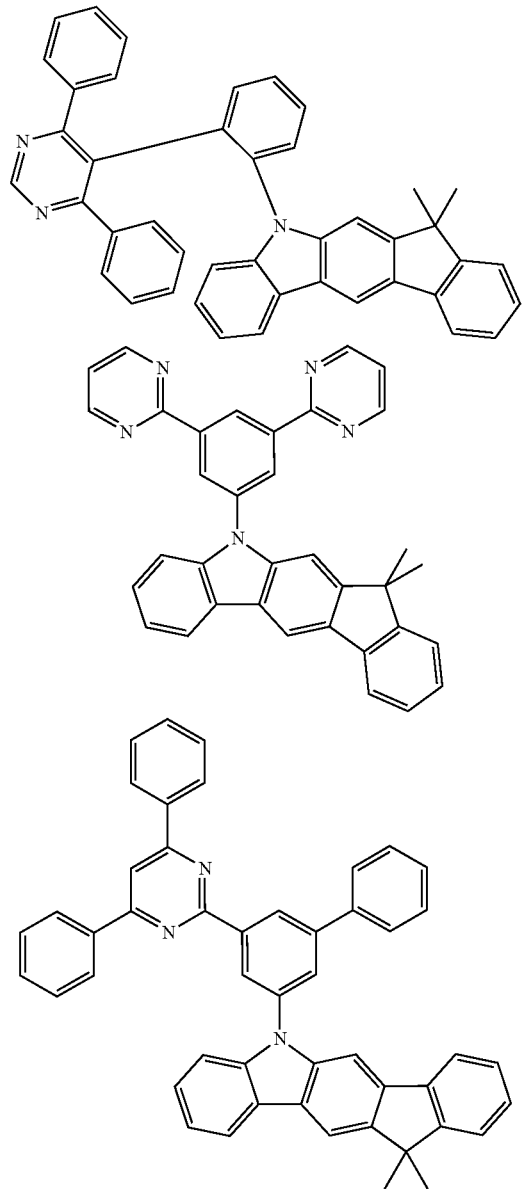

-continued

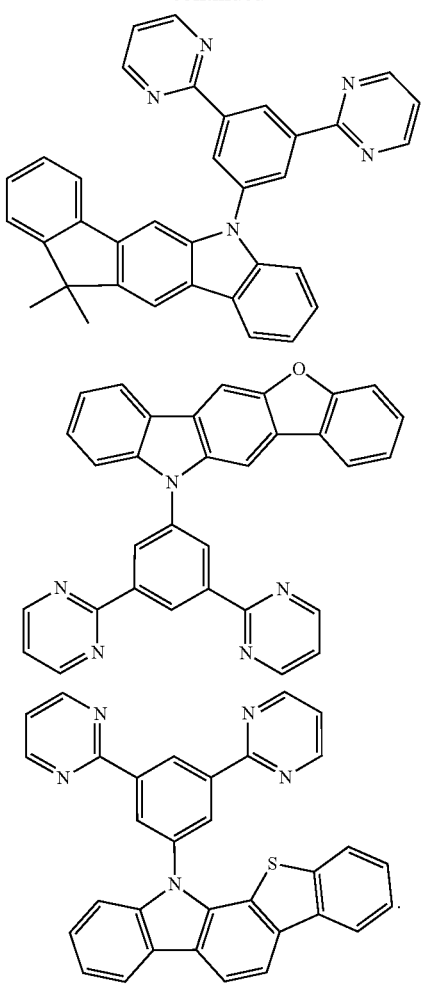

2. The compound according to claim 1, wherein the compounds of the formula (1) are selected from the compounds of the formulae (1 a), (1 b) or (1 c) and in that the compounds of the formula (2) are compounds of the formula (2a),

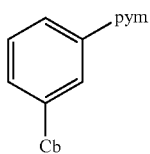

formula (1a)

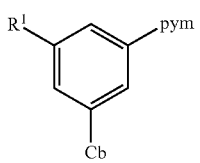

formula (1b)

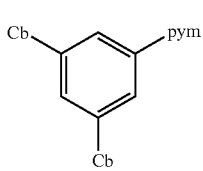

formula (1c)

-continued

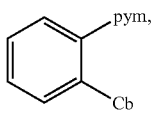

formula (2a)

where the symbols used have the meanings given in claim 1.

3. The compound according to claim 1, wherein $R^1$ represents H or an aromatic or heteroaromatic ring system having 5 to 24 aromatic ring atoms, which is optionally substituted by one or more radicals $R^3$.

4. The compound according to claim 1, wherein the group pym is selected from the groups of the formulae (3), (4) or (5),

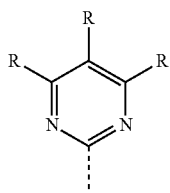

formula (3)

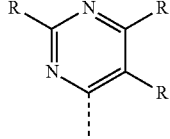

formula (4)

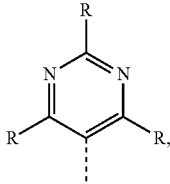

formula (5)

Where the symbols used have the meanings given in claim 1 and the dashed bond indicates the bond to the phenyl group in formula (1) or (2).

5. The compound according to claim 4, wherein the group pym is selected from the formulae (3a), (4a) and (5a),

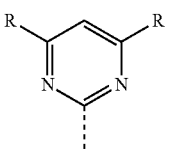

formula (3a)

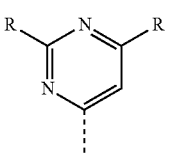

formula (4a)

formula (5a)

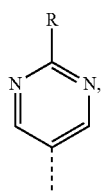

Where the symbols used have the meanings given in claim 1 and the dashed bond represents the bond from the pyrimidine to the phenyl group of the formula (1) or (2).

6. The compound according to claim 1, wherein R stands, identically or differently on each occurrence, for H, an alkyl group having 1 to 10 C atoms or for an aromatic or heteroaromatic ring system having 5 to 24 aromatic ring atoms, which is optionally substituted by one or more radicals $R^3$.

7. The compound according to claim 1, wherein the group Cb is selected from the groups of the formulae (6) to (22), formula (6)

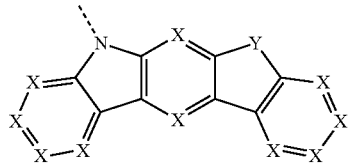

formula (7)

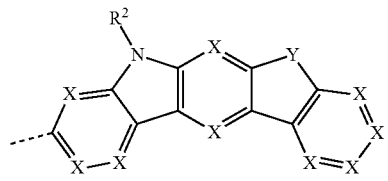

formula (8)

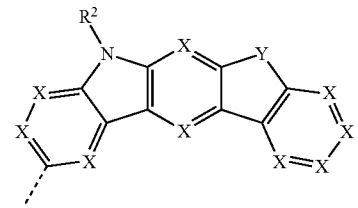

formula (9)

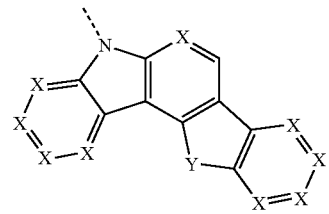

formula (10)

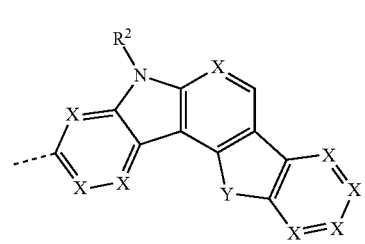

formula (11)

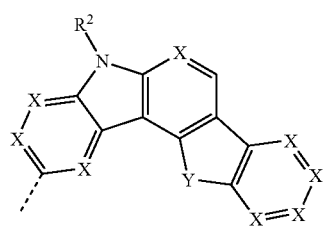

formula (12)

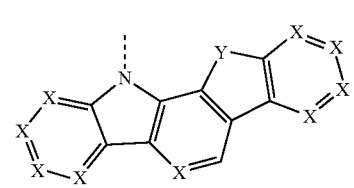

formula (13)

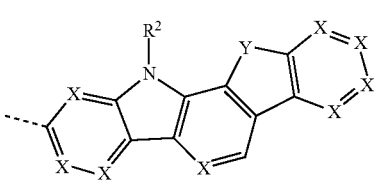

formula (14)

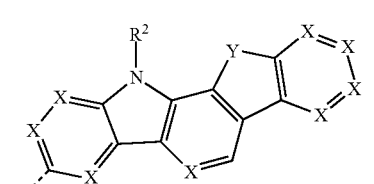

formula (15)

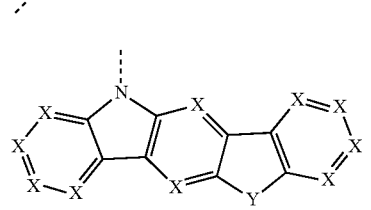

formula (16)

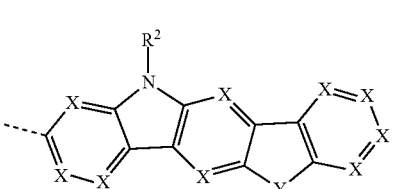

formula (17)

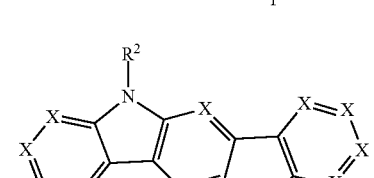

formula (18)

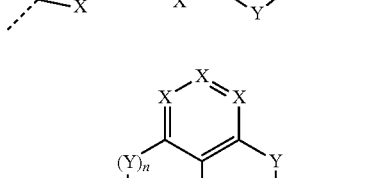

-continued formula (19)
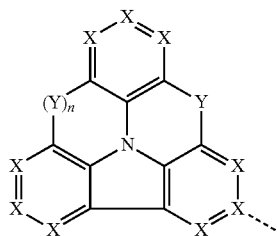

formula (20)
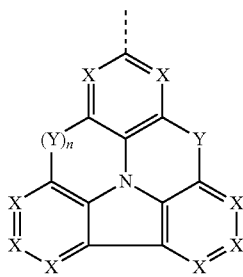

formula (21)
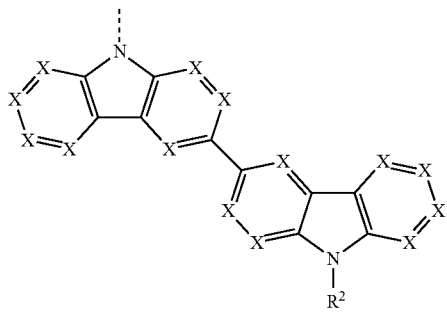

formula (22)
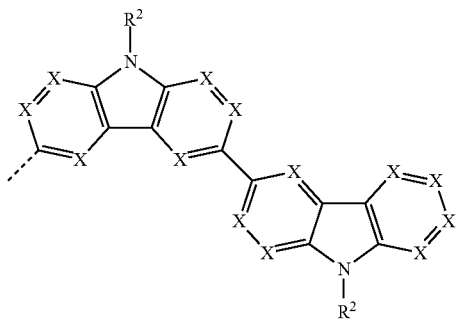

where the symbols used have the meanings given in claim 1, the dashed bond represents the bond from the carbazole derivative to the phenyl group of the formula (1) or (2) and X is on each occurrence, identically or differently, $CR^2$ or N, where a maximum of 2 symbols X per ring stand for N;

Y is on each occurrence, identically or differently, $C(R^2)_2$, $NR^2$, O or S;

n is 0 or 1, where n equals 0 means that no group Y is bonded at this position and instead radicals $R^2$ are bonded to the corresponding carbon atoms.

8. The compound according to claim 7, wherein the symbol X stands, identically or differently on each occurrence, for $CR^2$.

9. The compound according to claim 7, wherein the symbol X stands, identically or differently on each occurrence, CH.

10. The compound according to claim 1, wherein the substituent $R^2$, which is bonded directly to a nitrogen atom in the bridge of a carbazole derivative, stands for an aromatic or heteroaromatic ring system having 5 to 24 aromatic ring atoms, which may also be substituted by one or more radicals $R^3$.

11. The compound according to claim 1, wherein the group Cb is selected from the groups of the formulae (7), (8), (10), (11), (13), (14), (16) to (19), (21) and (22), formula (7)
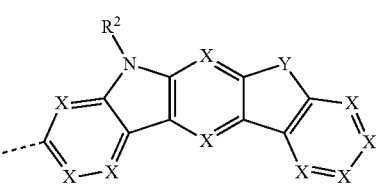

formula (8)
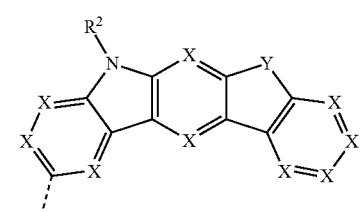

formula (10)
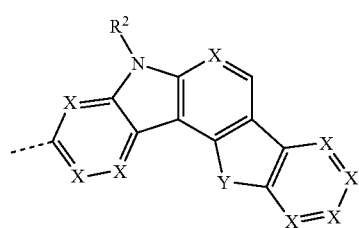

formula (11)
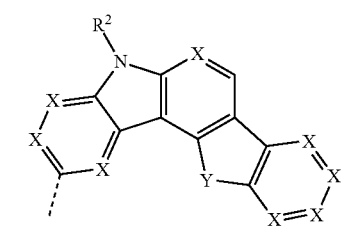

formula (13)
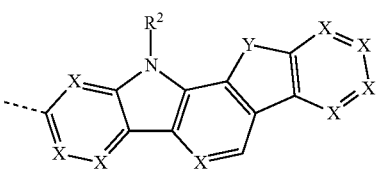

formula (14)

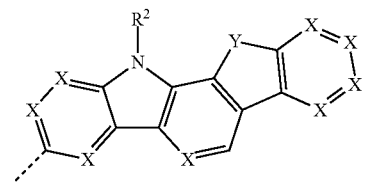

formula (16)

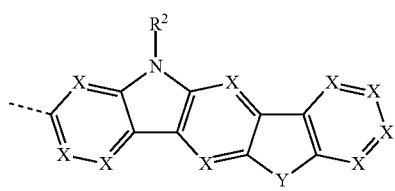

formula (17)

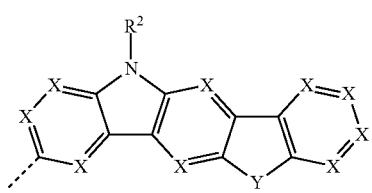

formula (18)

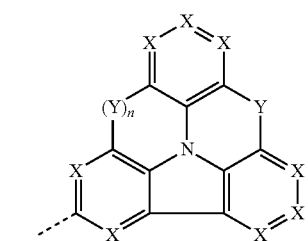

formula (19)

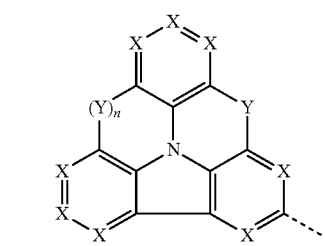

formula (21)

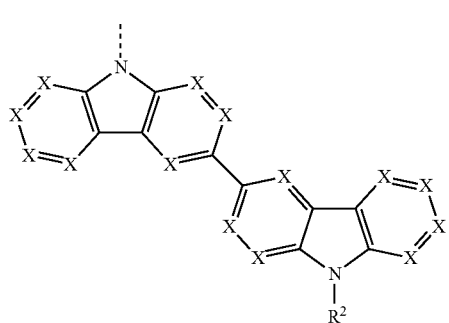

formula (22)

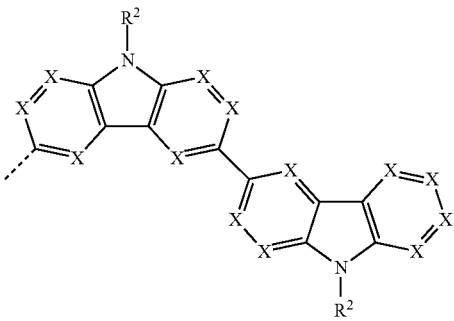

where the symbols used have the meanings given in claim 1, the dashed bond represents the bond from the carbazole derivative to the phenyl group of the formula (1) or (2) and X is on each occurrence, identically or differently, $CR^2$ or N, where a maximum of 2 symbols X per ring stand for N;

Y is on each occurrence, identically or differently, $C(R^2)_2$, $NR^2$, O or S;

n is 0 or 1, where n equals 0 means that no group Y is bonded at this position and instead radicals $R^2$ are bonded to the corresponding carbon atoms.

12. A mixture comprising at least one compound according to claim 11 and at least one further compound.

13. A mixture comprising at least one compound according to claim 11 and at least one further compound, wherein the one further compound is a fluores-cent or phosphorescent dopant.

14. A formulation comprising at least one compound or according to claim 11 and one or more solvents.

15. An electronic device which comprises the compound according to claim 11.

16. An organic electroluminescent device which comprises the compound according to claim 11.

17. The electronic device according to claim 15, wherein the electronic device is an organic electroluminescent device, an organic integrated circuit, an organic field-effect transistor, an organic thin-film transistor, an organic light-emitting transistor, an organic solar cell, an organic dye-sensitised solar cell, an organic optical detector, an organic photoreceptor, an organic field-quench device, a light-emitting electrochemical cell, an organic laser diode or an organic plasmon emitting device.

18. An organic electroluminescent device which comprises the compound according to claim 11 is present as matrix material for fluorescent or phosphorescent emitters and/or in a hole-blocking layer and/or in an electron-transport layer.

19. A process for the preparation of the compound according to claim 1, comprising the reaction steps:
   a) synthesis of an optionally substituted phenylpyrimidine derivative which contains a reactive leaving groups on the phenyl group in the meta-position or in the ortho-position to the pyrimidine; and
   b) coupling of this phenylpyrimidine derivative to a carbazole derivative.

* * * * *